United States Patent [19]
Riley et al.

[11] Patent Number: 5,637,578
[45] Date of Patent: Jun. 10, 1997

[54] MANGANESE COMPLEXES OF NITROGEN-CONTAINING MACROCYCLIC LIGANDS EFFECTIVE AS CATALYSTS FOR DISMUTATING SUPEROXIDE

[76] Inventors: Dennis P. Riley, 800 Chancellor Hgts. Dr., Ballwin, Mo. 63011; Randy H. Weiss, 11062 "L" Oak Spur Ct., St. Louis, Mo. 63146; William L. Neuman, 968 Coventry Ct., Creve Coeur, Mo. 63141; Anil S. Modak, 1193 Schulte Hill, Maryland Heights, Mo. 63043; Patrick J. Lennon, 7540 Wydown Blvd. #3 W., Clayton, Mo. 63105; Karl W. Aston, 19040 Sunflower Ridge La., Pacific, Mo. 63069

[21] Appl. No.: 442,454

[22] Filed: May 16, 1995

Related U.S. Application Data

[62] Division of Ser. No. 80,732, Jun. 22, 1993, which is a continuation of Ser. No. 902,146, Jun. 26, 1992, abandoned, which is a continuation-in-part of Ser. No. 829,865, Feb. 3, 1992, abandoned, which is a continuation-in-part of Ser. No. 732,853, Jul. 19, 1991, abandoned.

[51] Int. Cl.$^6$ .................... C07D 487/22; A61K 31/675; A61K 47/16
[52] U.S. Cl. .................... 514/186; 514/183; 514/184; 540/472; 540/474; 540/473
[58] Field of Search ................... 540/474, 472; 514/183, 186, 184

[56] References Cited

U.S. PATENT DOCUMENTS

| | | | |
|---|---|---|---|
| 3,930,867 | 1/1976 | Bigelow | 540/474 |
| 4,001,212 | 1/1977 | Richman | 540/474 |
| 4,702,998 | 10/1987 | Tanaka et al. | 540/474 |
| 4,885,363 | 12/1989 | Tweedle et al. | 540/465 |
| 5,096,724 | 3/1992 | Zenner et al. | 426/124 |

FOREIGN PATENT DOCUMENTS

| | | |
|---|---|---|
| 14611/88 | 4/1987 | Australia . |
| 1461188 | 4/1988 | Australia . |
| 0284645 | 5/1987 | European Pat. Off. . |
| 0287465 | 4/1988 | European Pat. Off. . |
| 0284645 | 5/1988 | European Pat. Off. . |
| 0374929 | 12/1989 | European Pat. Off. . |
| 0391766 | 3/1990 | European Pat. Off. . |
| 0374929 | 6/1990 | European Pat. Off. . |
| 391766 | 10/1990 | European Pat. Off. . |
| 0436189A1 | 12/1990 | European Pat. Off. . |
| 59-98074 | 6/1984 | Japan . |
| 59/098074 | 6/1984 | Japan . |
| 8912119 | 12/1981 | WIPO . |
| 89/12119 | 12/1989 | WIPO . |
| WO91/10645 | 7/1991 | WIPO . |
| WO93/06868 | 4/1993 | WIPO . |

OTHER PUBLICATIONS

Michelson Life Chemistry Reviews 17876 1–142.
Bardo et al. J. Heart Lung Transplant 10(2) 1991 pp. 304–309.
Marklund Adv Clin Enzymol 135–144, p. 6 Oberely.
Oberely, Free Radical Biology and Medicines 5 pp. 113–124, 1988.
Storhoff et al. Coord Chem. Rev 23 (1977) 1–29.
Wisner et al Gut 1988 29 1516–1523.
Newton et al., J. Coord. Chem 19 pp. 265–277 1988.
Petknu Cancer Treatment Reviews 1986 1317–44.
Akaike et al. J. Clin. Invest. 85 1990 739–745.
Trenam J. of Dermatology (1991) 125 325–329.
Cremer et al. J Heart Transplantation Aug. 1989, pp. 330–335.
Rush Archives of Biochem and Biophys 289(1) p. 1–6 1991.
Kimura et al. Biochimica et Biophysica Acta 678 (1981) 172–179.
Kimura et al. Biochimica et Biophysica Acta 1983 37–43.
Bell et al., JACS 1983 105 5290–5300.
Riley et al, Analytical Biochem. 196 344–349 1991.
Newton, et al. Chemical Abstracts, vol. 110 1989 Al 146606P.
Krakowiak, J. Org. Chem. 1990 3364–3368.
Gryglewski et al Nature vol. 320 1986 pp. 454–456.
Alexander et al Inorg Nucl Chem Letters vol. 6 pp. 445–448, 1970.
Brady, et al J. Org. Chem. 44(18) 1979 pp. 3103–3105.
Tabushi et al. Tetrahedron Letters 12 pp. 1049–1057, 11 11.
Fujioka Chemistry Letters pp. 737–740 1982.
Atkins, et al Org Synth vol. 58 pp. 344–341 1978.
Richman et al. JACS vol. 96 1974 pp. 2268–2278.
Krakowiak et al. Tetrahedron Letters 30(22) pp. 2987–2900 1989.
Bradshaw et al. J Heterocyclic Chem 26 1431 (1989).
Jackels et al. Inorg. Chem. 1992 31 234–239.
Bencini et al. Inorg. Chem. 1990 29 1716–1718.
Fretland et al., *Gastroenterology*, 100, A581 (1990).

(List continued on next page.)

*Primary Examiner*—Mukund J. Shah
*Assistant Examiner*—Pavanaram K. Sripada

[57] ABSTRACT

The present invention is directed to low molecular weight mimics of superoxide dismutase (SOD) represented by the formula:

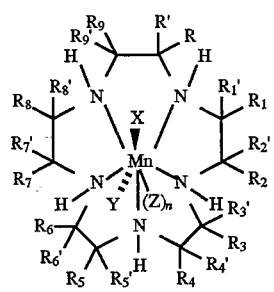

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ and X, Y, Z and n are as defined herein, useful as therapeutic agents for inflammatory disease states and disorders, ischemic/reperfusion injury, stroke, atherosclerosis, hypertension and all other conditions of oxidant-induced tissue damage or injury.

3 Claims, 1 Drawing Sheet

OTHER PUBLICATIONS

McCord, *Free Radicals Biol. Med.* 2, 307 (1986).

Bannister et al., *Crit. Rev. Biochem.*, 22, 111 (1987).

Jackels, S.C. et al., "Agueous Proton NMR Relaxation Enhancement by Manganese (II) Macrocyclic Complexes: Structure–Relaxivity Relationships", *Inorg. Chem.*, 31, 234–239 (1992).

Newton, J.E. et al., Synthesis and Characterization of the Mn(II) Complex of [15]aneN$_5$, *J. Coord. Chem.*, vol. 19, pp. 265–277 (1988).

Weiss, R. H. et al., Catalytic Efficacies of Agents that Dismutate Superoxide, *J. Cell. Biochem.*, Suppl. 15C,216, abstract CC110 (1991).

Petkau, A., Scientific Basis for the Clinical Use of Superoxide Dismutase, *Cancer Treat. Rev.*, vol. 13, pp. 17–44 (1986).

McCord, J. M. Superoxide Dismutase: Rationale for Use in Reperfusion Injury and Inflammation, *J. Free Radicals Biol. Med.*, vol. 2, pp. 307–310 (1986).

Bannister, J.V. et al., Aspects of the Structure, Function, and Applications of Superoxide Dismutase, CRC Crit. Rev. Biochem. vol. 22, pp. 111–180 (1987).

Richman, J.E. et al., Nitrogen Analogs of Crown Ethers, *J. Am. Chem. Soc.* vol. 96, pp. 2268–2270 (1974).

Atkins, T.J. et al., Macrocyclic Polyamines: 1,4,7,10,13,16–Hexaazacyclo–octadecane, *Org. Synth.*, vol. 58, pp. 86–98 (1978).

Riley, D.P. et al., Stopped–Flow Kinetic Analysis for Monitoring Superoxide Decay in Aqueous Systems, *Anal. Biochem.*, vol. 196, pp. 344–349 (1991).

Bull, C. et al., The Mechanisms of Fe–EDTA Catalyzed Superoxide Dismutation, *J. Am. Chem. Soc.*, vol. 105, pp. 5290–5300 (1983).

Kimura, E. et al., Further Studies on Superoxide Dismutase Activities of Macrocyclic Polyamine Complexes of Copper (II), *Biochim. Biophys. Acta*, vol. 745, pp. 37–43 (1983).

Kimura, E. et al., Superoxide Dismutase Activity of Macrocyclic Polyamine Complexes, *Biochim. Biophys. Acta*, vol. 678, pp. 172–179 (1981).

Rush, J. D. et al., The Superoxide Dismutase Activities of Two Higher–Valent Manganese Comp14exes, Mn$^{IV}$ Desferrioxamine and Mn$^{III}$ Cyclom, *Arch. Biochem. Biophys.*, vol. 289, pp. 1–6 (1991).

Fretland, D.J. et al., Superoxide Dismutase (SOD) Modulates Acetic Acid–Induced Colitis in Rodents, *Gastroenterology*, vol. 100, p. A581 (1990).

Gryglewski, R. J. et al., Superoxide Anion is Involved in the Breakdown of Endothelium–Derived Vascular Relaxing Factor, *Nature*, vol. 320, pp. 454–456 (1986).

Alexander, M.D., Manganese (II) Complexes of a Macrocyclic Ligand, *Inorg. Nucl. Chem. Letters*, vol. 6, pp. 445–448 (1970).

Brady, S.F. et al., Practical Synthesis of Cyclic Peptides, with an Example of Dependence of Cyclization Yield upon Linear Sequence, *J. Org. Chem.*, vol. 44, pp. 3101–3105 (1979).

Tabushi, I. et al., Preparation of C–Alkylated Macrocyclic Polyamines, *Tetrahedron Letters*, No. 12, pp. 1049–1052 (1977).

Fujioka, H. et al., The Effects of Size and Donor Atoms of Macrocylic Polyamines Binding to $Mg^{2+}$ and $Ca^{2+}$, *Chem. Letters.*, pp. 737–740 (1982).

Krakowiak, K.E. et al., Preparation of Triaza–, Tetraaza– and Peraza–Crown Compounds Containing Aminoalklyl Side Groups or Unsubstituted King Nitrogen Atoms, *J. Org. Chem.*, vol. 55, pp. 3364–3368 (1990).

Bradshaw, J.S. et al., A Simple Crab–Like Cyclization Procedure to Prepare Polyaza–Crowns and cyclams With One or Two Unsubstituted Macroring Nitrogen Atoms or With a Hydroxy Group, *J. Heterocyclic Chem.*, vol. 26, pp. 1431–1435 (1989).

Krakowiak, K.E. et al., Novel Syntheses of Monofunctionalized Triaza–Crowns and Cyclams With a Secondary Amine Group on a Side Chain, *Tetrahedron Letters*, vol. 30, No. 22, pp. 2897–2900 (1989).

Krakowiak, K.E. et al., Preparation and Structural Properities of Large–Cavity Peraza Macrocycles Containing Pyridine, Phenanthroline, or Piperazine Subcyclic Units, *J. Org. Chem.*, vol. 56, pp. 2675–2890 (1991).

Lindoy, L. F., The Chemistry of Macrocyclic Ligand Complexes, Cambridge University Press, p. 16–17 and 40–43 (1989).

MANGANESE COMPLEXES OF NITROGEN-CONTAINING MACROCYCLIC LIGANDS EFFECTIVE AS CATALYSTS FOR DISMUTATING SUPEROXIDE

This application is a Divisional of U.S. Ser. No. 08/080,732 filed Jun. 22, 1993, now pending, which is a continuation of U.S. Ser. No. 07/902,146 filed Jun. 26, 1992, now abandoned, which is a Continuation-in-part of U.S. Ser. No. 07/829,865 filed Feb. 3, 1992, now abandoned, which is a Continuation-in-part of U.S. Ser. No. 07/732,853 filed Jul. 19, 1991, now abanoned.

BACKGROUND OF THE INVENTION

1. Field of the Invention

The present invention relates to compounds effective as catalysts for dismutating superoxide and, more particularly, relates to manganese(II) or manganese(III) complexes of nitrogen-containing fifteen-membered macrocyclic ligands which catalytically dismutate superoxide.

2. Related Art

The enzyme superoxide dismutase catalyzes the conversion of superoxide into oxygen and hydrogen peroxide according to equation (1) (hereinafter referred to as dismutation). Reactive oxygen metabolites derived from superoxide are postulated to contribute to the tissue pathology in a number of $$O_2^-+O_2^-+2H+ \rightarrow O_2+H_2O_2 \qquad (1)$$

inflammatory diseases and disorders, such as reperfusion injury to the ischemic myocardium, inflammatory bowel disease, rheumatoid arthritis, osteoarthritis, atherosclerosis, hypertension, metastasis, psoriasis, organ transplant rejections, radiation-induced injury, asthma, influenza, stroke, burns and trauma. See, for example, Simic, M. G., et al, Oxygen Radicals in Biology and Medicine, Basic Life Sciences, Vol. 49, Plenum Press, New York and London, 1988; Weiss J. Cell. Biochem., 1991 Suppl. 15C, 216 Abstract C110 (1991); Petkau, A., Cancer Treat. Rev. 13, 17 (1986); McCord, J. Free Radicals Biol. Med., 2, 307 (1986); and Bannister, J. V. et al, Crit. Rev. Biochem., 22, 111 (1987).

It is also known that superoxide is involved in the breakdown of endothelium-derived vascular relaxing factor (EDRF), which has been identified as nitric oxide (NO), and that EDRF is protected from breakdown by superoxide dismutase. This suggests a central role for activated oxygen species derived from superoxide in the pathogenesis of vasospasm, thrombosis and atherosclerosis. See, for example, Gryglewski, R. J. et al., "Superoxide Anion is Involved in the Breakdown of Endothelium-derived Vascular Relaxing Factor", Nature, Vol. 320, pp. 454–56 (1986) and Palmer, R. M. J. et al., "Nitric Oxide Release Accounts for the Biological Activity of Endothelium Derived Relaxing Factor", Nature, Vol. 327, pp. 523–26 (1987).

Clinical trials and animal studies with natural, recombinant and modified superoxide dismutase enzymes have been completed or are ongoing to demonstrate the therapeutic efficacy of reducing superoxide levels in the disease states noted above. However, numerous problems have arisen with the use of the enzymes as potential therapeutic agents, including lack of oral activity, short half-lives in vivo, immunogenicity with nonhuman derived enzymes, and poor tissue distribution.

SUMMARY OF THE INVENTION

The present invention is directed to low molecular weight mimics of superoxide dismutase (SOD) useful as therapeutic agents for inflammatory disease states and disorders which are mediated, at least in part, by superoxide. The SOD mimics of the present invention are manganese(II) or manganese(III) complexes of nitrogen-containing fifteen-membered macrocyclic ligands.

DETAILED DESCRIPTION OF THE INVENTION

Figure 1:
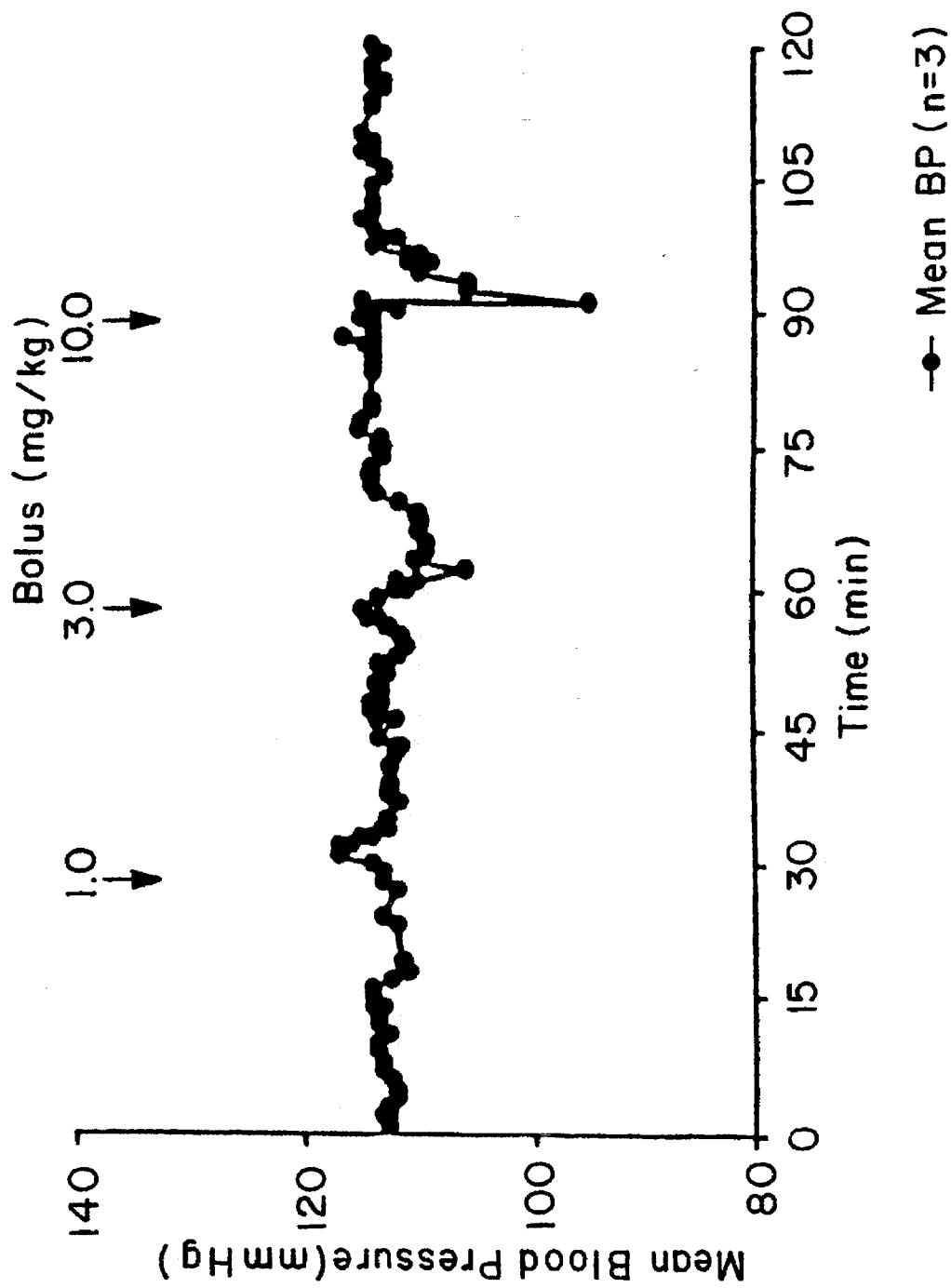
FIG. 1 is a plot demonstrating the effect of the manganese (II) complex of Example 1 on the mean blood pressure of rats as described in Example 47.

The present invention is directed to manganese(II) or manganese(III) complexes of nitrogen-containing fifteen-membered macrocyclic ligands which catalyze the conversion of superoxide into oxygen and hydrogen peroxide. These complexes can be represented by the formula:

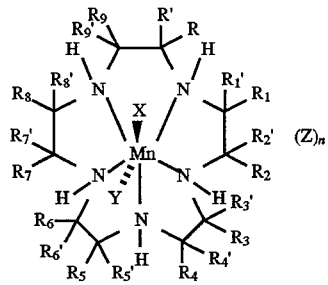

wherein R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently represents hydrogen, alkyl, alkenyl, alkynyl, cycloalkyl, cycloalkenyl, cycloalkyalkyl, cycloalkylcycloalkyl, cycloalkenylalkyl, alkylcycloalkyl, alkylcycloalkenyl, alkenylcycloalkyl, alkenylcycloalkenyl, heterocyclic, aryl and aralkyl radicals; $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached independently form a saturated, partially saturated or unsaturated cyclic having 3 to 20 carbon atoms; R or R'and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen as shown in the above formula, which nitrogen is also in the macrocyclic ligand or complex, and the R groups attached to the same carbon atoms of the macrocycle are absent; R and R', $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a saturated, partially saturated, or unsaturated ring structure having 3 to 20 carbon atoms; and one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ together with a different one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ which is attached to a different carbon atom in the macrocyclic ligand may be bound to form a strap represented by the formula

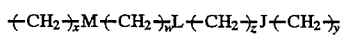

wherein w, x, y and z independently are integers from 0 to 10 and M, L and J are independently selected from the group consisting of alkyl, alkenyl, alkynyl, aryl, cycloalkyl, heteroaryl, alkaryl, alkheteroaryl, aza, amide, ammonium, oxa, thia, sulfonyl, sulfinyl, sulfonamide, phosphoryl, phosphinyl, phosphino, phosphonium, keto, ester, carbamate, urea, thiocarbonyl, borates, boranes, boraza, silyl, siloxy, silaza and combinations thereof; and combinations thereof. Thus, the complexes of the present invention can have any combinations of R groups, saturated, partially saturated or unsaturated cyclics, nitrogen containing heterocycles, saturated, partially saturated or unsaturated ring structures and straps as defined above.

The "R" groups attached to the carbon atoms of the macrocycle can be in the axial or equatorial position relative to the macrocycle. When the "R" group is other than hydrogen or when two adjacent "R" groups, i.e., on adjacent carbon atoms, together with the carbon atoms to which they are attached form a saturated, partially saturated or unsaturated cyclic or a nitrogen containing heterocycle, or when two R groups on the same carbon atom together with the carbon atom to which they are attached form a saturated, partially saturated or unsaturated ring structure, it is preferred that at least some of the "R" groups are in the equatorial position for reasons of improved activity and stability. This is particularly true when the complex contains more than one "R" group which is not hydrogen.

X, Y and Z represent suitable ligands or charge-neutralizing anions which are derived from any monodentate or polydentate coordinating ligand or ligand system or the corresponding anion thereof (for example benzoic acid or benzoate anion, phenol or phenoxide anion, alcohol or alkoxide anion). X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid (such as acetic acid, trifluoroacetic acid, oxalic acid), aryl carboxylic acid (such as benzoic acid, phthalic acid), urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate aryl thiocarbamate, alkyl aryl thiocarbamate, alkyl dithiocarbamate, aryl dithiocarbamate, alkyl aryl dithiocarbamate, bicarbonate, carbonate, perchlorate, chlorate, chlorite, hypochlorite, perbromate, bromate, bromite, hypobromite, tetrahalomanganate, tetrafluoroborate, hexafluorophosphate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or systems where one or more of X, Y and Z are independently attached to one or more of the "R" groups, wherein n is an integer from 0 to 3. The preferred ligands from which X, Y and Z are selected include halide, organic acid, nitrate and bicarbonate anions.

Currently, preferred compounds are those wherein at least one, preferably at least two, of the "R" groups represent alkyl, cycloalkylalkyl and aralkyl radicals and the remaining R groups represent hydrogen, a saturated, partially saturated or unsaturated cyclic, or a nitrogen containing heterocycle, those wherein at least one, preferably at least two, of $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, and $R_9$ or $R'_9$ and R or R' together with the carbon atoms to which they are attached represent a saturated, partially saturated or unsaturated cyclic having 3 to 20 carbon atoms and all the remaining "R" groups are hydrogen, nitrogen containing heterocycle or alkyl groups, and those wherein at least one, preferably at least two, of R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached are bound to form a nitrogen containing heterocycle having 2 to 20 carbon atoms and all the remaining "R" groups are independently selected from hydrogen, saturated, partially saturated or unsaturated cyclic or alkyl groups. As used herein, "R" groups means all of the R groups attached to the carbon atoms of the macrocycle, i.e. R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$. Examples of complexes of the invention include, but are not limited to, compounds having the formulas:

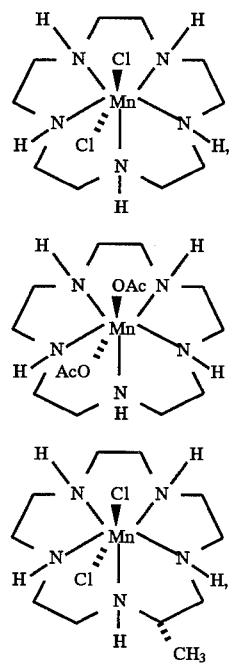

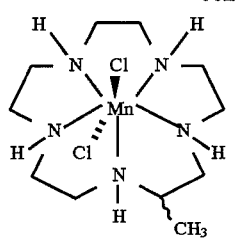
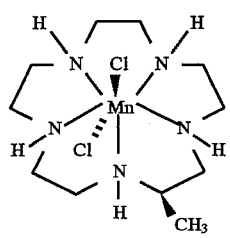
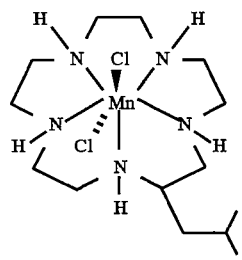
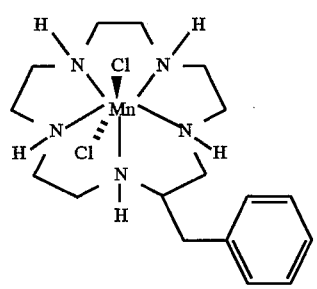
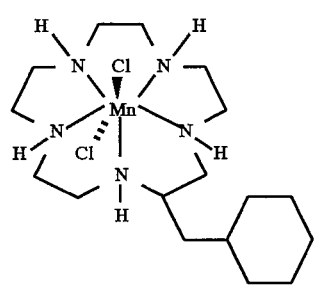
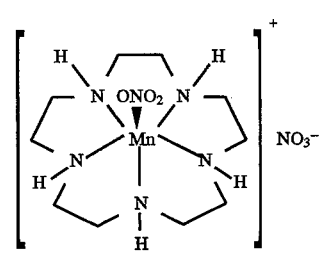
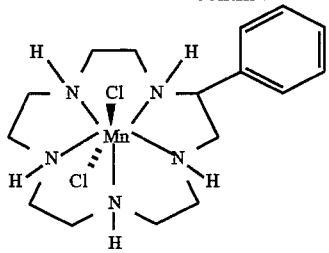
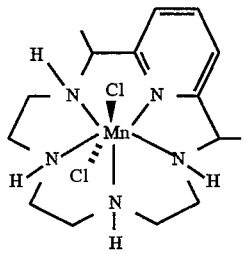
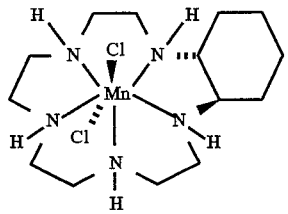
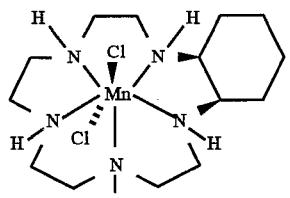
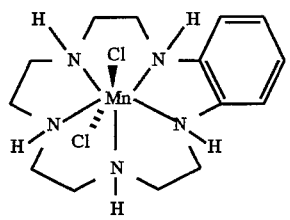
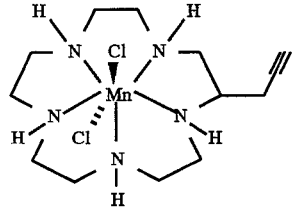
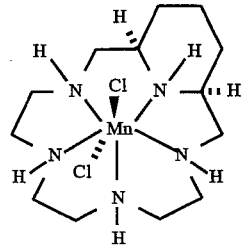

-continued
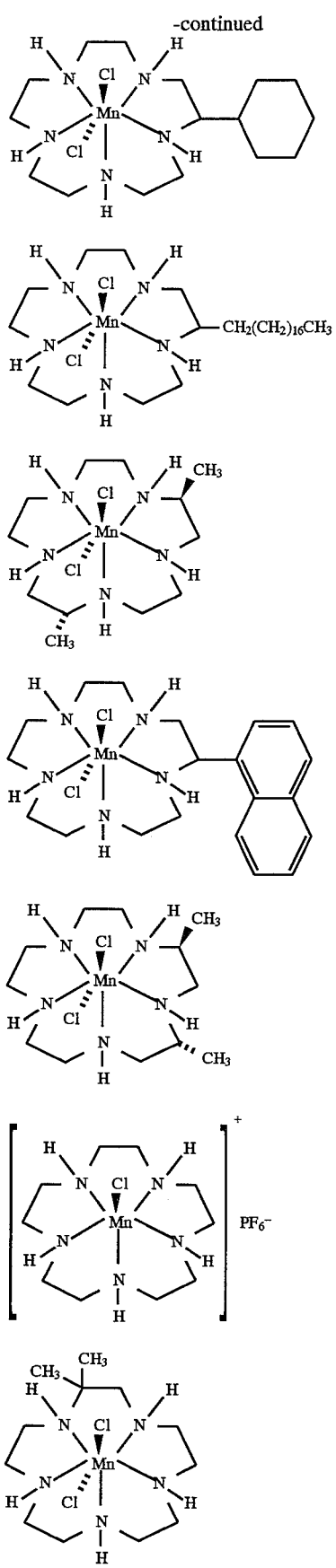
-continued
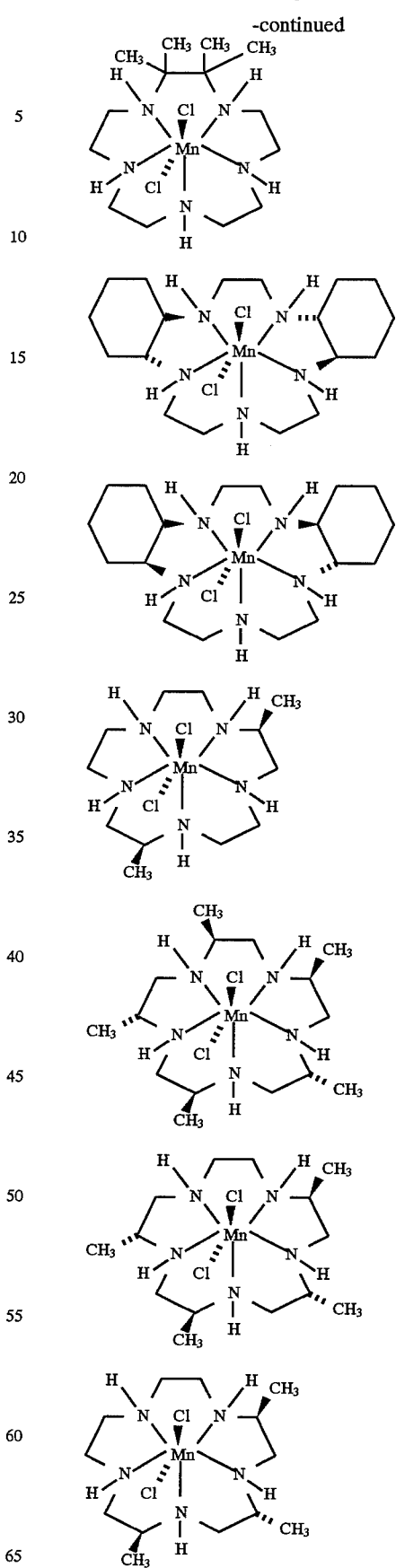

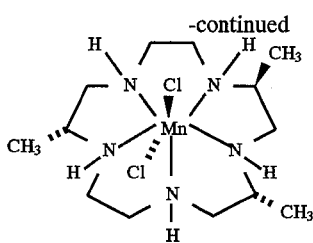

The commonly accepted mechanism of action of the manganese-based SOD enzymes involves the cycling of the manganese center between the two oxidation states (II,III). See J. V. Bannister, W. H. Bannister, and G. Rotilio, Crit. Rev. Biochem., 22, 111–180 (1987).

$$Mn(II) + HO_2 \cdot \rightarrow Mn(III) + HO_2^- \quad (1)$$

$$Mn(III) + O_2^- \rightarrow Mn(II) + O_2 \quad (2)$$

The formal redox potentials for the $O_2/O_2^-$ and $HO_2 \cdot /H_2O_2$ couples at pH=7 are −0.33 v and 0.87 v, respectively. See A. E. G. Cass, in Metalloproteins: Part 1, Metal Proteins with Redox Roles, ed. P. Harrison, P. 121. Verlag Chemie (Weinheim, GDR) (1985). For the above disclosed mechanism, these potentials require that a putative SOD catalyst be able to rapidly undergo oxidation state changes in the range of −0.33 v to 0.87 v.

The complexes derived from Mn(II) and the general class of C-substituted [15]aneN$_5$ ligands described herein have all been characterized using cyclic voltammetry to measure their redox potential. The C-substituted complexes described herein have reversible oxidations of about +0.7 v (SHE). Coulometry shows that this oxidation is a one-electron process; namely it is the oxidation of the Mn(II) complex to the Mn(III) complex. Thus, for these complexes to function as SOD catalysts, the Mn(III) oxidation state is involved in the catalytic cycle. This means that the Mn(III) complexes of all these ligands are equally competent as SOD catalysts, since it does not matter which form (Mn(II) or Mn(III)) is present when superoxide is present because superoxide will simply reduce Mn(III) to Mn(II) liberating oxygen.

As utilized herein, the term "alkyl", alone or in combination, means a straight-chain or branched-chain alkyl radical containing from 1 to about 22 carbon atoms, preferably from about 1 to about 18 carbon atoms, and most preferably from about 1 to about 12 carbon atoms. Examples of such radicals include, but are not limited to, methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl. The term "alkenyl", alone or in combination, means an alkyl radical having one or more double bonds. Examples of such alkenyl radicals include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans- 9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl. The term "alkynyl", alone or in combination, means an alkyl radical having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl. The term "cycloalkyl", alone or in combination means a cycloalkyl radical containing from 3 to about 10, preferably from 3 to about 8, and most preferably from 3 to about 6, carbon atoms. Examples of such cycloalkyl radicals include, but are not limited to, cyclopropyl, cyclobutyl, cyclopentyl, cyclohexyl, cycloheptyl, cyclooctyl, and per-hydronaphthyl. The term "cycloalkylalkyl" means an alkyl radical as defined above which is substituted by a cycloalkyl radical as defined above. Examples of cycloalkylalkyl radicals include, but are not limited to, cyclohexylmethyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl. The term "cycloalkylcycloalkyl" means a cycloalkyl radical as defined above which is substituted by another cycloalkyl radical as defined above. Examples of cycloalkylcycloalkyl radicals include, but are not limited to, cyclohexylcyclopentyl and cyclohexylcyclohexyl. The term "cycloalkenyl", alone or in combination, means a cycloalkyl radical having one or more double bonds. Examples of cycloalkenyl radicals include, but are not limited to, cyclopentenyl, cyclohexenyl, cyclooctenyl, cyclopentadienyl, cyclohexadienyl and cyclooctadienyl. The term "cycloalkenylalkyl" means an alkyl radical as defined above which is substituted by a cycloalkenyl radical as defined above. Examples of cycloalkenylalkyl radicals include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl) pentyl, 1-(1-cyclopenten-1-yl)hexyl, 6-(1-cyclohexen-1-yl) hexyl, 1-(1-cyclopenten-1-yl)nonyl and 1-(1-cyclohexen-1-yl)nonyl. The terms "alkylcycloalkyl" and "alkenylcycloalkyl" mean a cycloalkyl radical as defined above which is substituted by an alkyl or alkenyl radical as defined above. Examples of alkylcycloalkyl and alkenylcycloalkyl radicals include, but are not limited to, 2-ethylcyclobutyl, 1-methylcyclopentyl, 1-hexylcyclopentyl, 1-methylcyclohexyl, 1-(9-octadecenyl) cyclopentyl and 1-(9-octadecenyl)cyclohexyl. The terms "alkylcycloalkenyl" and "alkenylcycloalkenyl" means a cycloalkenyl radical as defined above which is substituted by an alkyl or alkenyl radical as defined above. Examples of alkylcycloalkenyl and alkenylcycloalkenyl radicals include, but are not limited to, 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl- The term "aryl", alone or in combination, means a phenyl or naphthyl radical which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tertbutoxy) phenyl, 4-fluorophenyl, 4-chlorophenyl, 4-hydroxyphenyl, 1-naphthyl, 2-naphthyl, and the like. The term "aralkyl", alone or in combination, means an alkyl or cycloalkyl radical as defined above in which one hydrogen atom is replaced by an aryl radical as defined above, such as benzyl, 2-phenylethyl, and the like. The term "heterocyclic" means ring structures containing at least one other kind of atom, in addition to carbon, in the ring. The most common of the other kinds of atoms include nitrogen, oxygen and sulfur. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. The term "saturated, partially saturated or unsaturated cyclic" means fused ring structures in which 2 carbons of the ring are also part of the fifteen-membered macrocyclic ligand. The ring structure can contain 3 to 20 carbon atoms, preferably 5 to 10 carbon atoms, and can also contain one or more other kinds of atoms in addition to carbon. The most common of the other kinds of atoms include nitrogen, oxygen and sulfur. The ring structure can also contain more than one ring. The term "saturated, partially saturated or unsaturated ring structure" means a ring structure in which one carbon of the ring is also part of the fifteen-membered macrocyclic ligand. The ring structure can contain 3 to 20, preferably 5 to 10, carbon atoms and can also contain nitrogen, oxygen and/or sulfur atoms. The term "nitrogen containing heterocycle" means ring structures in which 2 carbons and a nitrogen of the ring are also part of the fifteen-membered macrocyclic ligand. The ring structure can contain 2 to 20, preferably 4 to 10, carbon atoms, can be partially or fully unsaturated or saturated and can also contain nitrogen, oxygen and/or sulfur atoms in the portion of the ring which is not also part of the fifteen-membered macrocyclic ligand. The term "organic acid anion" refers to carboxylic acid anions having from about 1 to about 18 carbon atoms. The term "halide" means chloride or bromide.

The macrocyclic ligands useful in the complex of the present invention wherein R is H can be prepared according to the general synthetic scheme A set forth below utilizing methods known in the art for preparation of certain intermediates and certain ligands. See, for example, Richman et al., *J. Am. Chem. Soc.*, 96, 2268 (1974); Atkins et al. *Org. Synth.*, 58, 86 (1978); and EP 287 465. Thus a triazaalkane is tosylated in a suitable solvent system to produce the corresponding tris(N-tosyl) derivative. Such derivative is then treated with a suitable base to produce the corresponding disulfonamide anion. The disulfonamide anion is then reacted with a di-O-tosylated di-N-tosylated diazaalkane diol to produce the corresponding pentatosylpentaazacycloalkane. The tosyl groups are then removed and the resulting compound is reacted with a manganese(II) compound under essentially anhydrous and anaerobic conditions to form the corresponding manganese(II) pentaazacycloalkane complex.

The macrocyclic ligands useful in the complexes of the present invention can also be prepared according to the general procedure shown in Scheme B set forth below. Thus, an amino acid amide, which is the corresponding amide derivative of a naturally or non-naturally occurring α-amino acid, is reduced to form the corresponding substituted ethylenediamine. Such amino acid amide can be the amide derivative of any one of many well known amino acids. Preferred amino acid amides are those represented by the formula:

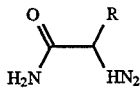

wherein R is as previously defined. Most preferred are those wherein R represents hydrogen, alkyl, cycloalkylalkyl, and aralkyl radicals. The diamine is then tosylated to produce the di-N-tosyl derivative which is reacted with a di-O-tosylated tris-N-tosylated triazaalkane diol to produce the corresponding substituted N-pentatosylpentaazacycloalkane. The tosyl groups are then removed and the resulting compound is reacted with a manganese(II) compound under essentially anhydrous and anaerobic conditions to form the corresponding substituted manganese(II) pentaazacycloalkane complex. Those ligands wherein R is other than hydrogen and methyl are novel compounds.

The macrocyclic ligands useful in the complexes of the present invention, wherein $R_1$, $R'_1$, $R_3$, $R'_3$, $R_5$, $R'_5$, $R_7$, $R'_7$, $R_9$ and $R'_9$ can be H or any functionality as previously described, can be prepared according to the general peptide method shown in Scheme C set forth below. The procedure for preparing the cyclic peptide precursors from the corresponding linear peptides are the same or significant modifications of methods known in the art. See, for example, Veber, D. F. et al., J. Org. Chem., 44, 3101 (1979). The general method outlined in Scheme C below is an example utilizing the sequential solution-phase preparation of the functionalized linear pentapeptide from N-terminus to C-terminus. Alternatively, the reaction sequence to prepare the linear pentapeptide can be carried out by solid-phase preparation utilizing methods known in the art. The reaction sequence could be conducted from C-terminus terminus to N-terminus and by convergent approaches such as the coupling of di- and tri-peptides as needed. Thus a Boc-protected amino acid is coupled with an amino acid ester using standard peptide coupling reagents. The new Boc-dipeptide ester is then saponified to the free acid which is coupled again to another amino acid ester. The resulting Boc-tri-peptide ester is again saponified and this method is continued until the Boc-protected pentapeptide free acid has been prepared. The Boc protecting group is removed under standard conditions and the resulting pentapeptide or salt thereof is converted to the cyclic pentapeptide. The cyclic pentapeptide is then reduced to the pentaazacyclopentadecane with lithium aluminum hydride or borane. The final ligand is then reacted with a manganese(II) compound under essentially anaerobic conditions to form the corresponding manganese (II) pentaazacyclopentadecane complex.

Scheme C was utilized for the synthesis of the complexes of Examples 29, 32–34, 40 and 41.

The R groups in the macrocycles produced by the cyclic peptide route, i.e., $R_1$, $R'_1$, $R_3$, $R'_3$, $R_5$, $R'_5$, $R_7$, $R'_7$, $R_9$ and $R'_9$, could be derived from the D or L forms of the amino acids Alanine, Aspartic acid, Arginine, Asparagine, Cysteine, Glycine, Glutamic acid, Glutamine, Histidine, Isoleucine, Leucine, Lysine, Methionine, Proline, Phenylalanine, Serine, Tryptophan, Threonine, Tyrosine, Valine and/or the R groups of unnatural α-amino acids such as alkyl, ethyl, butyl, tert-butyl, cycloalkyl, phenyl, alkenyl, allyl, alkynyl, aryl, heteroaryl, polycycloalkyl, polycycloaryl, polycycloheteroaryl, imines, aminoalkyl, hydroxyalkyl, hydroxyl, phenol, amine oxides, thioalkyl, carboalkoxyalkyl, carboxylic acids and their derivatives, keto, ether, aidehyde, amine, nitrile, halo, thiol, sulfoxide, sulfone, sulfonic acid, sulfide, disulfide, phosphonic acid, phosphinic acid, phosphine oxides, sulfonamides, amides, amino acids, peptides, proteins, carbohydrates, nucleic acids, fatty acids, lipids, nitro, hydroxylamines, hydroxamic acids, thiocarbonyls, borates, boranes, boraza, silyl, siloxy, silaza, and combinations thereof.

The complexes of the present invention, wherein $R_9$, and $R_2$ are alkyl, and $R_3$, $R'_3$, $R_4$, $R'_4$, $R_5$, $R'_5$, $R_6$, $R'_6$, $R_7$, $R'_7$, $R_8$ and $R'_8$ can be alkyl, arylalkyl or cycloalkylalkyl and R or R' and $R_1$ or $R'_1$ together with the carbon atoms they are attached to are bound to form a nitrogen containing heterocycle, can also be prepared according to the general procedure shown in Scheme D set forth below utilizing methods known in the art for preparing the manganese(II) pentaazabicyclo[12.3.1]octadecapentaene complex precursor. See, for example, Alexander et al., Inorg. Nucl. Chem. Lett., 6, 445 (1970). Thus a 2,6-diketopyridine is condensed with triethylene tetraamine in the presence of a manganese (II) compound to produce the manganese(II) pentaazabicyclo[12.3.1]octadecapentaene complex. The manganese(II) pentaazabicyclo[12.3.1]octadecapentaene complex is hydrogenated with 5% rhodium on carbon at a pressure of 1000 psi to give the corresponding manganese (II) pentaazabicyclo[12.3.1]octadecatriene complex.

Scheme D was utilized for the synthesis of the complex of Example 39.

The macrocyclic ligands useful in the complexes of the present invention can also be prepared by the diacid dichloride route shown in Scheme E set forth below. Thus, a triazaalkane is tosylated in a suitable solvent system to produce the corresponding tris(N-tosyl) derivative. Such a derivative is treated with a suitable base to produce the corresponding disulfonamide anion. The disulfonamide anion is dialkylated with a suitable electrophile to produce a derivative of a dicarboxylic acid. This derivative of a dicarboxylic acid is treated to produce the dicarboxylic acid, which is then treated with a suitable reagent to form the diacid dichloride. The desired vicinal diamine is obtained in any of several ways. One way which is useful is the preparation from an aldehyde by reaction with cyanide in the presence of ammonium chloride followed by treatment with acid to produce the alpha ammonium nitrile. The latter compound is reduced in the presence of acid and then treated with a suitable base to produce the vicinal diamine. Condensation of the diacid dichloride with the vicinal diamine in the presence of a suitable base forms the tris(tosyl)diamide macrocycle. The tosyl groups are removed and the amides are reduced and the resulting compound is reacted with a manganese (II) compound under essentially anhydrous and anaerobic conditions to form the corresponding substituted pentaazacycloalkane manganese (II) complex.

Scheme E was utilized for the synthesis of the complexes of Examples 28, 30 and 35–37.

The vicinal diamines have been prepared by the route shown (known as the Strecker synthesis) and vicinal diamines were purchased when commercially available. Any method of vicinal diamine preparation could be used.

The macrocyclic ligands useful in the complexes of the present invention can also be prepared by the pyridine diamide route shown in Scheme F as set forth below. Thus, a polyamine, such as a tetraaza compound, containing two primary amines is condensed with dimethyl 2,6-pyridine dicarboxylate by heating in an appropriate solvent, e.g., methanol, to produce a macrocycle incorporating the pyridine ring as the 2,6-dicarboxamide. The pyridine ring in the macrocycle is reduced to the corresponding piperidine ring in the macrocycle, and then the diamides are reduced and the resulting compound is reacted with a manganese (II) compound under essentially anhydrous and anaerobic conditions to form the corresponding substituted pentaazacycloalkane manganese (II) complex.

Scheme F was utilized for the synthesis of the complex of Example 38.

The macrocyclic ligands useful in the complexes of the present invention can also be prepared by the bis (haloacetamide) route shown in Scheme G set forth below. Thus a triazaalkane is tosylated in a suitable solvent system to produce the corresponding tris(N-tosyl) derivative. Such a derivative is treated with a suitable base to produce the corresponding disulfonamide anion. A bis(haloacetamide), e.g., a bis(chloroacetamide), of a vicinal diamine is prepared by reaction of the diamine with an excess of haloacetyl halide, e.g., chloroacetyl chloride, in the presence of a base. The disulfonamide anion of the tris(N-tosyl) triazaalkane is then reacted with the bis(chloroacetamide) of the diamine to produce the substituted tris(N-tosyl)diamide macrocycle. The tosyl groups are removed and the amides are reduced and the resulting compound is reacted with a manganese (II) compound under essentially anhydrous and anaerobic conditions to form the corresponding substituted pentaazacycloalkane manganese (II) complex.

Scheme G is an alternative synthetic route to the complex of Example 35.

SCHEME A

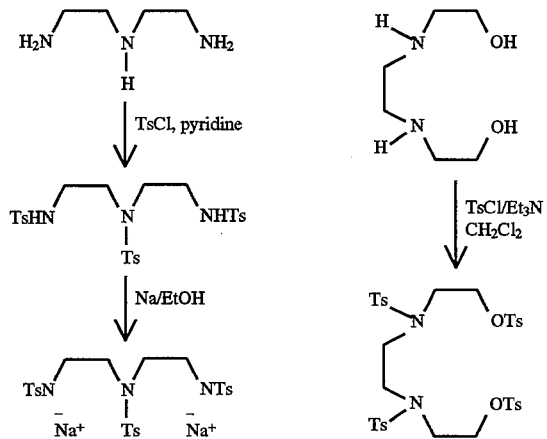

-continued
SCHEME A
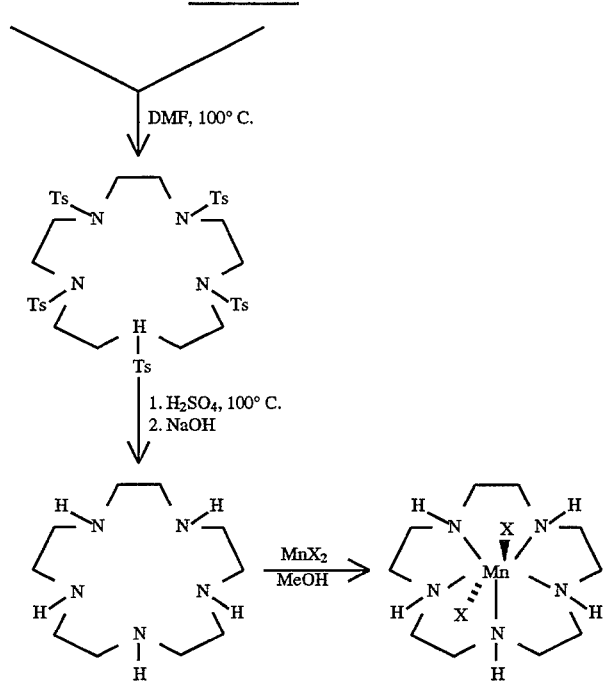
SCHEME B
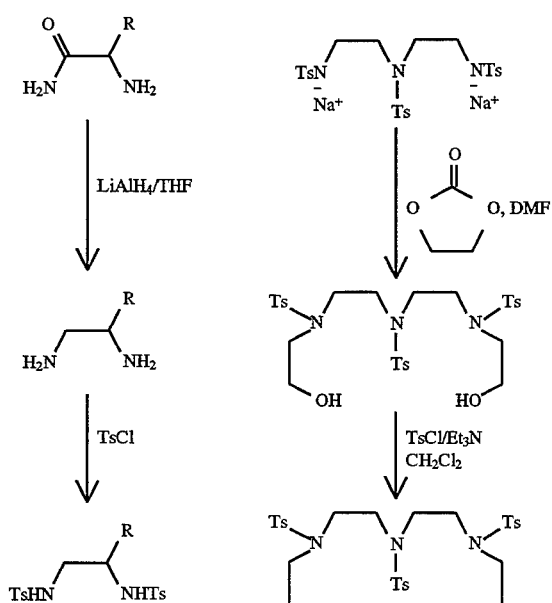
-continued
SCHEME B
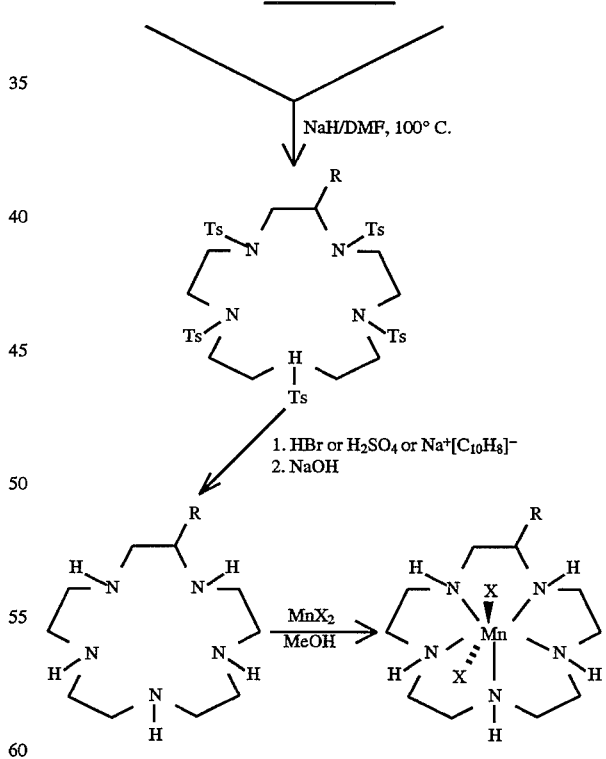

SCHEME C
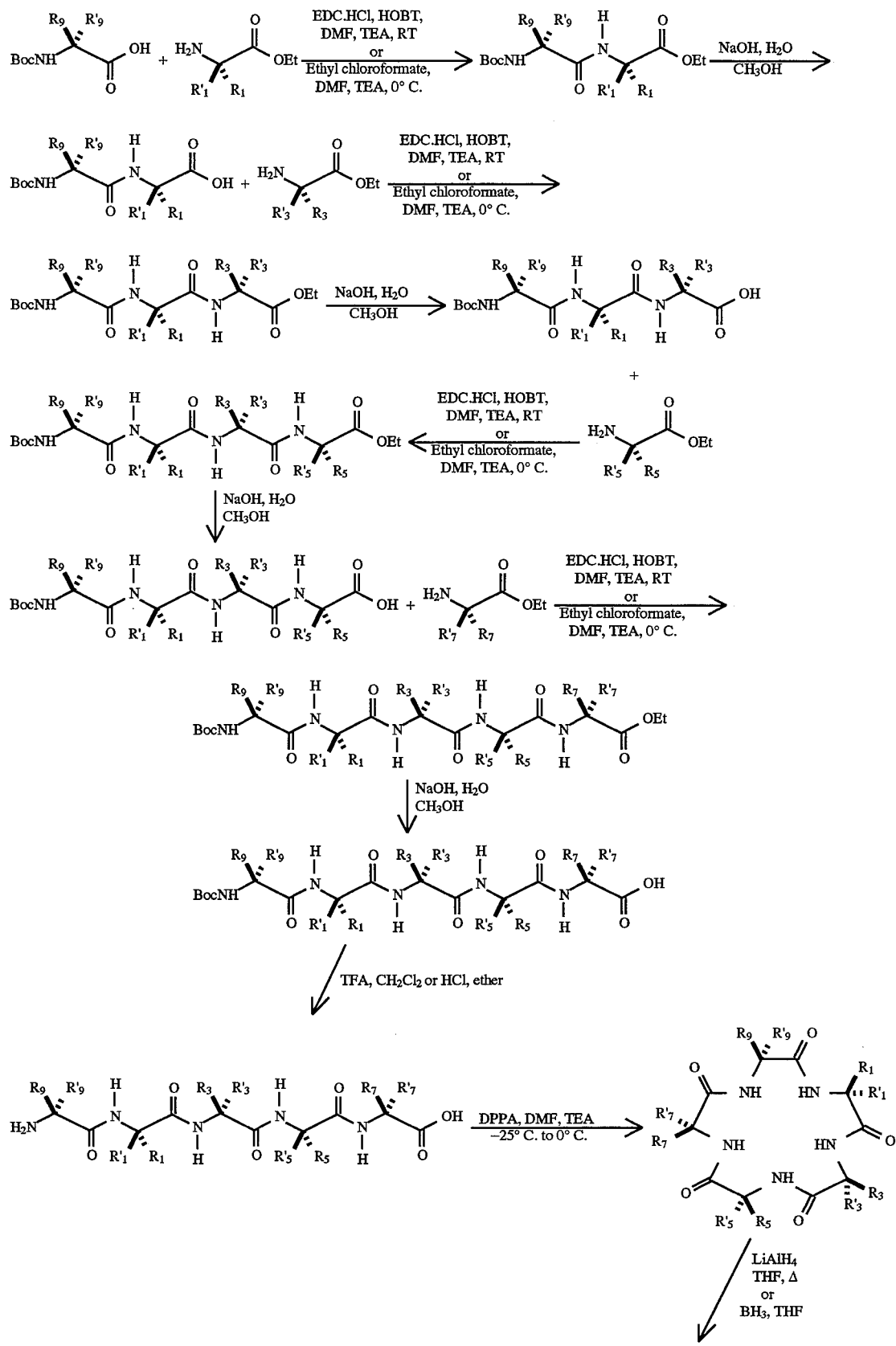

-continued
SCHEME C
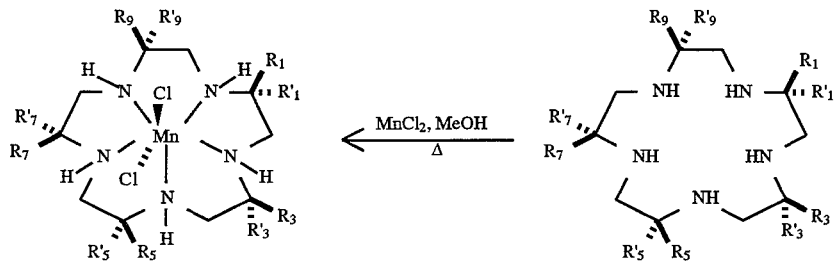
SCHEME D
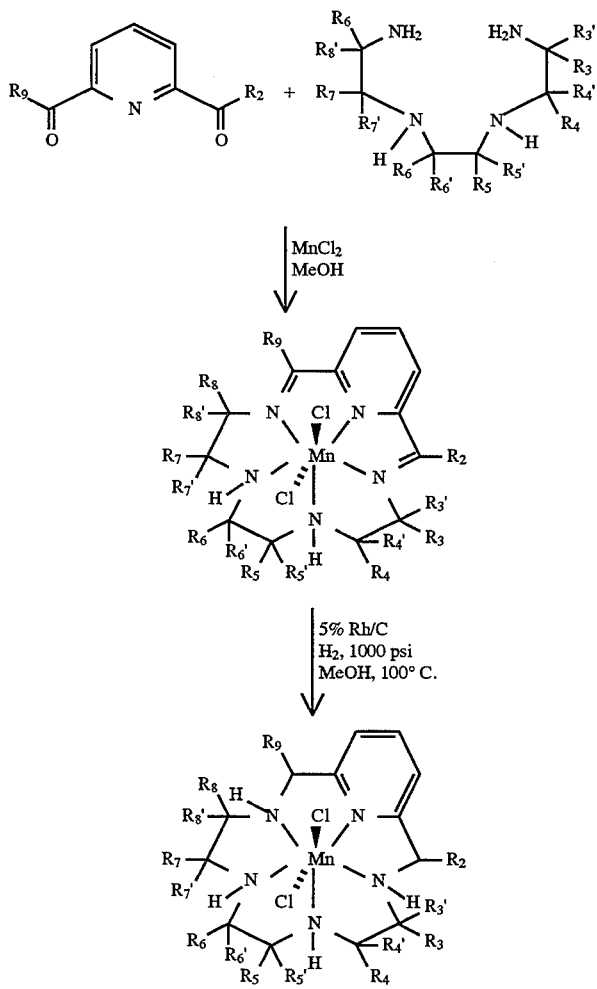

SCHEME E
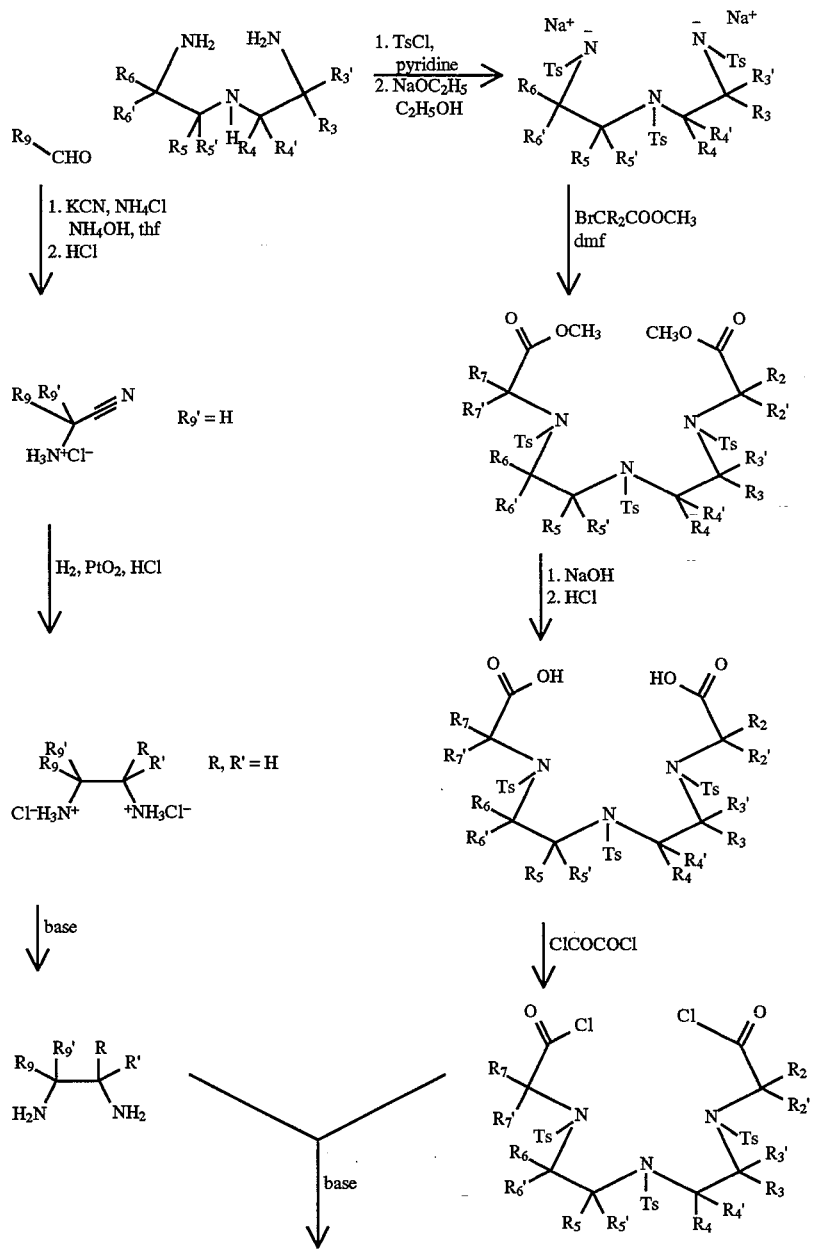

5,637,578
-continued
SCHEME E
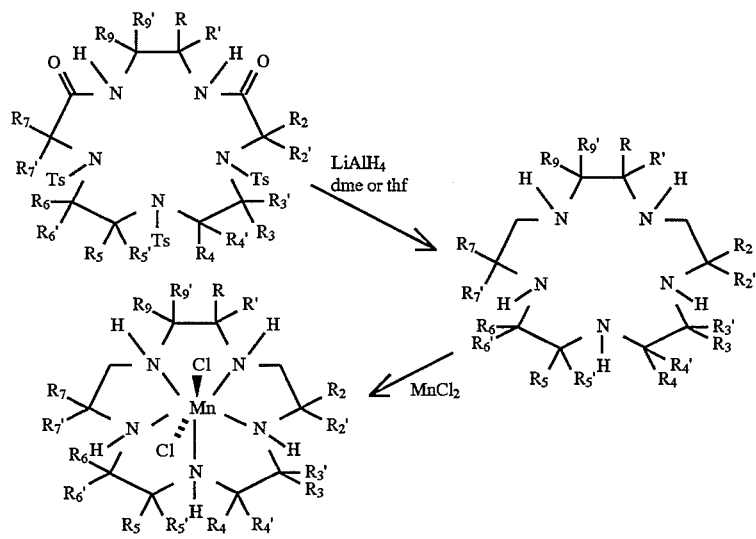
SCHEME F
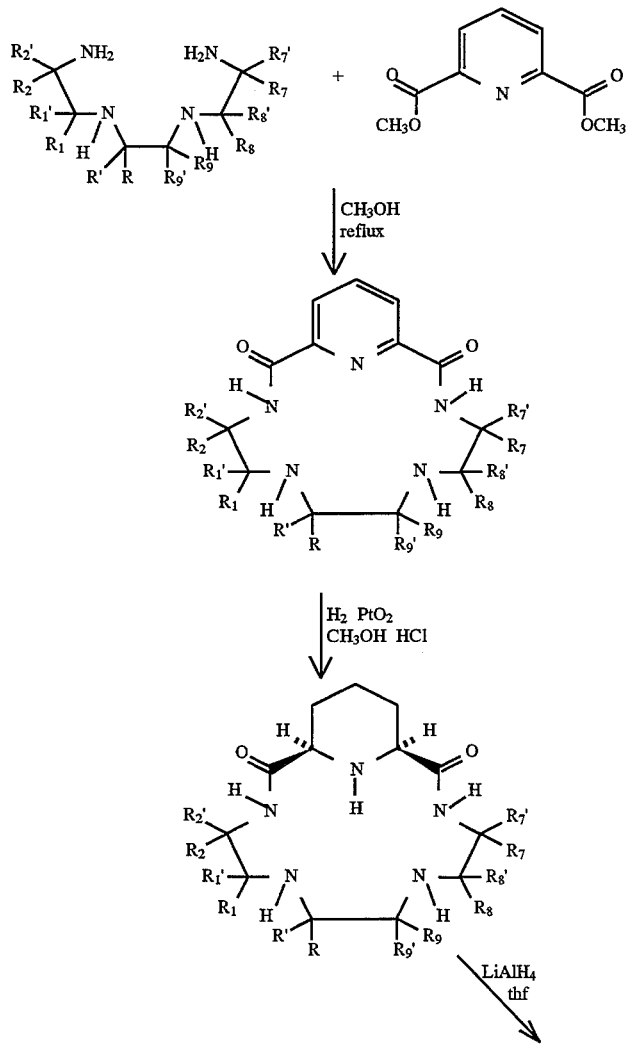

-continued
SCHEME F
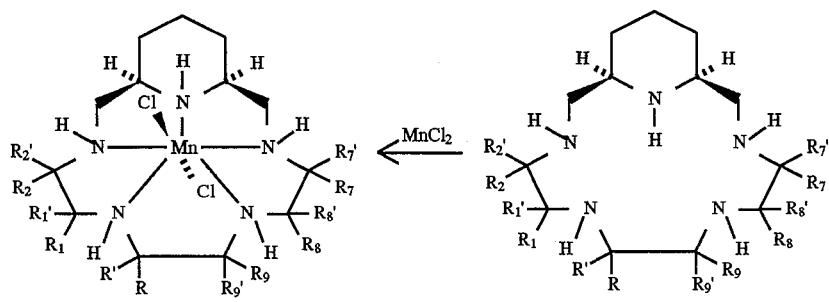
SCHEME G
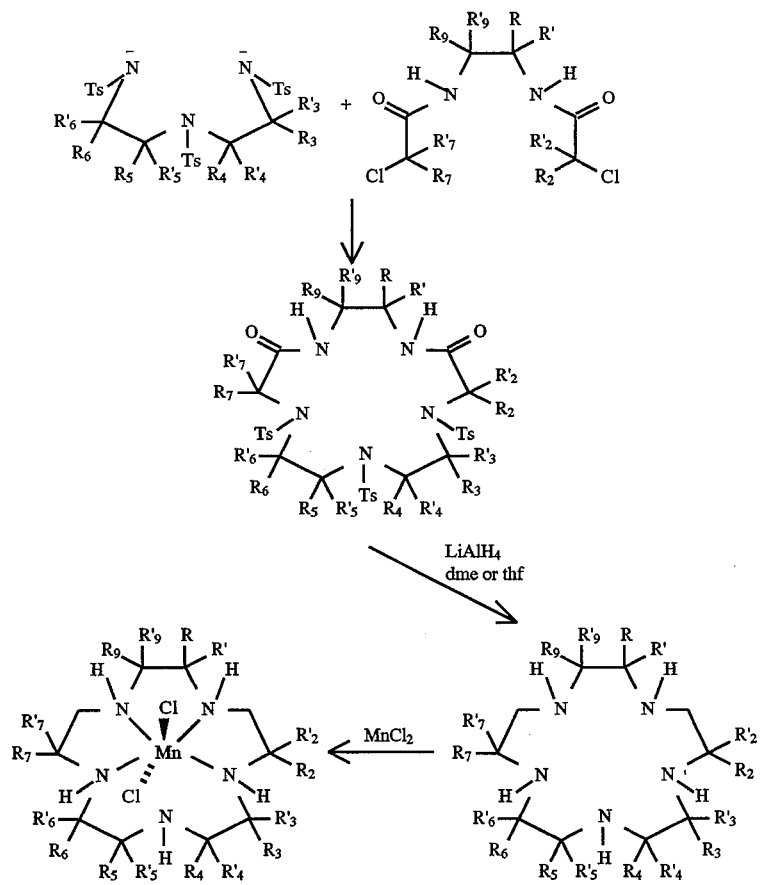
The macrocyclic ligands useful in the preparation of complexes of the present invention containing a strap can be prepared according to the following example shown in Scheme H, which is similar to Scheme C, and Scheme I, which is similar to Scheme E.

SCHEME H
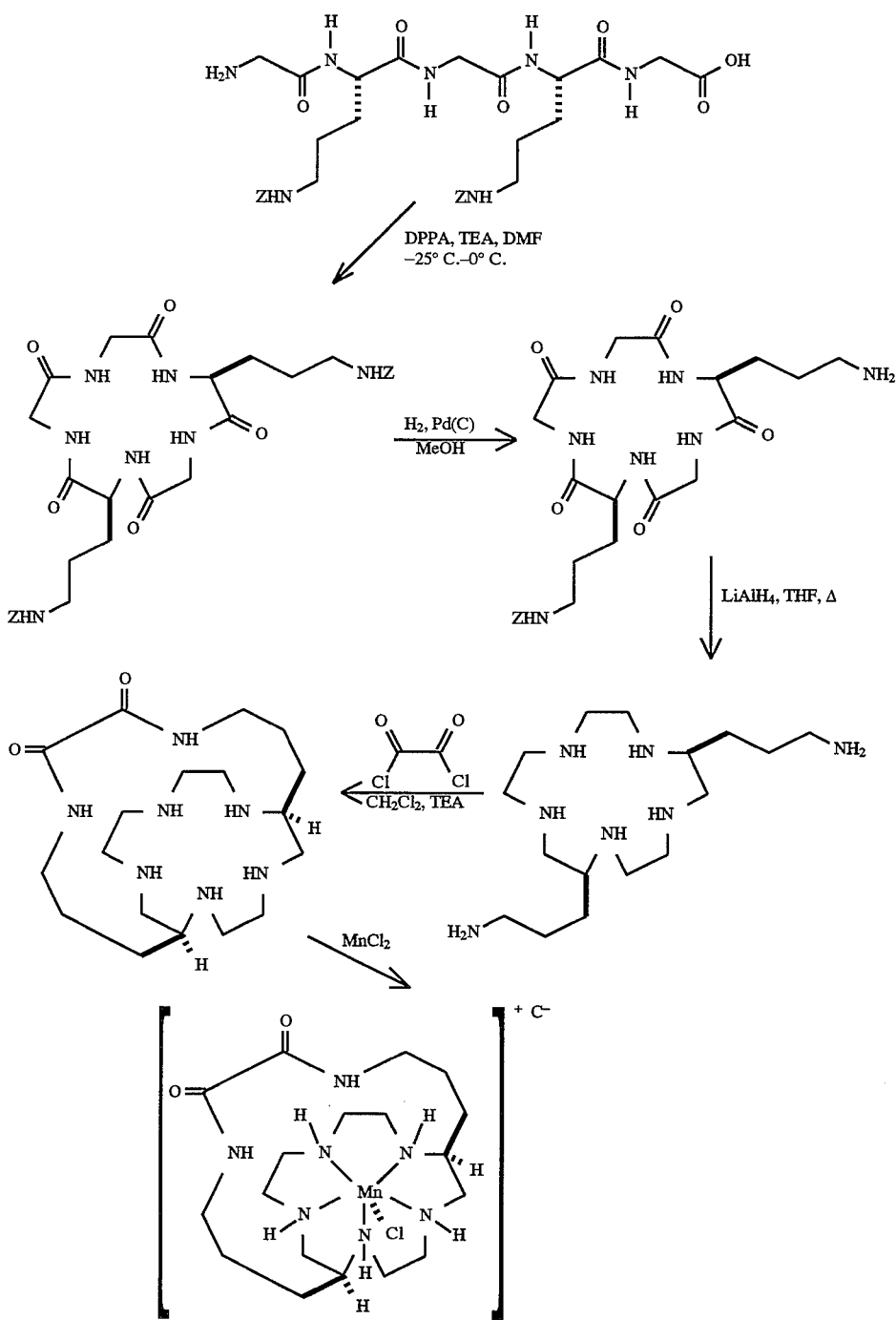

SCHEME I

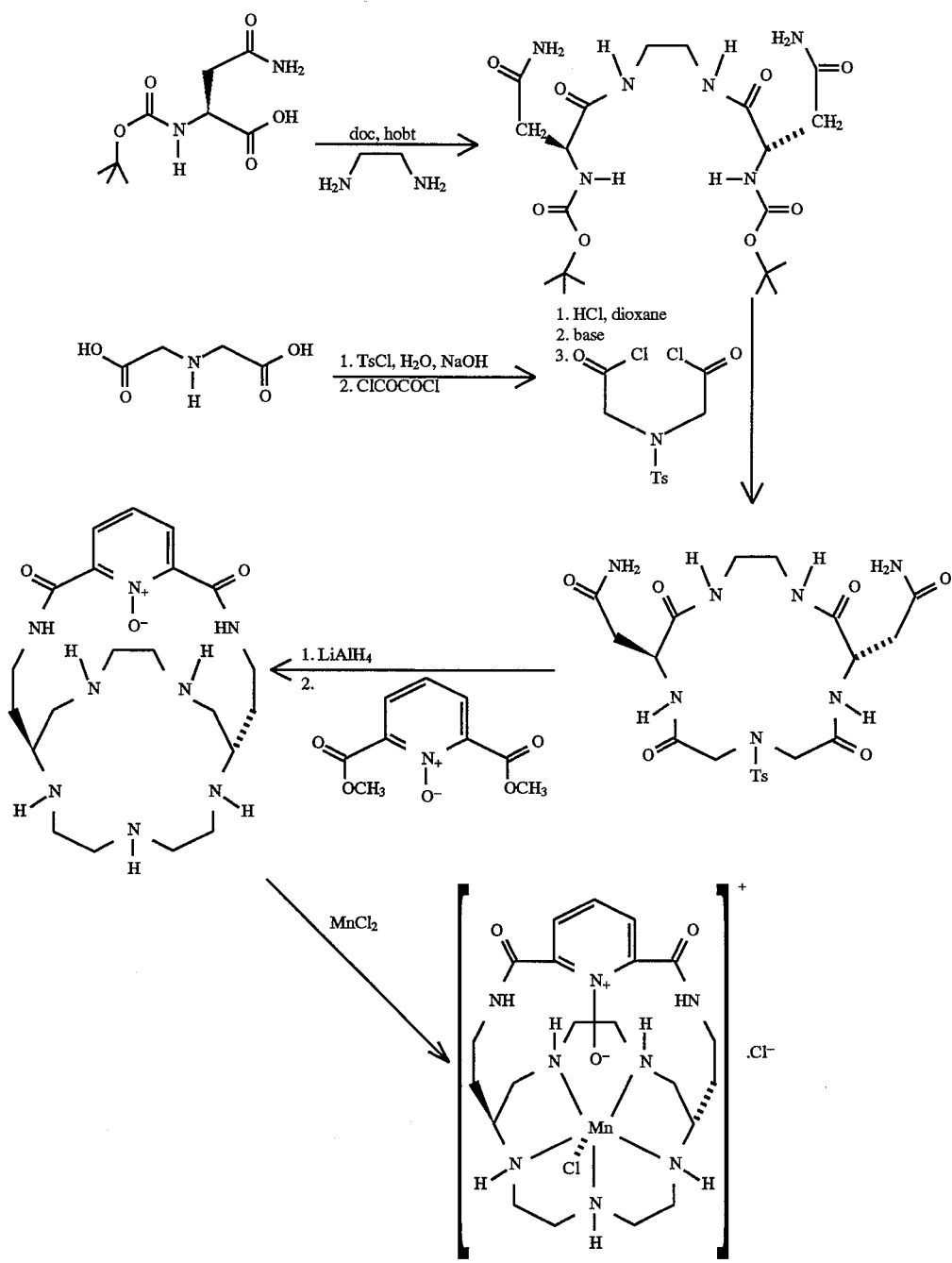

The pentaazamacrocycles of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting one or more secondary amine group(s) of the compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure ligand. The optically active compounds of the invention can likewise be obtained by utilizing optically active starting materials, such as natural amino acids.

The compounds or complexes of the present invention are novel and can be utilized to treat numerous inflammatory disease states and disorders. For example, reperfusion injury to an ischemic organ, e.g., reperfusion injury to the ischemic myocardium, inflammatory bowel disease, rheumatoid arthritis, osteoarthritis, hypertension, psoriasis, organ transplant rejections, organ preservation, impotence, radiation-induced injury, asthma, atherosclerosis, thrombosis, platelet aggregation, metastasis, influenza, stroke, burns, trauma, acute pancreatitis, pyelonephritis, hepatitis, autoimmune diseases, insulin-dependent diabetes mellitus, disseminated intravascular coagulation, fatty embolism, adult and infantile respiratory distress, carcinogenesis and hemorrhages in neonates.

Activity of the compounds or complexes of the present invention for catalyzing the dismutation of superoxide can be demonstrated using the stopped-flow kinetic analysis technique as described in Riley, D. P., Rivers, W. J. and Weiss, R. H., "Stopped-Flow Kinetic Analysis for Monitoring Superoxide Decay in Aqueous Systems," *Anal. Biochem.*, 196, 344–349 (1991), which is incorporated by reference herein. Stopped-flow kinetic analysis is an accurate and direct method for quantitatively monitoring the decay rates of superoxide in water. The stopped-flow kinetic analysis is suitable for screening compounds for SOD activity and activity of the compounds or complexes of the present invention, as shown by stopped-flow analysis, correlate to treating the above disease states and disorders.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, granules and gels. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they. can also be used in combination with one or more compounds which are known to be effective against the specific disease state that one is targeting for treatment.

Contemplated equivalents of the general formulas set forth above for the compounds and derivatives as well as the intermediates are compounds otherwise corresponding thereto and having the same general properties such as tautomers of the compounds and such as wherein one or more of the various R groups are simple variations of the substituents as defined therein, e.g., wherein R is a higher alkyl group than that indicated, or where the tosyl groups are other nitrogen or oxygen protecting groups or wherein the O-tosyl is a halide. Anions having a charge other than 1, e.g., carbonate, phosphate, and hydrogen phosphate, can be used instead of anions having a charge of 1, so long as they do not adversely affect the overall activity of the complex. However, using anions having a charge other than 1 will result in a slight modification of the general formula for the complex set forth above. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure. Further, it is contemplated that manganese(III) complexes will be equivalent to the subject manganese(II) complexes.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

All reagents were used as received without purification unless otherwise indicated. All NMR spectra were obtained on a Varian VXR-300 or VXR-400 nuclear magnetic resonance spectrometer. Qualitative and quantitative mass spectroscopy was run on a Finnigan MAT90, a Finnigan 4500 and a VG40-250T using m-nitrobenzyl alcohol(NBA) or m-nitrobenzyl alcohol/LiCl (NBA+Li). Melting points (mp) are uncorrected.

The following abbreviations relating to amino acids and their protective groups are in accordance with the recommendation by IUPAC-IUB Commission on Biochemical Nomenclature (Biochemistry, 11, 1726 (1972)) and common usage.

| | |
|---|---|
| Ala | L-Alanine |
| DAla | D-Alanine |
| Gly | Glycine |
| Ppg | Propargylglycine |
| Tyr | L-Tyrosine |
| Bzl | Benzyl |
| Boc | tert-Butoxycarbonyl |
| Et | Ethyl |
| TFA | Trifluoroacetate |
| DMF | Dimethylformamide |
| HOBT.H$_2$O | 1-Hydroxy-(1H)-benzotriazole monohydrate |
| EDC.HCl | 1-(3-Dimethylaminopropyl)-3-ethylcarbodiimide hydrochloride |
| TEA | Triethylamine |
| DMSO | Dimethylsulfoxide |
| THF | Tetrahydrofuran |
| DPPA | Diphenylphosphoryl azide |
| DMPU | Dimethylpropyleneurea |
| c | concentration, g/cc |
| DME | 1,2-Dimethoxyethane |

EXAMPLE 1

A. Synthesis of 1,4,7-Tris(p-toluenesulfonyl)-1,4,7-triazaheptane

This compound was synthesized following the procedure of Atkins, T. J.; Richman, J. E.; and Oettle, W. F.; *Org. Synth.*, 58, 86–98 (1978). To a stirred solution of p-toluenesulfonyl chloride (618 g, 3.24 mole) in pyridine (1500 ml) at 0°C. was added a solution of 1,4,7-triazaheptane (95.5 g, 0.926 mole) in pyridine (150 ml) under a dry argon atmosphere, maintaining the temperature<50 C. The addition required 30 minutes. After the mixture was allowed to cool to room temperature slowly while stirring for 3 h, H$_2$O (2 l) was slowly added to the cooled (ice bath) mixture. The heavy white precipitate which formed was filtered and washed-thoroughly with H$_2$O. The pale yellow solid was dissolved in DMF (3 l) and 0.1N HCl (4 l) was slowly added at 5° C. The slurry was filtered and the pale yellow solid was washed thoroughly with H$_2$O and dried in vacuo to give 486 g (93% yield) of the product: mp 180°–1° C.; $^1$H NMR(DMSO-d$_6$) δ2.39 (s, 3H), 2.40 (s, 6H), 2.84 (m, 4H), 3.04 (t, J=6.9 Hz, 4H) 7.40 (d, J=8.1 Hz, 4H), 7.59 (d, J=8.3 Hz, 2H), 7.67 (m, 6H).

B. Synthesis of 1,4,7-Tris(p-toluenesulfonyl)-1,4,7-triazaheptane-1,7-disodium Salt This compound was synthesized following the procedure of Atkins, T. J.; Richman, J. E., and Oettle, W. F.; *Org. Synth.*, 58 86–98 (1978). To a mechanically stirred slurry of 1,4,7-tris(p-toluenesulfonyl)-1,4,7-triazaheptane prepared as in Example 1A (486 g, 0.859 mole) in ethanol (1150 ml) heated to reflux under a dry argon atmosphere was added a solution of sodium ethoxide (prepared by dissolving sodium metal (39.5 g, 1.72 mole) in absolute ethanol (1.0 l)) as rapidly as possible. The clear brown solution which formed rapidly was allowed to cool to room temperature and ethyl ether (1.0 l) was added. The crystals were filtered under a dry argon blanket, washed with 3:1 ethanol:ethyl ether and ethyl ether. The crystals were then dried in vacuo to give 509 g (97% yield) of the product as a white powder: $^1$H NMR (DMSO-d$_6$) δ 2.30 (s 6H), 2.36 (s, 3H), 2.63 (t, J=8.7 Hz, 4H), 2.89 (t, J=7.2 Hz, 4H) 7.11 (d, J=8.1 Hz, 4H), 7.28 (d, J=8.0 Hz, 2H), 7.46 (m, 6H).

C. Synthesis of 3,6-Bis(p-toluenesulfonyl)-3,6-diazaoctane-1,8-di-p-toluenesulfonate To a stirred solution of p-toluenesulfonyl chloride (566 g, 2.97 mole) and triethylamine (300 g, 2.97 mole) in CH$_2$Cl$_2$ (2.0 l) at 0° C. under a dry argon atmosphere was added 3,6-diazaoctane-1,8-diol (100 g, 0.675 mole) in portions, maintaining the temperature <10° C. The addition required 30 minutes. The mixture was allowed to warm to room temperature while stirring an additional 18 h and was then poured onto ice (1000 g). The CH$_2$Cl$_2$ layer was separated, washed with 10% HCl H$_2$O and saturated NaCl solution, and dried (MgSO$_4$). The solution was concentrated in vacuo to a volume of 1.5 l. Crystallization by the addition of hexane (4 l) gave 477 g (92% yield) of the product as colorless needles: mp 151°–3° C.; $^1$H NMR (CDCl$_3$) δ 2.43 (s, 12H), 3.29 (s, 4H), 3.36 (t, J=5.2 Hz, 4H) 4.14 (t, J=5.2 Hz, 4H), 7.33 (d, J=7.8 Hz, 8H), 7.71 (d, J=8.2 Hz, 4H), 7.79 (d, J=8.3 Hz, 4H).

D. Synthesis of 1,4,7,10,13-Penta(p-toluenesulfonyl)-1,4,7,10,13-pentaazacyclopentadecane This compound was synthesized following the procedure of Richman, J. E., and Atkins, T. J., *J. Am. Chem. Soc.*, 96, 2268–70 (1974). To a stirred solution of 1,4,7-tris(p-toluenesulfonyl)-1,4,7-triazaheptane-1,7-disodium salt prepared as in Example 1B (146 g, 0.240 mole) in anhydrous DMF (2250 ml) was added dropwise over 3 h to a solution of 3,6-bis(p-toluenesolfonyl)-3,6-diazaoctane-1,8-di-p-toluenesulfonate prepared as in Example 1C (184 g, 0.240 mole) in anhydrous DMF (1020 ml) under a dry argon atmosphere, maintaining the temperature at 100° C. After stirring an additional 1 h at 100° C., the solution was concentrated in vacuo to a volume of 1.5 l. H$_2$O (500 ml) was slowly added at 80° C. to crystallize the product. The resulting slurry was slowly cooled to 0° C. and additional H$_2$O (1250 ml) added. The solid was filtered, washed thoroughly with H$_2$O and then 90% ethanol and dried in vacuo. The off-white solid was dissolved in CH$_2$Cl$_2$, insoluble impurities were removed by filtration and the filtrate was washed with H$_2$O and then dried (MgSO$_4$). The solvent was removed in vacuo to give a yellow solid which was purified by recrystallization from $CH_2Cl_2$-hexane to give 164 g (69% yield) of the product as a white crystalline solid: mp 290°–3° C.; $^1H$ NMR $(CDCl_3)$ δ 2.44 (s, 15H) 3.27 (s, 20H), 7.32 (d, J=8.3 Hz, 10H), 7.66 (d, J=8.3 Hz, 10H).

E. Synthesis of 1,4,7,10,13-Pentaazacyclopentadecane

A mixture of 1,4,7,10,13-penta(p-toluenesulfonyl)-1,4,7,10,13-pentaazacyclopentadecane prepared as in Example 1D (168 g, 0.170 mole) and concentrated $H_2SO_4$ (500 ml) was heated at 100° C. with stirring under a dry argon atmosphere for 70 h. To the resulting dark brown solution ethanol (500 ml) was added dropwise with stirring at 0° C. followed by ethyl ether (3 l). The white solid was filtered and washed with ethyl ether. The solid was then dissolved in $H_2O$ (500 ml) and the resulting solution washed with ethyl ether. Upon reducing the volume of the solution in vacuo to 200 ml, the pH was adjusted to 10–11 with 10N NaOH and the solvent was removed in vacuo. Ethanol (500 ml) was then added and removed in vacuo to dryness. The resulting tan oily solid was extracted with hot THF (2×500 ml) and filtered at room temperature. The filtrates were combined and the solvent removed in vacuo to give the crude product as a yellow crystalline solid which was then redissolved in $CH_3CN$ and filtered to remove insoluble impurities. Recrystallization from cold (–20° C.) $CH_3CN$ gave 11.3 g (31% yield) of the product as colorless needles: mp 108°–9° C.; $^1H$ NMR $(CDCl_3)$ δ 1.74 (br s, 5H), 2.73 (s, 20H); Exact mass $(M+Li)^+$: calcd, 222.2270; Found, 222.2269 $(C_{10}H_{25}N_5Li)$.

F. Synthesis of [Manganese(II)dichloro(1,4,7,10,13-Pentaazacyclopentadecane)]

A solution of 1,4,7,10,13-pentaazacyclopentadecane prepared as in Example 1E (2.0 g, 9.3 mmole) and anhydrous manganese(II) chloride (1.2 g, 9.3 mmole) in anhydrous methanol (50 ml) was refluxed under a dry nitrogen atmosphere for 3 h. The solution was filtered and the solvent removed in vacuo. The resulting solid was recrystallized from ethanol-ethyl ether to give 2.79 g (88% yield) of the product as an off-white crystalline solid: FAB mass spectrum (NBA) m/z (relative intensity) 340 $(M^{3o}, 2)$, 305/307 $((M-Cl)^+100/45))$; Anal. Calcd. for $C_{10}H_{25}Cl_2MnN_5$: C, 35.17; H, 7.38; Cl, 20.76; N 20.60. Found: C, 34.95; H, 7.31; Cl, 20.49; N, 20.22.

EXAMPLE 2

A. Synthesis of N,N'-Di(p-toluenesulfonyl)-1,2-diaminopropane

To a stirred solution of p-toluenesulfonyl chloride (270 g, 1.42 mole) and triethylamine (143 g, 1.42 mole) in $CH_2Cl_2$ (1.0 l) at 0° C. under a dry argon atmosphere was added a solution of 1,2-diaminopropane (50.0 g, 0.675 mole) in $CH_2Cl_2$ (250 ml) dropwise, maintaining the temperature <10° C. The addition required 1 h. The mixture was allowed to warm to room temperature and was stirred an additional 19 h. The mixture was poured onto ice (1000 g) and the $CH_2Cl_2$ layer was separated. The $CH_2Cl_2$ layer was washed with 1N HCl, $H_2O$ and saturated NaCl solution and was dried $(MgSO_4)$. The solvent was removed in vacuo and the resulting yellow oil was washed with hexane. The crude product was purified by recrystallization from $CH_2Cl_2$-hexane to give 241 g (93% yield) of the product as colorless needles: mp 105°–7° C.; $^1H$ NMR$(CDCl_3)$ δ 0.97 (d, J=6.7 Hz, 3H), 2.40 (s, 3H), 2.41 (s, 3H), 2.91 (m, 2H), 3.32 (m, 1H), 5.25 (d, J=7.6 Hz, 1H), 5.38 (t, J=6.3 Hz, 1H), 7.28 (m, 4H) 7.73, (m, 4H).

B. Synthesis of 3,6,9-Tris(p-toluenesulfonyl)-3,6,9-triazaundecane-1,11-diol This compound was synthesized following the procedure of Atkins, T. J., Richman, J. E., and Oettle, W. F., *Org. Synth.*, 58, 86–98 (1978). To a stirred solution of 1,4,7-tris (p-toluenesulfonyl)-1,4,7-triazaheptane-1,7-disodium salt prepared as in Example 1B (120 g, 0.197 mole) in anhydrous DMF (1.0 l) was added ethylene carbonate (173 g, 1.97 mole). The resulting mixture was stirred at 60° C. for 24 h. Upon cooling the mixture to room temperature, $H_2O$ (100 ml) was added to quench the reaction and the solvent was removed in vacuo. The resulting dark yellow oil was dissolved in $CHCl_3$, washed with $H_2O$ and saturated NaCl solution, and was then dried $(MgSO_4)$. The solution was decolorized with activated charcoal and the solvent removed in vacuo to give a yellow tar. The crude product was purified by recrystallization from MeOH-$H_2O$ and dried in vacuo to give 124 g (96% yield) of the product as colorless needles: mp 110°–2° C.; $^1H$ NMR $(CDCl_3)$ δ 2.43 (s, 6H), 2.44 (s, 3H), 3.24 (t, J=5.1 Hz, 4H), 3.39 (m, 8H), 3.79 (m, 4H), 7.33 (m, 6H), 7.72 (m, 6H).

C. Synthesis of 3,6,9-Tris(p-toluenesulfonyl)-3,6,9-triazaundecane-1,11-di-D-toluenesulfonate To a stirred solution of p-toluenesulfonyl chloride (79.6 g, 0.418 mole) and triethylamine (42.3 g, 0.418 mole) in $CH_2Cl_2$ (300 ml) at 0° C. under a dry argon atmosphere was added a solution of 3,6,9-tris(p-toluenesulfonyl)-3,6,9-triazaundecane-1,11-diol prepared as in Example 2B (124 g, 0.190 mole) in $CH_2Cl_2$ (300 ml), maintaining the temperature <10° C. The addition required 30 minutes. The mixture was allowed to warm to room temperature and was stirred an additional 20 h. The mixture was then poured onto ice (1000 g) and the $CH_2Cl_2$ layer was separated. The $CH_2Cl_2$ layer was washed with 1N HCl, $H_2O$ and saturated NaCl solution and was dried $(MgSO_4)$. The solution was decolorized with activated charcoal and the solvent removed in vacuo and the resulting tan oil washed with hexane. The crude product was purified by recrystallization from $CH_2Cl_2$-hexane to give 143 g (78% yield) of the product as needles: mp 158°–60° C.; $^1H$ NMR $(CDCl_3)$ δ 2.42 (s, 6H), 2.43 (s, 6H), 2.46 (s, 3H), 3.29 (m, 8H), 3.40 (t, J=5.3 Hz, 4H), 4.15 (t, J=5.5 Hz, 4H), 7.35 (m, 10H), 7.74 (m, 10H).

D. Synthesis of 2-Methyl-1,4,7,10,13-penta(p-toluenesulfonyl)-1,4,7,10,13-pentaazacyclopentadecane To a stirred solution of N,N'-di(p-toluenesulfonyl)-1,2-diaminopropane prepared as in Example 2A (19.1 g, 0.0500 mole) in anhydrous DMF (500 ml) was added sodium hydride (3.00 g-80% in mineral oil, 0.100 mole) in portions under a dry nitrogen blanket. The resulting mixture was stirred for 30 minutes under a dry argon atmosphere. The solution was then heated to 100° C. and a solution of 3,6,9-tris(p-toluenesulfonyl)-3,6,9-triazaundecane-1,11-di-p-toluenesulfonate prepared as in Example 2C (48.1 g, 0.0500 mole) in anhydrous DMF (250 ml) was added dropwise over a 3 h period, maintaining the temperature at 100° C. After stirring the solution an additional 1 h at 100° C., the mixture was concentrated in vacuo to a volume of 300 ml. $H_2O$ (1.5 l) was slowly added at room temperature to crystallize the product. The resulting solid was filtered, washed thoroughly with $H_2O$ and dried in vacuo. The crude product was purified by recrystallization from CHCl$_3$-MeOH to give 20.6 g (41% yield) of the product as needles: mp 255°–60° C.; $^1$H NMR (CDCl$_3$) δ 0.95 (d, J=6.8 Hz, 3H), 2.43 (s, 3H), 2.44 (s, 9H), 2.46 (s,3H), 3.30 (m, 18H), 4.05 (m, 1H), 7.33 (m, 10H), 7.68 (m, 10H).

E. Synthesis of 2-methyl-1,4,7,10,13-pentaazacyclopentadecane

This compound was synthesized following the procedure of European Patent O 287 465 A1, Oct. 19, 1988. A mixture of 2-methyl-1,4,7,10,13-penta(p-toluenesulfonyl)-1,4,7,10,13-pentaazacyclopentadecane prepared as in Example 2D (20.6 g, 0.0206 mole) and concentrated H$_2$SO$_4$ (75 ml) was heated at 100° C. with stirring under a dry argon atmosphere for 70 h. To the resulting brown solution ethanol (100 ml) was added dropwise with stirring at 0° C., followed by ethyl ether (1 l). The off-white oily solid was filtered and washed thoroughly with ethyl ether. The solid was then dissolved in H$_2$O (100 ml) and the resulting solution was washed with ethyl ether. The pH of the solution was adjusted to 10–11 with 10N NaOH and the solvent was removed in vacuo. Ethanol (2×500 ml) was then added and removed in vacuo. The resulting brown oily solid was extracted with hot THF (2×500 ml) and filtered. The filtrates were combined and the solvent was removed in vacuo. The residue was dissolved in THF (100 ml) and filtered to remove insoluble impurities. The solvent was removed in vacuo to give the crude product as a yellow crystalline solid which was then dissolved in CH$_3$CN and filtered to remove impurities. Crystallization occurred upon cooling the filtrate to –20° C. Recrystallization from cold (–20° C.) CH$_3$CN gave 1.30 g (28% yield) of the product as an off-white crystalline solid: mp 73°–5° C.; $^1$H NMR (CDCl$_3$) δ 1.02 (d, J=6.2 Hz, 3H), 1.71 (br s, 5H), 2.36 (m, 1H), 2.72 (m, 18H); Anal. calcd. for C$_{11}$H$_{27}$N$_5$: C, 57.60; H, 11.87; N, 30.53: Found: C, 57.68; H, 11.34; N, 30.48.

F. Synthesis of [Manganese(II)dichloro(2-Methyl-1,4,7,10,13-pentaazacyclopentadecane)]

A solution of 2-methyl-1,4,7,10,13-pentaazacyclopentadecane prepared as in Example 2E (1.2 g, 5.3 mmole) and anhydrous manganese(II) chloride (0.67 g, 5.3 mmole) in anhydrous methanol (60 ml) was refluxed under a dry nitrogen atmosphere for 2 h. A small amount of suspended solid was removed by filtration and the solvent was removed in vacuo. The residue was recrystallized from ethanol-ethyl ether to give 0.81 g (43% yield) of the product as a white solid: FAB mass spectrum (NBA) m/z (relative intensity) 354 (M$^+$, 3), 319/321 [(M-Cl)$^+$, 100/31]; Anal. calcd. for C$_{11}$H$_{27}$Cl$_2$MnN$_5$: C, 37.19; H, 7.66; Cl, 19.96; N, 19.72. Found: C, 36.73;H, 7.32; Cl, 19.85; N, 19.49.

EXAMPLE 3

A. Synthesis of (S)-1,2-Diaminopropane

This compound was synthesized following the procedure of Bláha, K., Budesinsky, M., Koblicova, Z. et al, Coll. Czech. Chem. Commun., 47, 1000–19 (1982). To a stirred slurry of L-alanine amide hydrochloride (30.0 g, 0.241 mole) in anhydrous THF (200 ml) at room temperature under a dry argon atmosphere was added a solution of lithium aluminum hydride (963 ml-1.0M in THF, 0.963 mole) over a 15 minute period. The mixture was refluxed for 8 h and then quenched by the dropwise addition of H$_2$O (200 ml) while cooling in an ice bath. The solid was filtered, washed with THF (500 ml) and then hot methanol (2×1.0 l).

The filtrate and washings were combined, acidified to pH 1 with concentrated HCl and the solvent was removed in vacuo. The oily residue was dissolved in ethanol and the solvent was removed in vacuo to give a yellow crystalline solid (46.0 g). The solid was ground to a powder and an excess of powdered NaOH (60 g) was added. The mixture was heated to a melt and the product was vacuum distilled at 15mm Hg (bp 70° C.) to give 20.3 g of the crude product as a colorless oil. The oil was dried by the addition of small pieces of metallic sodium and was fractionally distilled at atmospheric pressure to give 11.6 g (65% yield) of the product as a colorless oil: bp 118°–25° C.; [α]$_d^{20}$=+32.6° (C=0.01, C$_6$H$_6$); $^1$H NMR (CDCl$_3$) δ 1.06 (d, J=6.3 Hz, 3H), 1.35 (br s, 4H), 2.45 (m, 1H), 2.68 (dd, J=12.5, 4.5, Hz, 1H), 2.84 (m, 1H).

B. Synthesis of N,N'-Di(p-toluenesulfonyl)-(S)-1,2-diaminopropane

To a stirred solution of p-toluenesulfonyl chloride (60.2 g, 0.316 mole) and triethylamine (32.0 g, 0.316 mole) in CH$_2$Cl$_2$ (250 ml) at 0° C. under a dry argon atmosphere was added a solution of (S)-1,2-diaminopropane prepared as in Example 3A (11.2 g, 0.150 mole) in CH$_2$Cl$_2$ (75 ml), maintaining the temperature <10° C. The addition required 1 h. The mixture was allowed to warm to room temperature and was stirred an additional 15 h. The mixture was then poured onto ice (500 g) and the CH$_2$Cl$_2$ layer was separated. The CH$_2$Cl$_2$ layer was washed with 1N HCl, H$_2$O and saturated NaCl solution and was dried (MgSO$_4$). The solvent was removed in vacuo and the resulting yellow oil was washed with hexane. The crude product was purified by recrystallization from CH$_2$Cl$_2$-hexane to give 45.2 g (79% yield) of the product as a white crystalline solid: mp 120°–1° C; [α]$_d^{20}$=–42.6° (C=0.01, CHCl$_3$); $^1$H NMR (CDCl$_3$) δ 1.00 (d, J=6.8 Hz, 3H), 2.42 (s, 6H), 2.85 (m, 1H), 2.98 (m, 1H), 3.32 (m, 1H), 4.94 (d, J=7.5 Hz 1H), 5.14 (t, J=6.6 Hz, 1H), 7.30 (m, 4H), 7.72 (m, 4H).

C. Synthesis of (S)-2-Methyl-1,4,7,10,13-penta(p-toluenesulfonyl)-1,4,7,10,13-pentaazacyclopentadecane To a stirred solution of N,N'-di(p-toluenesulfonyl)-(S)-1,2-diaminopropane prepared as in Example 3B (19.1 g, 0.0500 mole) in anhydrous DMF (500 ml) was added sodium hydride (3.00 g-80% in mineral oil, 0.100 mole) in portions under a dry nitrogen blanket and the resulting mixture was stirred for 30 minutes under a dry argon atmosphere. The solution was then heated to 100° C. and a solution of 3,6,9-tris(p-toluenesulfonyl)-3,6,9-triazaundecane-1,11-di-p-toluenesulfonate prepared as in Example 2C (48.1 g, 0.0500 mole) in anhydrous DMF (250 ml) was added dropwise over a 3 h period, maintaining the temperature at 100° C. The mixture was concentrated in vacuo to a volume of 300 ml. A 1:1 mixture of MeOH-H$_2$O (200 ml) and then H$_2$O (1.5 l) were slowly added at room temperature to crystallize the product. The resulting solid was collected by filtration and washed thoroughly with H$_2$O. The solid was then dissolved in CHCl$_3$ and dried (MgSO$_4$), and the solvent was removed in vacuo to give a pale yellow solid. The crude product was purified by recrystallization from CHCl$_3$-MeOH to give 23.5 g (47% yield) of the product as a dense white crystalline solid: mp 245°–7° C.; $^1$H NMR (CDCl$_3$) δ 0.95 (d, J=7.0 Hz, 3H), 2.43 (s, 3H), 2.44 (s, 9H), 2.45 (s, 3H), 3.31 (m, 18H), 4.05 (sext, J=5.9 Hz, 1H), 7.33 (m, 10H), 7.69 (m, 10H).

D. Synthesis of (S)-2-Methyl-1,4,7,10,13-pentaazacyclopentadecane

A mixture of (S)-2-methyl-1,4,7,10,13-penta(p-toluenesulfonyl)-1,4,7,10,13-pentaazacyclopentadecane prepared as in Example 3C (22.9 g, 0.0229 mole) and concentrated $H_2SO_4$ (85 ml) was heated at 100° C. with stirring under a dry argon atmosphere for 71 h. To the resulting brown solution, ethanol (100 ml) was added dropwise with stirring at 0° C. followed by ethyl ether 1 l). The dark brown solid was filtered and washed thoroughly with ethyl ether. The solid was then dissolved in $H_2O$ (100 ml) and the resulting solution washed with ethyl ether. The pH of the solution was adjusted to 11 with 10N NaOH and the solvent was removed in vacuo. Ethanol (2×500 ml) was then added and removed in vacuo. The resulting brown oily solid was extracted with hot THF (2×500 ml) and filtered. The filtrates were combined and the solvent was removed in vacuo. The residue was dissolved in hot THF (500 ml) and was filtered. The solvent was removed in vacuo and the residue was dissolved in $CHCl_3$. After filtering to remove cloudiness, the solvent was removed in vacuo and the crude product was purified by fractional distillation in vacuo to give a pale yellow oil which crystallized on standing. The material was further purified by recrystallization from cold (−20° C.) $CH_3CN$ to give 641 mg (12% yield) of the product as a white crystalline solid: mp 87°–9° C.; $[\alpha]_d^{20}=+37.2°$ (C=0.01, $C_6H_6$); $^1H$ NMR ($CDCl_3$) δ 1.02 (d, J=6.3 Hz, 3H), 1.81 (br s, 5H), 2.37 (m, 1H), 2.75 (m, 18H); Exact mass $(M+Li)^+$: calcd., 236.2426; found, 236.2425 ($C_{11}H_{27}N_5Li$).

E. Synthesis of [Manganese(II)dichloro((S)-2-Methyl-1,4,7,10,13-pentaazacyclopentadecane)]

A solution of (S)-2-methyl-1,4,7,10,13-pentaazacyclopentadecane prepared as in Example 3D (0.55 g, 2.4 mmole) and anhydrous manganese(II) chloride (0.30 g, 2.4 mmole) in anhydrous methanol was refluxed under a dry nitrogen atmosphere for 16 h. The solution was filtered and the solvent was removed in vacuo. The residue was recrystallized from THF ethyl ether to give 0.70 g (82% yield) of the product as a white crystalline solid: $[\alpha]_d^{20}=+22.6°$ (C=0.005, MeOH); FAB mass spectrum (NBA) m/z (relative intensity) 354 ($M^+$, 3), 319/321 [$(M-Cl)^{30}$, 100/31]; Anal calcd. for $C_{11}H_{27}Cl_2MnN_5$: C, 37 19;H, 7.66; Cl, 19.66; N, 19.72. Found: C, 36.90; H, 7.84; Cl, 19.74; N, 19.42.

EXAMPLE 4

A. Synthesis of (R)-1,2-Diaminopropane Dihydrochloride

A solution of 1.0M lithium aluminum hydride in THF (480 ml, 0.480 mol) was added over a period of 30 minutes to a stirred solution of D-alanine amide hydrochloride (15.0 g, 0.120 mol) in anhydrous THF (100 ml) at room temperature under a dry argon atmosphere. The mixture was refluxed overnight. After cooling, the mixture was quenched with $H_2O$ (120 ml). The precipitate (LiCl) was filtered and washed with THF (300 ml) and hot MeOH (2×600 ml). The filtrate and washes were combined and acidified with concentrated HCl. The solvent was removed in vacuo to give a yellow oil. The oil was crystallized from MeOH/ether to give 9.97 g (57% yield) of a white crystalline solid: mp 240°–5° C.; $[\alpha]_d^{20}=+7.60°$ (c=0.01, MeOH); $^1H$ NMR (DMSO-$d_6$) δ 1.30 (d, J=6.9 Hz, 3H), 3.09 (ABq of dd, δv=44.5 Hz, J=13.5, 6.2 Hz, 2H) 3.52 (m, 1H), 8.59 (br s, 6H).

B. Synthesis of N,N'-Di(p-toluenesulfonyl)-(R)-1,2-diaminopropane

A suspension of (R)-1,2-diaminopropane dihydrochloride prepared as in Example 4A (9.76 g, 66.4 mmole) in ethyl ether (60 ml) was added to a stirred solution of NaOH (13.3 g, 332 mmole) in $H_2O$ (110 ml) at 0° C. under a dry argon atmosphere. p-Toluenesulfonyl chloride (27.8 g, 146 mole) was added neat in portions to the mixture which was maintained at 0° C. The mixture was allowed to warm to room temperature and to stir overnight. After stirring 22 h, $CH_2Cl_2$ (200 ml) was added. The layers were separated and the $CH_2Cl_2$ layer was collected. The aqueous layer was extracted with $CH_2Cl_2$ (2×75 ml). The combined extracts were dried ($MgSO_4$) and the solvent was removed in vacuo to give a white solid. The solid was recrystallized from $CH_2Cl_2$-hexane to give 18.5 g (73% yield) of a white crystalline solid: mp 121°–3° C.; $[\alpha]_d^{20}=+48.5$ (C=0.01, $CHCl_3$); $^1H$ NMR ($CDCl_3$) δ 1.02 (d, J=6.9 Hz, 3H), 2.44 (s, 6H), 2.87 (m, 1H), 2.98 (m, 1H), 3.33 (m, 1H), 4.80 (d, J=7.2 Hz, 1H), 5.03 (t, J=6.5 Hz, 1H), 7.30 (m, 4H), 7.73 (m, 4H).

C. Synthesis of (R)-2-Methyl-1,4,7,10,13-penta(p-toluenesulfonyl)-1,4,7,10,13-pentaazacyclopentadecane Sodium hydride (2.87 g-80% in mineral oil, 95.6 mmole) was added to a stirred solution of N,N'-di(p-toluenesulfonyl) -(R)-1,2-diaminopropane prepared as in Example 4B (18.3 g, 47.8 mmole) in anhydrous DMF (480 ml) at room temperature under a dry argon atmosphere. After $H_2$ evolution was complete (60 min), the mixture was heated to 100° C. A solution of 3,6,9-tris(p-toluenesulfonyl)-3,6,9-triazaundecane-1,11-di-p-toluenesulfonate prepared as in Example 2C (46.0 g, 47.8 mmole) in anhydrous DMF (240 ml) was added to the stirred mixture at 100° C. over a period of 3 h. The mixture was heated an additional 1.5 h at 100° C. After cooling, the mixture was concentrated in vacuo to a volume of 250 ml. A solution of 1:1$H_2O$/MeOH (200 ml) was added dropwise, followed by $H_2O$ (1500 ml). The precipitate was collected by filtration and washed with $H_2O$. The solid was dried in vacuo and recrystallized from $CHCl_3$/MeOH to give 21.6 g (45% yield) of a white crystalline solid: mp 256°–8° C.; $^1H$ NMR (DMSO-$d_6$) δ 1.05 (m, 3H), 2.42 (s, 15H), 3.15 (m, 19H), 7.46 (m, 10H), 7.58 (m, 10H).

D. Synthesis of (R)-2-Methyl-1,4,7,10,13-pentaazacyclopentadecane

A mixture of 2-(R)-methyl-1,4,7,10,13-penta(p-toluenesulfonyl)-1,4,7,10,13-pentaazacyclopentadecane as in Example 4C (19.5 g, 19.4 mmole), phenol (9.13 g, 97.0 mmole) and 30% HBr in acetic acid (260 ml) was stirred for 21 h at 120° C. in a sealed Fischer-Porter bottle. A solid precipitated during the heating period. After cooling, 1:1 ethanol/ethyl ether (250 ml) was added, followed by ether (3000 ml). The solid was collected by filtration and was washed with ethyl ether. The solid was dissolved in $H_2O$ (1000 ml) and the aqueous solution was washed with ethyl ether (3×2000 ml). The aqueous solution was concentrated in vacuo to 50 ml. The gradual addition of isopropanol (900 ml) precipitated 10.6 g of the pentahydrobromide salt. The salt was dissolved in $H_2O$ (100 ml), the pH of the solution was adjusted to 11 with 10N NaOH and the solvent was removed in vacuo to dryness. Ethanol (2×500 ml) was then added and removed in vacuo to dryness. The resulting white oily solid was extracted with hot THF (2×500 ml) and filtered at room temperature. The filtrates were combined and the solvent was removed in vacuo. The oil was redissolved in THF and insoluble impurities were removed by filtration. The solvent was removed in vacuo, the residue was redissolved in $CH_3CN$, and cloudiness was removed by filtration. The crude product was purified by recrystallization from cold (−20° C.) CH$_3$CN to give 0.762 g (17% yield) of the product as a white crystalline solid: mp 88°–89.5° C.; [α]$_d^{20}$=−38.6° (c=0.01, benzene); $^1$H NMR (CDCl$_3$) δ 1.02 (d, J=6.2 Hz, 3H), 1.68 (br s, 5H), 2.36 (m, 1H), 2.72 (m, 18 H); Exact mass (M+H)$^+$: calcd., 230.2345; Found, 230.2354 (C$_{11}$H$_{28}$N$_5$).

E. Synthesis of [Manganese(II)dichloro((R)-2-Methyl-1,4,7,10,13-pentaazacyclopentadecane)]

A solution of (R)-2-methyl-1,4,7,10,13-pentaazacyclopentadecane prepared as in Example 4D (0.600g, 2.6 mmole) and anhydrous manganese(II) chloride (0.33 g, 2.6 mmole) in anhydrous MeOH (50 ml) was refluxed under a dry nitrogen atmosphere for 12 h. After cooling, the mixture was filtered through celite and concentrated in vacuo. Ethyl ether was added to induce crystallization. The crystals were collected by filtration, washed with ether, and dried to give 680 mg (73% yield) of a white crystalline solid: [α]$_d^{20}$=−21.0° (c=0.005, MeOH); FAB mass spectrum (NBA) m/z (relative intensity) 354 (M+, 2), 319/321 ((M−Cl)$^{+, 100/30}$); Anal. calcd. for C$_{11}$H$_{27}$Cl$_2$MnN$_5$: C, 37.30; H, 7.40; N, 19.77. Found: C, 36.72;H, 7.69; N, 18.82.

EXAMPLE 5

A. Synthesis of 1,2-Diamino-4-methylpentane Dihydrochloride

To a stirred slurry of D,L-leucine amide hydrochloride (50.0 g, 0.300 mole) in anhydrous THF (500 ml) at room temperature under a dry argon atmosphere was added a solution of lithium aluminum hydride (1200 ml-1.0M in THF, 1.20 mole) over a 15 minute period. The mixture was refluxed for 8 h and then quenched by the dropwise addition of H$_2$O (200 ml) while cooling in an ice bath. The mixture was filtered to remove solid and the filtrate was retained. The solid was washed with THF (100 ml) and slurried in hot THF (2×1.0 l). The THF filtrates and washings were combined and the solid was discarded. The THF solution was acidified to pH 1 with concentrated HCl. The solvent was removed in vacuo to give a pale yellow oil. The oil was dissolved in ethanol and the solvent was removed in vacuo to give an oil which crystallized. The crude material was purified by recrystallization from MeOH-ethyl ether to give 42.3 g (75% yield) of the product as a white crystalline solid: mp 228°–30° C.; $^1$H NMR (DMSO-d$_6$) δ 0.89 (d, J=6.5 Hz, 3H), 0.90 (d, J=6.5 Hz, 3H), 1.51 (t, J=7.2 Hz, 2H), 1.75 (Sept, J=6.7 Hz, 1H), 3.08 (m, 2H), 3.49 (m, 1H).

B. Synthesis of N,N'-Di(p-toluenesulfonyl)-1,2-diamino-4-methylpentane

To a stirred solution of 5N NaOH (100 ml) was added 1,2-diamino-4-methylpentane dihydrochloride prepared as in Example 5A (42.3 g, 0.223 mole). The resulting solution was saturated with NaCl and the amine was extracted with CH$_2$Cl$_2$ (5×200 ml). The extracts were combined, dried (MgSO$_4$) and reduced in vacuo to a volume of 200 ml. This solution was then added dropwise to a stirred solution of p-toluenesulfonyl chloride (89.4 g, 0.469 mole) and triethylamine (47.5 g, 0.469 mole) in CH$_2$Cl$_2$ (400 ml) at 0° C. The addition required 1 h. The mixture was allowed to warm to room temperature and was stirred an additional 19 h. The mixture was then poured onto ice (1000 g) and the CH$_2$Cl$_2$ layer was separated. The CH$_2$Cl$_2$ layer was washed with 1N HCl, H$_2$O and saturated NaCl solution and was dried (MgSO$_4$). The solvent was removed in vacuo and the resulting yellow oil washed with hexane. The crude product was purified by recrystallization from CH$_2$Cl$_2$-hexane to give 67.9 g (72% yield) of the product as a white crystalline solid: mp 138°–40° C.; $^1$H NMR (CDCl$_3$) δ 0.53 (d, J=6.5 Hz, 3H), 0.68 (d, J=6.5 Hz, 3H), 1.21 (m, 2H), 1.34 (sept, J=6.6 Hz, 1H), 2.43 (s, 6H), 2.87 (m, 1H), 3.02 (m, 1H), 3.18 (m, 1H), 4.74 (d, J=7.5 Hz, 1H), 5.16 (t, J=6.3 Hz, 1H), 7.30 (d, J=8.8 Hz, 4H), 7.72 (m, 4H).

C. Synthesis of 2-(2-Methylpropyl)-1,4,7,10,13-penta(p-toluenesulfonyl)-1,4,7,10,13-pentaazacyclopentadecane To a stirred solution of N,N'-di(p-toluenesulfonyl)-1,2-diamino-4-methylpentane prepared as in Example 5B (21.2 g, 0.0500 mole) in anhydrous DMF (500 ml) was added sodium hydride (3.00 g-80% in mineral oil, 0.100 mole) in portions under a dry nitrogen blanket. The resulting mixture was stirred for 30 minutes under a dry argon atmosphere. The solution was then heated to 100° C. and a solution of 3,6,9-tris(p-toluenesulfonyl)-3,6,9-triazaundecane-1,11-di-p-toluenesulfonate prepared as in Example 2C (48.1 g, 0.0500 mole) in anhydrous DMF (250 ml) was added dropwise over a 3 h period, maintaining the temperature at 100° C. After stirring the solution an additional 1 h at 100° C., solvent was removed in vacuo to a volume of 300 ml. A 1:1 mixture of MeOH-H$_2$O (200 ml) and then H$_2$O (1.4 l) were slowly added at room temperature to crystallize the product. The resulting solid was filtered and washed thoroughly with H$_2$O. The solid was then dissolved in CHCl$_3$ and dried (MgSO$_4$), and the solvent was removed in vacuo to give a glassy yellow solid. The crude product was purified by recrystallization from CHCl$_3$-MeOH to give 14.2 g (27% yield) of the product as colorless needles: mp 142°–5° C.; $^1$H NMR (CDCl$_3$) δ 0.80 (d, J=5.9 Hz, 3H), 0.83 (br s, 3 H), 1.26 (br s, 1H), 1.37 (br s, 2H), 2.40 (s, 3H), 2.44 (s, 3H), 2.45 (s, 3H), 2.46 (s, 6H), 3.17 (br m, 18H), 4.28 (br s, 1H), 7.32 (m, 10H), 7.71 (m, 10H).

D. Synthesis of 2-(2-Methylpropyl)1,4,7,10,13-pentaazacyclopentadecane

A mixture of 2-(2-methylpropyl)-1,4,7,10,13-penta(p-toluenesulfonyl)-1,4,7,10,13-pentaazacyclopentadecane prepared as in Example 5C (14.1 g, 0.0135 mole) and concentrated H$_2$SO$_4$ (50 ml) was heated at 100° C. with stirring under a dry argon atmosphere for 69 h. To the resulting brown solution ethanol (70 mL) was added dropwise with stirring at 0° C., followed by ethyl ether (1 l). The brown solid was filtered and washed thoroughly with ethyl ether. The solid was then dissolved in H$_2$O (100 ml) and the resulting solution washed with ethyl ether. A small amount of solid was removed by filtration, the pH was adjusted to 10–11 with 10N NaOH and the solvent was removed in vacuo. Ethanol (2×250 ml) was then added and removed in vacuo. The resulting brown oily solid was extracted with hot THF (2×500 ml) and filtered at room temperature. The filtrates were combined, the solvent was removed in vacuo and the residue was dissolved in THF and filtered. The solvent was removed in vacuo to give the crude product as a tan oil which was then dissolved in CH$_3$CN and filtered to remove insoluble impurities. Crystallization occurred upon cooling the filtrate to −20° C. Recrystallization from cold (−20° C.) CH$_3$CN gave 715 mg (20% yield) of the product as a white crystalline solid: mp 70°–6° C.; $^1$H NMR (CDCl$_3$) δ 0.89 (d, J=6.5 Hz, 3H), 0.90 (d, J=6.6 Hz, 3H), 1.13 (m, 1H), 1.39 (m, 1H), 1.64 (sept, J=6.3 Hz, 1H), 2.05 (br s, 5H), 2.34 (m, 1H), 2.75 (m, 18H); Exact mass (M+Li)$^+$: calcd. 278.2896; found, 278.2919 (C$_{14}$H$_{33}$N$_5$Li).

E. Synthesis of [Manganese(II)dichloro(2-(2-Methylpropyl)-1,4,7,10,13-pentaazacyclopentadecane)]

A solution of 2-(2-methylpropyl)-1,4,7,10,13-pentaazacyclopentadecane prepared as in Example 5D (0.66 g, 2.4 mmole) and anhydrous manganese(II) chloride (0.31 g, 2.4 mmole) in anhydrous methanol (40 ml) was refluxed under a dry nitrogen atmosphere overnight. The solution was filtered and the solvent removed in vacuo. The resulting yellow solid was recrystallized from THF-ethyl ether to give 0.46 g (48% yield) of the product as an off-white solid: FAB mass spectrum (NBA) m/z (relative intensity) 396 ($M^{3O}$, 1), 361/363 [$(M-Cl)^+$ 84/26], 272 [$(M-MnCl_2+H)^{3O}$ 100]. Anal. Calcd. for $C_{14}H_{33}Cl_2MnN_5$: C, 42.33; H, 8.37; N, 17.63. Found: C, 41.90; H, 8.22; N, 17.30.

EXAMPLE 6

A. Synthesis of 1,2-Diamino-3-phenylpropane

To a stirred slurry of D,L-phenylalanine amide hydrochloride (50.0 g, 0.249 mole) in anhydrous THF (200 ml) at room temperature under a dry argon atmosphere was added a solution of lithium aluminum hydride (1000 ml-1.0M in THF, 1.00 mole) over a 30 minute period. The mixture was refluxed for 7.5 h and then quenched by the dropwise addition of $H_2O$ (200 ml) while cooling in an ice bath. The solid was filtered, washed with hot THF (2×500 ml) and then hot methanol (2×500 ml). The filtrate and washings were combined and the solvent was removed in vacuo. The resulting yellow oil was dissolved in $CHCl_3$ and the solution was filtered and dried ($MgSO_4$). The solvent was removed in vacuo to give 34.6 g (92% yield) of the crude product as a yellow oil which crystallized on standing: $^1H$ NMR ($CDCl_3$) δ 1.68 (br s, 4H), 2.51 (m, 2H), 2.79 (m, 2H), 2.95 (m, 1H), 7.24 (m, 5H).

B. Synthesis of N,N'-Di(p-toluenesulfonyl)-1,2-diamino-3-phenylpropane

To a stirred solution of p-toluenesulfonyl chloride (92.0 g, 0.482 mole) and triethylamine (48.8 g, 0.482 mole) in $CH_2Cl_2$ (350 ml) at 0° C. under a dry argon atmosphere was added a solution of 1,2-diamino-3-phenylpropane prepared as in Example 6A (34.5 g, 0.230 mole) in $CH_2Cl_2$ (100 ml), maintaining the temperature <10° C. The addition required 1 h. The mixture was allowed to warm to room temperature and was stirred an additional 15 h. The mixture was then poured onto ice (500 g) and the $CH_2Cl_2$ layer was separated. The $CH_2Cl_2$ layer was washed with 1N HCl, $H_2O$ and saturated NaCl solution and was dried ($MgSO_4$). The solvent was removed in vacuo and the resulting yellow oil washed with hexane. The crude product was purified by recrystallization from $CH_2Cl_2$-hexane to give 71.4 g (68% yield) of the product as a crystalline solid: mp 128°–31° C.; $^1H$ NMR ($CDCl_3$) δ 2.42 (s, 3H), 2.43 (s, 3H), 2.69 (ABq of dd, δv=44.0 Hz, J=14.0, 6.6 Hz, 2H), 3.02 (m, 2 H), 3.36 (hex, J=6.6 Hz, 2H), 4.85 (d, J=6.6 Hz, 1H), 5.16 (t, J=6.5 Hz, 1H), 6.87 (m, 2H), 7.15 (m, 5H), 7.29 (m, 2H), 7.50 (m, 2H), 7.70 (m, 2H).

C. Synthesis of 2-Phenylmethyl-1,4,7,10,13-penta-(p-toluenesulfonyl)-1,4,7,10,13-pentaazacyclopentadecane To a stirred solution of N,N'-di(p-toluenesulfonyl)-1,2-diamino-3-phenylpropane prepared as in Example 6B (68.8 g, 0.150 mole) in anhydrous DMF (1500 ml) was added sodium hydride (9.00 g-80% in mineral oil, 0.300 mole) in portions under a dry nitrogen blanket. The resulting mixture was stirred for 2 h at room temperature under a dry argon atmosphere. A solid white crystalline mass formed which was partially solubilized by heating the mixture to 50° C., followed by the addition of 1,4,7,10,13,16-hexaoxacyclooctadecane (79.6 g, 0.300 mole) and then anhydrous DMF (1500 ml). The thin slurry was then heated to 100° C. and a solution of 3,6,9-tris(p-toluenesulfonyl)-3,6,9-triazaundecane-1,11-di-p-toluenesulfonate prepared as in Example 2C (144 g, 0.150 mole) in anhydrous DMF (750 ml) was added dropwise over a 5 h period, maintaining the temperature at 100° C. After stirring the solution an additional 15 h at 100° C., the mixture was concentrated in vacuo to a volume of 1 l. A 2:1 mixture of MeOH-$H_2O$ (500 ml) and then $H_2O$ (3.5 l) were slowly added at 0° C. to crystallize the product. The resulting tan solid was filtered and washed thoroughly with $H_2O$. The product was recrystallized from DMF-$H_2O$ and then dissolved in The $CHCl_3$ solution was washed with $H_2O$ and dried ($MgSO_4$), and the solvent was removed in vacuo to give a yellow tar. The crude product was purified by recrystallization from $CHCl_3$-MeOH to give 59.6 g (37% yield) of the product as a fine off-white crystalline solid: mp 288°–92° C.; $^1H$ NMR ($CDCl_3$) δ 2.38 (s, 3H), 2.41 (s, 3H), 2.44 (s, 3H), 2.46 (s, 6H), 3.28 (m, 21H), 7.15 (m, 2H), 7.22 (m, 7H), 7.34 (m, 8H), 7.67 (m, 8H).

D. Synthesis of 2-Phenylmethyl-1,4,7,10,13-pentaazacyclopentadecane

A mixture of 2-phenylmethyl-1,4,7,10,13-penta(p-toluenesulfonyl)-1,4,7,10,13-pentaazacyclopentadecane prepared as in Example 6C (20.0 g, 0.0186 mole), phenol (8.75 g, 0.0929 mole) and 30% HBr in glacial acetic acid (250 ml) were heated in each of 2 sealed tubes in the dark at 120° C. for 16 h. Upon cooling to room temperature, a 1:1 mixture of ethanol and ethyl ether (250 ml) was added to each tube. The contents of the tubes were combined and ethyl ether (3 l) was added. The dark brown solid was filtered and washed thoroughly with ethyl ether. The oily solid was then dissolved in $H_2O$ (1 l) and the resulting solution was washed with ethyl ether. The solution was concentrated in vacuo to a volume of 250 ml. The pentahydrobromide salt was crystallized by the addition of isopropanol (1 l), followed by cooling to 5° C. The pentahydrobromide salt (21.2 g) was dissolved in $H_2O$ (50 ml) and the resulting solution was washed with ethyl ether. The pH of the solution was adjusted to 11 with 10N NaOH and the solvent was removed in vacuo. Ethanol (2×500 ml) was then added and removed in vacuo. The resulting brown oily solid was extracted with hot THF (2×500 ml) and filtered at room temperature. The filtrates were combined, the solvent was removed in vacuo and the oil was redissolved in THF. After filtration, the solvent was removed in vacuo. The residue was redissolved in a 1:1 mixture of $CH_3CN$-THF and the solution was filtered. The solvent was removed in vacuo and the crude product was purified by recrystallization from cold $CH_3CN$ (−20° C.) to give 4.47 g (39% yield) of an off-white crystalline solid: mp 98°–100° C.; $^1H$ NMR ($CDCl_3$) δ 1.75 (br s, 5H), 2.35 (m, 1H), 2.73 (m, 20H), 7.22 (m, 5H); Anal. calcd. for $C_{17}H_{31}N_5$: C, 66.84; H, 10.23; N, 22.93. Found: C, 66.86; H, 10.26; N, 23.32.

E. Synthesis of [Manganese(II)dichloro(2-Phenylmethyl-1,4,7,10,13-pentaazacyclopentadecane)]

A solution of 2-phenylmethyl-1,4,7,10,13-pentaazacyclopentadecane prepared as in Example 6D (1.5 g, 4.9 mmole) and anhydrous manganese(II) chloride (0.62 g, 4.9 mmole) in anhydrous methanol was refluxed under a dry nitrogen atmosphere overnight. The solution was filtered and the solvent removed in vacuo. The yellow gummy solid was purified by stirring vigorously in acetone to give 1.89 g (89% yield) of the product as a white solid: FAB mass spectrum (NBA) m/z (relative intensity) 395/397 [(M–Cl)$^+$, 100/31]; Anal. calcd. for $C_{17}H_{31}Cl_2MnN_5$: C, 47.34; H, 7.24; Cl, 16.44; N, 16.24. Found: C, 46.84; H, 7.51; Cl, 16.38; N, 15.86.

EXAMPLE 7

A. Synthesis of 2-Cyclohexylmethyl-1,4,7,10,13-pentaazacyclopentadecane

To a stirred solution of 2-phenylmethyl-1,4,7,10,13-pentaazacyclopentadecane prepared as in Example 6D (1.00g, 3.27 mmole), MeOH (400 ml) and 2N HCl (10.0 ml) was added 5% rhodium on carbon (1.00 g). The mixture was hydrogenated at 60 psi. The vessel was periodically repressurized to 60 psi. Hydrogen uptake ceased after 10 days and at 11 days the catalyst was filtered and the solvent removed in vacuo to give a yellow solid. The crude pentahydrochloride salt was purified by crystallization from MeOH-ethyl ether to give 1.43 g of the salt as off-white needles. The salt was dissolved in $H_2O$ (10 ml) and the pH of the solution was adjusted to pH 10–11 with 10N NaOH. The solvent was removed in vacuo. Ethanol (2×100 ml) was added and removed in vacuo. The resulting oily solid was extracted with hot THF (2×250 ml) and filtered. The filtrates were combined and the solvent was removed in vacuo. The resulting yellow oil was dissolved in $CH_3CN$ and the solution was filtered. Crystallization occurred upon cooling to −20° C. Recrystallization from cold (−20° C.) $CH_3CN$ gave 486 mg (48% yield) of the product as an off-white crystalline solid: mp 87°–9° C.; $^1H$ NMR ($CDCl_3$) δ 0.89 (m, 2H), 1.20 (m, 6H), 1.42 (m, 1H), 1.70 (m, 9H), 2.31 (m, 1H), 2.68 (m, 17H), 2.86 (m, 1H); Exact mass (M+H)+: calcd., 312.3127; Found, 312.3172 ($C_{17}H_{38}N_5$).

B. Synthesis of [Manganese(II)dichloro(2-Cyclohexylmethyl-1,4,7,10,13-pentaazacyclopentadecane)]

A solution of 2-cyclohexylmethyl-1,4,7,10,13-pentaazacyclopentadecane prepared as in Example 7A (0.43 g, 1.4 mmole) and anhydrous manganese(II) chloride (0.17 g, 1.4 mmole) in anhydrous methanol (30 ml) was refluxed under a dry nitrogen atmosphere overnight. The solution was filtered and concentrated in vacuo to a volume of 3 ml. Ethyl ether (20 ml) was added. Upon cooling to 0° C., 0.39 g (65% yield) of the product was obtained as a white solid: FAB mass spectrum (NBA) m/z (relative intensity) 401/403 [(M–Cl)$^+$, 100/33]: Anal. Calcd. for $C_{17}H_{37}Cl_2MnN_5$: C, 46.69; H, 8.53; N, 16.09. Found: C, 45.87; H, 8.40; N, 15.55.

EXAMPLE 8

Synthesis of [Manganese(II)diacetate(1,4,7,10,13-Pentaazacyclopentadecane)]

A solution of 1,4,7,10,13-pentaazacyclopentadecane prepared as in Example 1E (1.0 g, 4.7 mmole) and anhydrous manganese(II) acetate (0.80 g, 4.7 mmole) in anhydrous methanol was refluxed under a dry nitrogen atmosphere overnight. The solvent was removed in vacuo and the resulting oil was dissolved in ethyl ether (30 ml). The solution was filtered to remove cloudiness and upon evaporative cooling, 0.85 g (47% yield) of the product was obtained as a white crystalline solid: FAB mass spectrum (NBA) m/z (relative intensity) 329 ((M–OAc)$^+$, 100); Anal. calcd. for $C_{14}H_{31}MnN_5O_4$: C, 43.30; H, 8.05; N, 18.03. Found: C, 42.80; H, 7.92; N, 17.78.

EXAMPLE 9

Synthesis of [Manganese(II)nitrate(1,4,7,10,13-pentaazacyclopentadecane)]Nitrate A solution of 1,4,7,10,13-pentaazacyclopentadecane prepared as in Example 1E (0.50 g, 2.3 mmole) and manganese (II) nitrate tetrahydrate (0.61 g, 2.3 mmole) in anhydrous methanol (50 ml) was refluxed for 2 h under a dry nitrogen atmosphere. The solution was filtered and concentrated in vacuo to a volume of 10 ml. The solution was warmed and ethyl ether (10 ml) was added. Crystallization occurred upon cooling to room temperature to give 0.80 g (87% yield) of the product as large colorless crystals: FAB mass spectrum (NBA) m/z (relative intensity) 332 [(M–$NO_3$)$^{30}$, 100]; Anal. calcd. for $C_{10}H_{25}MnN_7O_6$: C, 30.46; H, 6.39; N, 24.87. Found: C, 31.09; H, 6.33; N, 25.34.

Comparative Examples 10–26

Manganese(II) complexes of other nitrogen-containing macrocyclic ligands were prepared according to the procedures set forth. The compounds were compared to the compounds of Examples 1–9 and 27–42 as set forth in Example 43. Results are reported in Table 1.

EXAMPLE 10

A. Synthesis of 1,5,9-Tris(p-toluenesulfonyl)-1,5,9-triazanonane

To a stirred solution of p-toluenesulfonyl chloride (240 g, 1.26 mole) in pyridine (600 ml) at 0° C. was added a solution of 1,5,9-triazanonane (50.0 g, 0.381 mole) in pyridine (100 ml) under a dry nitrogen atmosphere, maintaining the temperature <60° C. The addition required 15 minutes. The solvent was removed in vacuo and the resulting yellow oil was dissolved in ethyl acetate (1 l) and $H_2O$ (500 ml). The ethyl acetate layer was separated, washed with 0.1 N HCl, $H_2O$ and saturated NaCl solution and dried ($MgSO_4$). The solution was decolorized with silica gel and the solvent was removed in vacuo to give 133 g (59% yield) of the crude product as a glassy solid: $^1H$ NMR ($CDCl_3$) δ 1.71 (quint, J=6.6 Hz, 4H), 2.42 (s, 6H), 2.43 (s, 3H), 2.96 (quart, J=6.4 Hz, 4H), 3.11 (t, J=6.8 Hz, 4H), 5.12 (t, J=6.6 Hz, 2H), 7.30 (m, 6H), 7.63 (m, 2H), 7.73 (m, 4H).

B. Synthesis of 1,5,9-Tris(p-toluenesulfonyl)-1,5,9-triazanonane-1,9-disodium Salt To a stirred solution of 1,5,9-tris(p-toluenesulfonyl)-1,5, 9-triazanonane prepared as in Example 10A (133 g, 0.223 mole) in ethanol (300 ml) heated to reflux under a dry argon atmosphere was added a solution of sodium ethoxide (prepared by dissolving sodium metal (10.8 g, 0.469 mole) in ethanol (300 ml)) as rapidly as possible. After the addition of ethanol (500 ml), the mixture was heated to reflux. The mixture was allowed to cool to room temperature and ethyl ether (200 ml) was added. The crystals were filtered under a dry nitrogen blanket, washed with ethanol and ethyl ether, and then dried in vacuo to give 130 g (92% yield) of the product as an off-white powder: $^1H$ NMR (DMSO-$d_6$) δ 1.37 (br quint, J=5.1 Hz, 4H), 2.29 (s, 6H), 2.37 (s, 3H), 2.48 (t, J=6.3 Hz, 4H), 3.09 (t, J=7.2 Hz, 4H), 7.14 (d, J=7.7 Hz, 4H), 7.33 (d, J=8.1 Hz, 2H), 7.52 (d, J=8.1 Hz, 4H), 7.58 (d, J=8.3 Hz, 2H).

C. Synthesis of 4-Azaheptane-1,7-diol

This compound was synthesized following the procedure of Alcock, N., Curzon, E., Moore, P., Oman, H. and Pierpoint, C., *J. Chem. Soc. Dalton Trans.*, 1361-4 (1985). 3-Amino-1-propanol (50.0 g, 0.666 mole) was stirred at 0° C. under a dry argon atmosphere while methyl acrylate (57.3 g, 0.666 mole) was added dropwise, maintaining the temperature at 0° C. The addition required 1 h. The mixture was then stirred an additional 1 h at room temperature to give a quantitative yield of 3-(3-hydroxypropylamino)methyl propanoate as a pale yellow oil which was used in the next step without purification.

To a stirred solution of lithium aluminum hydride (666 ml-1.0M solution, 0.666 mole) in THF at 0° C. under a dry argon atmosphere was added dropwise a solution of the ester prepared as above (107 g, 0.666 mole) in anhydrous THF (300 ml), maintaining the temperature <10° C. The addition required 2.5 h. The mixture was allowed to warm to room temperature and was stirred for 1 h and then refluxed for 1 h. After stirring the mixture an additional 18 h at room temperature, $H_2O$ (20 ml) was added dropwise, followed by 15% NaOH (20 ml) and then more $H_2O$ (40 ml). The white solid was removed by filtration. The solvent was removed in vacuo to give the crude product as a viscous yellow oil. Fractional vacuum distillation gave 53.6 g (60% yield) of the product as a colorless oil: bp 145° C. (0.4 mm Hg); $^1$H NMR ($CDCl_3$) δ 1.71 (quint, J=6.0 Hz, 4 H), 2.82 (t, J=6.1 Hz, 4H), 3.05 (br s, 3H), 3.76 (t, J=5.6 Hz, 4H).

D. Synthesis of 4-p-Toluenesulfonyl)-4-azaheptane-1,7-di-p-toluenesulfonate

To a stirred solution of p-toluenesulfonyl chloride (253 g, 1.33 mmole) and triethylamine (143 g, 1.41 mole) in $CH_2Cl_2$ (1.0 l) at 0° C. under a dry argon atmosphere was added a solution of 4-azaheptane-1,7-diol prepared as in Example 10C (53.6 g, 0.402 mmole) in $CH_2Cl_2$ (350 ml), maintaining the temperature <10° C. The addition required 15 minutes. The mixture was allowed to warm to room temperature and was stirred an additional 22 h. The mixture was then poured onto ice (1000 g) and the $CH_2Cl_2$ layer was separated. The $CH_2Cl_2$ layer was washed with 1N HCl, $H_2O$ and saturated NaCl solution and was dried ($MgSO_4$). The solvent was removed in vacuo and the resulting yellow oil was washed with hexane. The crude product was purified by recrystallization from ethyl acetate-hexane to give 196 g (82% yield) of the product as colorless needles: mp 76°-8° C.; $^1$H NMR ($CDCl_3$) δ 1.89 (quint, J=8.4 Hz, 4H), 2.43 (s, 3H), 2.46 (s, 6H), 3.08 (t, J=8.5 Hz, 4H), 4.03 (t, J=6.1 Hz, 4H), 7.34 (d, J=8.1 Hz, 2H), 7.36 (d, J=8.3 Hz, 4H), 7.61 (d, J=8.3 Hz, 2H), 7.78 (d, J=8.3 Hz, 4H).

E. Synthesis of 1,5,9,13-Tetra(p-toluenesulfonyl)-1,5,9,13-tetraazacyclohexadecane To a stirred solution of 1,5,9-tris(p-toluenesulfonyl)-1,5,9-triazanonane-1,9-disodium salt prepared as in Example 10B (30.0 g, 0.0470 mole) in anhydrous DMF (470 ml) at 100° C. under a dry argon atmosphere was added dropwise over a 3 h period a solution of 4-(p-toluenesulfonyl)-4-azaheptane-1,7-di-p-toluenesulfonate prepared as in Example 10D (28.0 g, 0.0470 mole) in anhydrous DMF (230 ml) maintaining the temperature at 100° C. After stirring the solution an additional 1 h at 100° C., the mixture was concentrated in vacuo to a volume of 250 ml. $H_2O$ (1750 ml) was slowly added at 50° C to crystallize the product. The resulting pale yellow solid was filtered, washed thoroughly with $H_2O$ and dried in vacuo. The solid was dissolved in $CHCl_3$, and the solution was filtered. The solvent was removed in vacuo. The crude product was purified by recrystallization from DMF-ethanol to give 33.7 g (85% yield) of the product as a white crystalline solid: mp 283.5°-5° C.; $^1$H NMR ($CDCl_3$) δ 2.03 (quint, J=7.0 Hz, 8H), 2.45 (s, 12H), 3.13 (t, J=6.7 Hz, 16H), 7.37 (d, J=8.1 Hz, 8H), 7.67 (d, J=8.3 Hz, 8H).

F. Synthesis of 1,5,9,13-Tetraazacyclohexadecane

A mixture of 1,5,9,13-tetra(p-toluenesulfonyl)-1,5,9,13-tetraazacyclohexadecane prepared as in Example 10E (33.7 g, 0.0399 mole) and concentrated $H_2SO_4$ (100 ml) was heated at 100° C. with stirring under a dry argon atmosphere for 72 h. To the resulting brown solution, ethanol (200 mL) was added dropwise with stirring at 0° C., followed by ethyl ether (500 ml). The tan solid was filtered and washed thoroughly with ethyl ether. The solid was then dissolved in $H_2O$ (50 ml), the pH was adjusted to 11 with solid NaOH, and the solvent was removed in vacuo. The resulting brown oily solid was extracted with hot THF (4×100 ml) and the extracts were filtered. The filtrates were combined and filtered to remove cloudiness. The solvent was removed in vacuo and the crude product was purified by recrystallization from $CHCl_3$-ethyl ether to give 4.29 g (47% yield) of the product as colorless prisms: mp 84°-6° C.; $^1$H NMR ($CDCl_3$) δ 1.54 (br s, 4H), 1.70 (quint, J=6.0 Hz, 8H), 2.72 (t, J=6.1 Hz, 16H); Exact mass (M+H)$^+$: calcd., 229.2391; Found, 229.2417 ($C_{12}H_{29}N_4$).

G. Synthesis of [Manganese(II)1,5,9,13-Tetraazacyclohexadecane)]Chloride

A solution of 1,5,9,13-tetraazacyclohexadecane prepared as in Example 10E (1.0 g, 4.4 mmole) and anhydrous manganese(II) chloride (0.55 g, 4.4 mmole) in anhydrous methanol (60 ml) was refluxed under a dry nitrogen atmosphere for 1 h. Cloudiness was removed by filtration and the solvent was removed in vacuo. The residue was recrystallized from ethanol-ethyl ether to give 0.51 g (33% yield) of the product as a white crystalline solid: FAB mass spectrum (NBA) m/z (relative intensity) 354 (M$^+$, 7), 318/320 ((M−Cl)$^+$, 100/27); Anal. calcd. for $C_{12}H_{28}Cl_2MnN_4$: C, 40.69;H, 7.97; N, 15.82; Cl, 20.02. Found: C, 40.66; H, 7.89; N, 16.59; Cl, 20.05.

EXAMPLE 11

A. Synthesis of 1,5,8,12-Tetra(p-toluenesulfonyl)-1,5,8,12-tetraazadodecane

To a stirred solution of p-toluenesulfonyl chloride (460 g, 2.41 mole) in pyridine (1.5 l) at 0° C. was added a solution of 1,5,8,12-tetraazadodecane (100 g, 0.574 mole) in pyridine (100 ml) under a dry argon atmosphere, maintaining the temperature <50° C. The addition required 1 h. The mixture was allowed to cool to room temperature and was stirred for 2 h. $H_2O$ (3 l) was slowly added to the cooled (ice bath) mixture. The resulting brown solid was filtered and washed thoroughly with $H_2O$. The crude product was purified by recrystallization from DMF-$H_2O$ to give 238 g (53% yield) of the product as a crude granular solid: mp 141°-2° C.; $^1$H NMR ($CDCl_3$) δ 1.78 (quint, J=6.2 Hz, 4H), 2.41 (s, 6H), 2.43 (s, 6H), 2.97 (quart, J=6.6 Hz, 4H), 3.15 (t, J=6.6 Hz, 4H), 3.22 (s, 4H), 5.31 (t, J=6.5 Hz, 2H), 7.28 (d, J=8.3 Hz, 4H), 7.32 (d, J=8.3 Hz, 4H), 7.66 (d, J=8.3 Hz, 4H), 7.72 (d, J=8.3 Hz, 4H).

B. Synthesis of 3-(p-Toluenesulfonyl)-3-azapentane-1,5-di-p-toluenesulfonate To a stirred solution of p-toluenesulfonyl chloride (598 g, 3.14 mole) and triethylamine (318 g, 3.14 mole) in anhydrous $CH_2Cl_2$ (1.5 l) at 5° C. under a dry argon atmosphere was added a solution of diethanolamine (100 g, 0.951 mole) in anhydrous $CH_2Cl_2$ (50 ml) maintaining the temperature <10° C. The addition required 45 minutes. The mixture was allowed to warm to room temperature and was stirred an additional 18 h. $H_2O$ (1.5 l) was then added and the $CH_2Cl_2$ layer was separated. The $CH_2Cl_2$ layer was washed with 10% HCl and $H_2O$ and was dried ($MgSO_4$). The solvent was removed in vacuo to give an off-white solid. The crude product was purified by recrystallization from ethyl acetate-hexane to give 329 g (61% yield) of the product as a white powder: mp 86°–7.5° C.; $^1H$ NMR ($CDCl_3$) δ 2.42 (s, 3H), 2.46 (s, 6H), 3.37 (t, J=6.0 Hz, 4H), 4.11 (t, J=6.0 Hz, 4H), 7.29 (d, J=7.7 Hz, 2H), 7.36 (d, J=8.0 Hz, 4H), 7.62 (d, J=8.4 Hz, 2H), 7.77 (d, J=8.3 Hz,4H).

C. Synthesis of 1,4,7,11,14-Penta(p-toluenesulfonyl)-1,4,7,11,14-pentaazacyloheptadecane To a stirred solution of 1,5,8,12-tetra(p-toluenesulfonyl)-1,5,8,12-tetraazadodecane prepared as in Example 11A (36.9 g, 0.0467 mole) in anhydrous DMF (470 ml) was added sodium hydride (2.80 g-80% in mineral oil, 0.0933 mole) in portions under a dry nitrogen blanket. The resulting mixture was stirred for 30 minutes under a dry argon atmosphere. The solution was then heated to 100° C. and a solution of 3-(p-toluenesulfonyl)-3-azapentane-1,5-di-p-toluenesulfonate prepared as in Example 11B (26.5 g, 0.0467 mole) in anhydrous DMF (230 mole) was added dropwise over a 3 h period, maintaining the temperature at 100° C. After stirring the solution an additional 1 h at 100° C., the mixture was concentrated in vacuo to a volume of 400 ml. $H_2O$ (1.5 l) was slowly added at room temperature to crystallize the product. The resulting pale yellow solid was filtered, washed thoroughly with $H_2O$ and dried in vacuo. The crude product was purified by recrystallization from $CH_2Cl_2$-hexane to give 26.3 g (55% yield) of the product as a white crystalline solid: mp 235.5°–6.5° C. (dec.); $^1H$ NMR ($CDCl_3$) δ 2.09 (quint, J=6.6 Hz, 4H), 2.44 (s, 6H), 2.45 (s, 6H), 2.46 (s, 3H), 3.04 (t, J=7.5 Hz, 4H), 3.13 (t, J=7.1 Hz, 4H), 3.23 (m, 8H), 3.45 (m, 4H), 7.33 (m, 10H), 7.72 (m, 10H).

D. Synthesis of 1,4,7,11,14-Pentaazacycloheptadecane

A mixture of 1,4,7,11,14-penta(p-toluenesulfonyl)-1,4,7,11,14-pentaazacyclopentadecane prepared as in Example 11C (26.3 g, 0.0258 mole) and concentrated $H_2SO_4$ (80 ml) was heated at 100° C. with stirring under a dry argon atmosphere for 72 h. To the resulting brown solution, ethanol (160 mL) was added dropwise with stirring at 0° C. followed by ethyl ether (400 ml). The resulting tan solid was filtered and dried in vacuo over $P_2O_5$. The tarry solid was then dissolved by the addition of 10N NaOH and the salts were removed by filtration. The solution was then extracted with $CHCl_3$ (6×200 ml). The extracts were combined, dried ($Na_2SO_4$) and the solvent was removed in vacuo to give an oil which crystallized on standing. The crude product was dissolved in hexane and insoluble impurities were removed by filtration. Upon cooling to –20° C., 2.28 g (36% yield) of the product was obtained as colorless needles: mp 49°–51° C.; $^1H$ NMR ($CDCl_3$) δ 1.69 (m, 4H), 1.78 (br s, 5H), 2.76 (m, 20H). Exact mass: (M+H)$^+$: calcd., 244. 2501; Found: 244.2557 ($C_{12}H_{30}N_5$).

E. Synthesis of [Manganese(II)(1,4,7,11,14-Pentaazacycloheptadecane)]Chloride A solution of 1,4,7,11,14-pentaazacyloheptadecane prepared as in Example 11D (0.70 g, 2.9 mmole) and anhydrous manganese(II) chloride (0.36 g, 2.9 mmole) in anhydrous methanol (50 ml) was refluxed under a dry nitrogen atmosphere for 2 h. The solution was filtered and concentrated in vacuo to a volume of 20 ml. Ethyl ether (5 ml) was added and upon cooling to 0° C., 0.80 g (75% yield) of the product was obtained as a white crystalline solid: FAB mass spectrum (NBA) m/z (relative intensity); 333/335 [(M–Cl)$^+$, 100/30]Anal. calcd. for $C_{12}H_{29}Cl_2MnN_5$: C, 39.03; H, 7.92; N, 18.97; Cl, 19.20. Found: C, 38.72; H, 7.78; N, 19.54, Cl, 18.53.

EXAMPLE 2

A. Synthesis of 1,4,7,10,14-penta(p-toluenesulfonyl)-1,4,7,10,14-pentaazacycloheptadecane To a stirred solution of 1,5,9-tris(p-toluenesulfonyl)-1,5,9-triazanonane-1,9-disodium salt prepared as in Example 10B (31.9 g, 0.0500 mole) in anhydrous DMF (500 ml) at 100° C. under a dry argon atmosphere was added dropwise over a 3 h period a solution of 3,6-bis(p-toluenesulfonyl)-3,6-diazaoctane-1,8-di-p-toluenesulfonate prepared as in Example 1C (38.3 g, 0.0500 mole) in anhydrous DMF (250 ml), maintaining the temperature at 100° C. After stirring an additional 1 h at 100° C., the solution was concentrated in vacuo to a volume of 300 ml. Ethanol (500 ml) was slowly added. The mixture was refluxed for 15 minutes and $H_2O$ (1 l) was added to the slurry. The resulting yellow solid was filtered and washed thoroughly with $H_2O$. The solid was dissolved in $CHCl_3$. The $CHCl_3$ solution was washed with $H_2O$, saturated NaCl solution and was dried ($Na_2SO_4$). The solvent was removed in vacuo and the crude product was purified by flash chromatography (silica gel, $CHCl_3$-97:3 (v/v) $CHCl_3$-MeOH gradient) to give 28.5 g (56% yield) of the product as an amorphous white solid: Rf=0.16, silica gel-$CHCl_3$; $^1H$ NMR ($CDCl_3$) δ 1.92 (quint, J=7.3 Hz, 4H), 2.42 (s, 3H), 2.44 (s, 12H), 3.04 (t, J=7.0 Hz, 4H), 3.17 (m, 8H), 3.31 (m, 4H), 3.37 (s, 4H), 7.32 (m, 10H), 7.62 (d, J=8.3 Hz, 2H), 7.69 (m, 8H).

B. Synthesis of 1,4,7,10,14-pentaazacycloheptadecane

A mixture of 1,4,7,10,14-penta(p-toluenesulfonyl)-1,4,7,10,14-pentaazacycloheptadecane prepared as in Example 12A (28.5 g, 0.0279 mole) and concentrated $H_2SO_4$ (100 ml) was heated at 100° C. with stirring under a dry argon atmosphere for 72H. To the resulting brown solution, ethanol (100 ml) was added dropwise with stirring at 0° C. followed by ethyl ether (1 l). The tan solid was filtered and washed thoroughly with ethyl ether. The solid was then dissolved in $H_2O$ (100 ml) and the resulting solution filtered and washed with ethyl ether. The pH of the solution was adjusted to 11 with 10N NaOH and the solvent was removed in vacuo. The resulting brown oily solid was extracted with hot THF (2×500 ml) and the THF extracts were filtered. The filtrates were combined and the solvent was removed in vacuo. The oily residue was dissolved in hot hexane and the insoluble impurities were removed by filtration. The solvent was removed in vacuo and the residual oil was purified by vacuum distillation to give 2.68 g (39% yield) of the product as a light yellow oil: bp 140°–5° C. (0.10 mm Hg); $^1H$ NMR ($CDCl_3$) δ 1.51 (br s, 5 H), 1.68 (quint, J=6.1 Hz, 4H), 2.73

(m, 20H); Exact mass (M+H)$^+$: calcd., 244.2501; Found: 244.2555 ($C_{12}H_{30}N_5$).

C. Synthesis of [Manganese(II)(1,4,7,10,14-Pentaazacycloheptadecane)]Chloride A solution of 1,4,7,10,14-pentaazacycloheptadecane prepared as in Example 12B (1.0 g, 4.3 mmole) and anhydrous manganese(II) chloride (0.54 g, 4.3 mmole) in anhydrous methanol was stirred under a dry nitrogen atmosphere for 16 h. Insoluble impurities were removed by filtration and the solution was concentrated in vacuo to a volume of 6 ml. Upon standing, 0.71 g (45% yield) of the product was obtained as a white crystalline solid: FAB mass spectrum (NBA) m/z (relative intensity) 333/335 [(M–Cl)$^+$, 100/32]; Anal. calcd. for $C_{12}H_{29}Cl_2MnN_5 \cdot H_2O$: C, 37.22; H, 8.07; N, 18.09; Cl, 18.31. Found: C, 36.81; H, 7.75; N, 17.62; Cl, 18.30.

EXAMPLE 13

A. Synthesis of [Manganese(II)[1,4,7,10,13,16-hexaazacyclooctadecane)]Chloride A solution of 1,4,7,10,13,16-hexaazacyclooctadecane (0.47 g, 1.8 mmole) and anhydrous manganese(II) chloride (0.23 g, 1.8 mmole) in anhydrous methanol (50 ml) was refluxed under a dry nitrogen atmosphere overnight. The solution was filtered and the solvent was removed in vacuo. The solid was recrystallized from ethanol-ethyl ether to give 0.54 g (77% yield) of the product as a white crystalline solid: FAB mass spectrum (NBA) m/z (relative intensity) 348/350 ((M–Cl)$^+$, 100/27); Anal. calcd. for $C_{12}H_{30}Cl_2MnN_6$: C, 36.51; H, 7.87; N, 21.87; Cl, 18.45. Found: C, 36.14; H, 7.95; N, 20.93; Cl, 17.91.

EXAMPLE 14

A. Synthesis of 1,4,7,10,13,16,19-heptaazacycloheneicosane

A mixture of 1,4,7,10,13,16,19-hepta(p-toluenesulfonyl)-1,4,7,10,13,16,19-heptaazacycloheneicosane (28.3 g, 0.0205 mole) and concentrated $H_2SO_4$ (85 ml) was heated at 100° C. with stirring under a dry argon atmosphere for 4 days. To the resulting solution, ethanol (170 mL) was added dropwise with stirring at 0° C., followed by ethyl ether (430 ml). The solid was filtered and dried in vacuo over $P_2O_5$. The solid was then dissolved in $H_2O$ (75 ml) and the pH of the solution was adjusted to 10 with 10N NaOH. Insoluble impurities were removed by filtration and the solution was extracted with 6×$CHCl_3$. The extracts were combined, dried ($Na_2SO_4$) and the solvent removed in vacuo to give a yellow oil which crystallized on standing. The aqueous layer was taken to dryness in vacuo and the resulting brown oily solid was extracted with hot THF (2×500 ml). The THF extracts were filtered and combined with the yellow solid obtained above. Insoluble impurities were removed by filtration and the solvent was removed in vacuo to give a yellow crystalline solid. The crude solid was crystallized from $CHCl_3$-acetonitrile to give 505 mg (8% yield) of the product as colorless needles: mp 163°-5° C.; $^1$H NMR ($CDCl_3$) δ 2.99 (s, 28H), 4.00 (br s, 7H); Exact mass (M+H)$^+$: calcd., 302.3032; Found: 302.3097 ($C_{14}H_{36}N_7$).

B. Synthesis of [Manganese(II)[1,4,7,10,13,16,19-Heptaazaacycloheneicosane)]Chloride A solution of 1,4,7,10,13,16,19-heptaazacycloheneicosane prepared as in Example 14A (0.38 g, 1.4 mmole) and anhydrous manganese(II) chloride (0.18 g, 1.4 mmole) in anhydrous methanol was refluxed under a dry nitrogen atmosphere for 1.5 h. Solvent was removed in vacuo to near dryness to give upon standing 0.097 g (17% yield) of the product as a white solid: FAB mass spectrum (NBA) m/z (relative intensity) 427 (M$^+$, 14), 391/393 [(M–Cl)$^+$, 100/36]; Exact mass (M–Cl)$^+$: calcd., 391.2023; Found: 391.2015 ($C_{14}H_{35}ClMnN_7$).

EXAMPLE 15

A. Synthesis of N-Methylbis(2-chloroethyl)amine

To a stirred solution of N-methylbis(2-chloroethyl)amine hydrochloride (25.0 g, 0.130 mole) in $H_2O$ (125 ml) was added 1N NaOH (125 ml) and the resulting solution was extracted with $CH_2Cl_2$. The extracts were combined and dried ($MgSO_4$) and the solvent was removed in vacuo to give 20.2 g (100% yield) of the product as a colorless liquid: $^1$H NMR ($CDCl_3$) δ 2.37 (s, 3H), 2.82 (t, J=6.9 Hz, 4H), 3.56 (t, J=6.9 Hz, 4H).

B. Synthesis of 1,4,7,10-Tetra(p-toluenesulfonyl)-1,4,7,10-tetraazadecane

To a stirred solution of p-toluenesulfonyl chloride (285 g, 1.50 mole) in pyridine (650 ml) at 5° C. was added a solution of 1,4,7,10-tetraazadecane (48.0 g, 0.328 mole) in pyridine (200 ml) under a dry argon atmosphere maintaining the temperature <20° C. The mixture was stirred for 3 days at room temperature. $H_2O$ (1 l) was slowly added to the cooled (ice bath) mixture. The solid was filtered, washed thoroughly with $H_2O$ and dried in vacuo to give 225 g (90% yield) of the product as a powder: mp 222°-4° C.; $^1$H NMR (DMSO-$d_6$) δ 2.38 (s, 6H), 2.41 (s, 6H), 2.84 (quart, J=6.6 Hz, 4H), 3.07 (t, J=7.0 Hz, 4H), 3.12 (s, 4H), 7.40 (m, 8H), 7.66 (m, 8H).

C. Synthesis of 1-Methyl-4,7,10,13-tetra(p-toluenesulfonyl)-1,4,7,10,13-pentaazacyclopentadecane To a stirred solution of 1,4,7,10-tetra(p-toluenesulfonyl)-1,4,7,10-tetraazadecane prepared as in Example 15B (66.5 g, 0.0872 mole) in anhydrous DMF (1 l) was added sodium hydride (5.22 g-80% in mineral oil, 0.174 mole) in portions under a dry nitrogen blanket. The resulting mixture was stirred for 30 minutes under a dry argon atmosphere. The solution was then heated to 100° C. and a solution of N-methylbis(2-chloroethyl)amine freshly prepared as in Example 15A (13.6 g, 0.0872 mole) in anhydrous DMF (200 ml) was added dropwise over a 1.5 h period, maintaining the temperature at 100° C. After stirring an additional 45 minutes at 100° C., the solution was concentrated in vacuo to a volume of 750 ml. $H_2O$ was slowly added at room temperature to crystallize the product. The resulting brown solid was filtered, washed thoroughly with $H_2O$ and dried in vacuo over $P_2O_5$ to give 62.9 g (85% yield) of the crude product as a brown solid. The product was purified by crystallization from DMF-$H_2O$ to give a yellow solid: mp 170°-1° C.; $^1$H NMR ($CDCl_3$) δ 2.15 (s, 3H), 2.43 (s, 6H), 2.44 (s, 6H), 2.51 (t, J=5.5 Hz, 4H), 3.15 (t, J=5.5 Hz, 4H), 3.29 (m, 8H), 3.36 (s, 4H), 7.32 (m, 8H), 7.69 (m, 8H).

D. Synthesis of 1-Methyl-1,4,7,10,13-pentaazacyclo-pentadecane

A mixture of 1-methyl-4,7,10,13-tetra(p-toluenesulfonyl)-1,4,7,10,13-pentaazacyclopentadecane prepared as in Example 15C (3.6 g, 4.3 mmol) and concentrated $H_2SO_4$ (15 ml) was heated at 100° C. with stirring under a dry argon atmosphere for 72 h. To the resulting brown solution, ethanol (30 mL) was added dropwise with stirring at 5° C. followed by ethyl ether (80 ml). The tan solid was filtered and dissolved in $H_2O$ (10 ml). The pH of the solution was adjusted to 10 with 10N NaOH and the solution was extracted with 6×$CHCl_3$. The extracts were combined, dried ($Na_2SO_4$) and the solvent removed in vacuo. The crude solid was purified by crystallization from cold (−20° C.) $CH_3CN$ to give 0.50 g (51% yield) of the product as colorless needles: mp 71.0°–2.5° C.; $^1H$ NMR ($CDCl_3$) δ 1.90 (br s, 4H), 2.22 (s, 3 H), 2.52 (m, 4H), 2.68 (m, 12H), 2.78 (m, 4H); Anal. calcd. for $C_{11}H_{27}N_5$: C, 57.60; H, 11.86; N, 30.53. Found: C, 57.17; H, 12.13; N, 30.12.

E. Synthesis of [Manganese(II)(1-Methyl-1,4,7,10,13-pentaazacyclopentadecane)]Chloride A solution of 1-methyl-1,4,7,10,13-pentaazacyclopentadecane prepared as in Example 15D (0.32 g, 1.4 mmole) and anhydrous manganese(II) chloride (0.18 g, 1.4 mmole) in anhydrous methanol (40 ml) was refluxed under a dry nitrogen atmosphere for 2 h. The solution was filtered and the solvent was removed in vacuo. The residue was recrystallized from ethanol-ethyl ether to give 70 mg (14% yield) of the product as a white solid: FAB mass spectrum (NBA) m/z (relative intensity) 319/321 [(M−Cl)$^+$, 100/30); Exact mass (M−Cl)$^+$: calcd., 319.1336; Found: 319.1338 ($C_{11}H_{27}ClMnN_5$).

EXAMPLE 16

A. Synthesis of 1,4,8,11-Tetra(p-toluenesulfonyl)-1,4,8,11-tetraazaundecane

To a stirred solution of p-toluenesulfonyl chloride (262 g, 1.37 mole) in anhydrous pyridine (600 ml) at 5° C. was added a solution of 1,4,8,11-tetraazaundecane (49.1 g, 0.306 mole) in anhydrous pyridine (200 ml) under a dry argon atmosphere, maintaining the temperature <20° C. The addition required 1 h. The mixture was stirred overnight at room temperature. $H_2O$ (1.5 l) was slowly added to the cooled (ice bath) mixture. The resulting oil was dissolved in $CH_2Cl_2$, separated from the aqueous layer. The $CH_2Cl_2$ layer was washed with 5% HCl and $H_2O$ and dried ($MgSO_4$). The solvent was removed in vacuo to give an oil which solidified on standing. The resulting solid was ground to a powder and dried in vacuo to give 186 g (78% yield) of the crude product: $^1H$ NMR ($CDCl_3$) δ 1.98 (quint, J=7.3 Hz, 2H), 2.40 (s, 6H), 2.42 (s, 6H), 3.11 (t, J=7.3 Hz, 4H), 3.17 (s, 8H), 5.76 (t, J=6.0 Hz, 2H), 7.29 (m, 8H), 7.64 (d, J=8.3 Hz, 4H), 7.75 (d, J=8.3 Hz, 4H).

B. Synthesis of 1-Methyl-4,7,11,14-tetra(p-toluenesulfonyl)-1,4,7,11,14-pentaazacyclohexadecane To a stirred solution of 1,4,8,11-tetra(p-toluenesulfonyl)-1,4,8,11-tetraazaundecane prepared in Example 16A (80.7 g, 0.104 mole) in anhydrous DMF (1 l) was added sodium hydride (6.24 g-80% in mineral oil, 0.208 mole) in portions under a dry nitrogen blanket. The resulting mixture was stirred for 30 minutes under a dry argon atmosphere. The solution was then heated to 100° C. and a solution of N-methylbis(2-chloroethyl)amine freshly prepared as in Example 15A (16.2 g, 0.104 mole) in anhydrous DMF (200 ml) was added dropwise over a 45 minute period, maintaining the temperature at 100° C. After stirring, an additional 45 minutes at 100° C., the solution was concentrated in vacuo to a volume of 900 ml. $H_2O$ (1200 ml) was added at room temperature to crystallize the product. The solid was dried in vacuo over $P_2O_5$ to give 83.2 g (93% yield) of the crude product as a brown solid. A portion (50 g) of the crude product was purified by flash chromatography (silica gel, $CHCl_3$-95:5 (v/v)-$CHCl_3$-MeOH gradient) to give 16.8 g (34% yield) of the product as a light yellow solid. An analytical sample was recrystallized from $CH_2Cl_2$-hexane: mp 183°–5° C.; $R_f$=0.60, silica gel-95:5 (v/v) $CHCl_3$-MeOH; $^1H$ NMR ($CDCl_3$) δ 1.91 (quint, J=6.0 Hz, 2H), 2.19 (s, 3H), 2.44 (s, 12H), 2.52 (t, J=6.2 Hz, 4H), 3.18 (m, 12H), 3.31 (m, 4H), 7.33 (m, 8H), 7.68 (m, 8H).

C. Synthesis of 1-Methyl-1,4,7,11,14-pentaazacyclohexadecane

A mixture of 1-methyl-4,7,11,14-penta(p-toluenesulfonyl)-1,4,7,11,14-pentaazacyclohexadecane prepared as in Example 16B (16.3 g, 0.0190 mole) and concentrated $H_2SO_4$ (100 ml) was heated at 100° C. with stirring under a dry argon atmosphere for 64 h. To the resulting brown solution, ethanol (200 mL) was added dropwise with stirring at 5° C., followed by ethyl ether (500 ml). The tan solid was filtered and dissolved in $H_2O$ (75 ml). The pH of the solution was adjusted to 10 with 10N NaOH and the solution was extracted with 6×$CHCl_3$. The extracts were combined, dried ($Na_2SO_4$) and the solvent was removed in vacuo. The crude product was purified by crystallization from cold (−20° C.) $CH_3CN$ to give 756 mg (15% yield) of the product as a white crystalline solid: mp 85°–7° C.; $^1H$ NMR ($CDCl_3$) 1.73 (quint, J=5.3 Hz, 2H), 2.11 (br s, 4H), 2.16 (s, 3H), 2.51 (m, 4H), 2.73 (m, 16H). Anal. calcd. for $C_{12}H_{29}N_5$: C, 59.22; H, 12.01; N, 28.77. Found: C, 59.46; H, 11.90; N, 28.75.

D. Synthesis of [Manganese(II)(1-Methyl-1,4,7,11,14-pentaazacyclohexadecane)]Chloride A solution of 1-methyl-1,4,7,11,14-pentaazacyclohexadecane prepared as in Example 16C (0.65 g, 2.7 mmole) and anhydrous manganese(II) chloride (0.33 g, 2.7 mmole) in anhydrous methanol (50 ml) was refluxed under a dry nitrogen atmosphere for 2 h. The solution was filtered and the solvent was removed in vacuo. The residue was recrystallized from ethanol-ethyl ether to give 800 mg (82% yield) of the product as a white crystalline solid: FAB mass spectrum (NBA) m/z (relative intensity) 333/335 ((M−Cl)$^+$, 100/29); Anal. calcd. for $C_{12}H_{29}Cl_2MnN_5$ C, 39.03; H, 7.92; N, 18.97; Cl, 19.20. Found: C, 38.67; H, 7.85; N, 18.80; Cl, 19.38.

EXAMPLE 17

A. Synthesis of 4,7,10,13-Tetra(p-toluenesulfonyl]-1-oxa-4,7,10,13-tetraazacyclopentadecane To a stirred solution of 1,4,7,10-tetra(p-toluenesulfonyl)-1,4,7,10-tetraazadecane prepared as in Example 15B (35.3 g, 0.0463 mole) in anhydrous DMF (460 ml) was added sodium hydride (2.77 g-80% in mineral oil, 0.0925 mole) in portions and the resulting mixture was stirred for 30 minutes under a dry argon atmosphere. The solution was then heated to 100° C. and a solution of 2-chloroethyl ether (6.61 g, 0.0463 mole) in anhydrous DMF (90 ml) was added dropwise over a 1.5 h period, maintaining the temperature at 100° C. After stirring the solution an additional 1.5 h at 100° C., $H_2O$ (3 l) was added while cooling (ice bath) to crystallize the product. The resulting tan solid was filtered and dried in vacuo. The crude product was purified by crystallization from $CH_2Cl_2$-hexane to give 13.2 g (34% yield) of the product as an off-white solid: mp 197.5°–201°C.; $^1$H NMR ($CDCl_3$) δ 2.44 (s, 12H), 3.28 (m, 16H), 3.57 (m, 4H), 7.35 (m, 8H), 7.69 (m, 8H).

B. Synthesis of 1-oxa-4,7,10,13-tetraazacyclopentadecane

A mixture of 4,7,10,13-tetra(p-toluenesulfonyl)-1-oxa-4,7,10,13-tetraazacyclopentadecane prepared as in Example 17A (10.9 g, 0.0131 mole) and concentrated $H_2SO_4$ (70 ml) was heated at 100° C. with stirring under a dry argon atmosphere for 70 h. To the resulting brown solution, ethanol (140 ml) was added dropwise with stirring at 5° C., followed by ethyl ether (340 ml). The gummy brown solid was filtered and dissolved in $H_2O$ (100 ml). The pH of the solution was adjusted to 10 with 10N NaOH and the solution was extracted with 6×100 ml $CHCl_3$. The extracts were combined, dried ($Na_2SO_4$) and the solvent removed in vacuo. The crude product was purified by crystallization from hexane to give 0.49 g (17% yield) of the product as colorless needles: mp 80°–1° C.; $^1$HNMR ($CDCl_3$) δ 1.98 (br s, 4H), 2.76 (m, 16H), 3.61 (m, 4 H); Exact mass (M+H)$^+$: calcd., 217.2028; Found: 217.2051 ($C_{10}H_{25}N_4O$).

C. Synthesis of [Manganese(II)[1-oxa-4,7,10,13-Tetrazacyclopentadecane)]Chloride A solution of 1-oxa-4,7,10,13-tetraazacyclopentadecane prepared as in Example 17B (0.42 g, 1.9 mmole) and anhydrous manganese(II)chloride (0.24 g, 0.19 mmole) in anhydrous methanol was refluxed under a dry nitrogen atmosphere for 2 h. The solution was concentrated in vacuo to a volume of 5 ml and ethyl ether (30 ml) was added. Upon standing, 0.39 g (59% yield) of the product was obtained as a white solid: FAB mass spectrum (NBA) m/z (relative intensity) 306/308 ((M–Cl)$^+$, 100/28); Anal. calcd. for $C_{10}H_{24}Cl_2MnN_4O$: C, 35.10; H, 7.07; N, 16.37; Cl, 20.72. Found: C, 34.18; H, 7.07; N, 15.93; Cl, 20.83.

EXAMPLE 18

A. Synthesis of 1,4,8,12-Tetramethyl-1,4,8,12-tetraazacyclopentadecane

To a stirred solution of 88% aqueous formic acid (30 ml, 0.66 mole) and 37% aqueous formaldehyde (22 ml, 0.30 mole) was added 1,4,8,12-tetraazacyclopentadecane (5.0 g, 0.023 mole) in portions over 15 minutes under an argon atmosphere. $H_2O$ (3.0 ml) was then added and the mixture was refluxed for 20 h. Upon addition of $H_2O$ (30 ml), the mixture was cooled (ice bath) while the pH was adjusted to 12 with 10N NaOH, keeping the temperature <20° C. The solution was extracted with 5×75 ml $CHCl_3$, the extracts were combined and dried ($Na_2SO_4$) and the solvent was removed in vacuo. The resulting yellow oil was purified by distillation in vacuo to give 2.6 g (41% yield) of the product as a colorless oil: bp 80°–6° C. (0.05 mm Hg); $^1$H NMR ($CDCl_3$) δ 1.63 (sext, J=7.5 Hz, 6H), 2.22 (s, 6H), 2.25 (s, 6H), 2.43 (m, 16H); Anal. calcd. for $C_{15}H_{34}N_4$, C, 66.61; H, 12.67; N, 20.72. Found: C, 66.25; H, 12.16; N, 20.33.

B. Synthesis of [Manganese(II) 1,4,8,12-tetramethyl-1,4,8,12-tetraazacyclopentadecane))] Chloride A solution of 1,4,8,12-tetramethyl-1,4,8,12-tetraazacyclopentadecane prepared as in Example 18A (1.0 g, 3.7 mmole) and anhydrous manganese(II) chloride (0.46 g, 3.7 mmole) in anhydrous methanol (75 ml) was stirred at room temperature for 2.3 h and then refluxed for 2 h. The resulting milky solution was filtered hot and solvent removed in vacuo reducing the volume to 5 ml. The resulting white solid was purified by recrystallization from methanol-ethyl ether to give 0.81 g (54% yield) of the product as a white crystalline solid: FAB mass spectrum (NBA) m/z (relative intensity) 395 (M$^+$, 8), 360/362 ((M–Cl)$^+$, 100/38); Anal. calcd. for $C_{15}H_{34}Cl_2MnN_4$: C, 45.46; H, 8.65; N, 14.14; Cl, 17.89. Found: C, 45.04; H, 8.69; N, 13.78; Cl, 18.90.

EXAMPLE 19

A. Synthesis of 1,4,7,10,13-pentamethyl-1,4,7.10.13-pentaazacyclopentadecane To a stirred solution of 88% aqueous formic acid (13 ml, 0.33 mole) and 1,4,7,10,13-pentaazacyclopentadecane prepared as in Example 1E (2.0 g, 9.3 mmol) was added 37% aqueous formaldehyde (12 ml, 0.15 mole) over a 5 minute period under an argon atmosphere. $H_2O$ (1.5 ml) was then added and the mixture was refluxed for 39 h. Upon the addition of $H_2O$ (10 ml), the mixture was cooled (ice bath) while the pH was adjusted to 12 with 10N NaOH, keeping the temperature <20° C. The solution was extracted with 3×50 ml $CH_2Cl_2$, the extracts were combined and dried ($Na_2SO_4$), and the solvent was removed in vacuo. The resulting yellow oil was purified by distillation in vacuo to give 1.3 g (48% yield) of the product as a colorless oil: bp 105°–7° C. (0.15 mm Hg); $^1$H NMR ($CDDl_3$) δ 2.26 (s, 20 H), 2.54 (s, 15 H); FAB mass spectrum (NBA-HCl)) m/z (relative intensity) 286[(M+H)$^+$, 100].

B. Synthesis of [Manganese(II)1,4,7,10,13-pentamethyl-1,4,7,10,13-pentaazacyclopentadecan)] Chloride A solution of 1,4,7,10,13-pentamethyl-1,4,7,10,13-pentaazacyclopentadecane prepared as in Example 19A (0.97 g, 3.4 mmole) and anhydrous manganese(II) chloride (0.42 g, 3.4 mmole) in anhydrous methanol (75 ml) was refluxed under a dry nitrogen atmosphere for 2 h. The solvent was removed in vacuo. The oily residue was recrystallized from ethanol-ethyl ether to give 1.14 g (82% yield) of the product as a white crystalline solid: FAB mass spectrum (NBA) m/z (relative intensity) 411 (M$^+$, 2), 375/377 [(M–Cl)$^+$, 100/32]; Exact mass (M–Cl)$^+$: calcd., 375.1962; Found: 375. 1898 ($C_{15}H_{35}ClMnN_5$).

EXAMPLE 20

Synthesis of [Manganese(II)(1,4,8,11-Tetraazacyclotetradecane)] Chloride

To a refluxing solution of anhydrous manganese(II) chloride (1.00 g, 8.0 mmole) in anhydrous methanol (100 ml) was added 1,4,8,11-tetraazacyclotetradecane (1.58 g, 8.0 mmol) under a dry nitrogen atmosphere. A white solid precipitated and the resulting slurry was refluxed overnight. The solid was filtered, washed with methanol and then ethyl ether to give 2.35 g (91% yield) of the product as a white solid: FAB mass spectrum (NBA—HCl) m/z (relative intensity) 325 (M$^+$, 4), 290/292 [(M–Cl)$^+$, 100/32); Anal. calcd. for $C_{10}H_{24}Cl_2MnN_4$; C, 36.87; H, 7.43; N, 17.20; Cl, 21.77. Found: C, 36.61; H, 7.62; N, 17.12; Cl, 21.01.

EXAMPLE 21

Synthesis of [Manganese(II)(1,4,8,12-Tetraazacyclopentadecane)] Chloride

To a stirred solution of anhydrous manganese(II) chloride (0.50 g, 4.0 mmol) in hot anhydrous methanol (100 ml) was added 1,4,8,12-tetraazacyclopentadecane (0.85 g, 4.0 mmole) under a dry nitrogen atmosphere and the resulting solution was refluxed for 3 h. Solvent was removed in vacuo to a volume of 20 ml. The precipitate which formed was filtered to give 0.56 g (45% yield) of the product as a white solid: FAB mass spectrum (NBA—HCl) m/z (relative intensity) 339 ($M^+$, 5), 304/306 (($M-Cl)^+$, 100/30); Exact mass $(M-Cl)^{3O}$: calcd., 304.1177; Found: 304.1160 ($C_{11}H_{26}ClMnN_4$).

EXAMPLE 22

A. Synthesis of [Manganese(II)(5,7,7,12,14,14-Hexamethyl-1,4,8,11-tetraazacyclotetradeca-4,11-diene] Chlorohexafluorophosphate A slurry of 5,7,7,12,14,14-hexamethyl-1,4,8,11 tetraazacyclotetradeca-4,11-diene hexafluorophosphate (4.5 g, 7.9 mmol) and anhydrous manganese(II) chloride (1.0 g, 7.9 mmol) in anhydrous methanol (200 ml) was heated to reflux under a dry nitrogen atmosphere and diisopropylethylamine (2.0 g, 16 mmol) was added dropwise with vigorous stirring, resulting in a white precipitate. The slurry was refluxed for 3 h and then filtered. The solid was washed with ethyl ether and desiccated in vacuo to give the product as a white solid: FAB mass spectrum (NBA—HCl) m/z (relative intensity) 370/372 [$(M-PF_6)^+$, 100/31]; Anal. calcd. for $C_{16}H_{32}ClMN_4PF_6$: C, 37.44; H, 6.28; N, 10.92; Cl, 6.91. Found: C, 36,43; H, 6.28; N, 10.96; Cl, 6.54.

B. Synthesis of [Manganese(II)(5,7,7,12,14,14-Hexamethyl-1,4,8,11-tetraazacyclotradeca-4,11-diene)] Chloride To a solution of manganese(II) [5,7,7,12,14,14-hexamethyl-1,4,8,11-tetraazacyclotetradeca-4,11-diene] chlorohexafluorophosphate prepared as in Example 22A (1.0 g, 1.9 mmole) in hot acetonitrile (50 ml) was added dropwise anhydrous methanol (5 ml) containing lithium chloride (0.08 g, 1.9 mmole) under a dry nitrogen atmosphere. The resulting solution was cooled and concentrated in vacuo to a volume of 20 ml. Upon standing, 0.36 g (47% yield) of the product was obtained as a white crystalline solid: FAB mass spectrum (NBA—HCl) m/z (relative intensity) 370/372 [$(M-Cl)^+$, 100/29); Exact mass $(M-Cl)^+$: calcd., 370.1696; Found: 370.1679 ($C_{16}H_{32}ClMnN_4$).

EXAMPLE 23

Synthesis of Manganese(II)(2,12-Dimethyl-3,7,11, 17-tetraazabicyclo[11.3.1]heptadeca-1(17),2,11,13, 15-pentaene)] Chloride To a stirred solution of anhydrous manganese(II) chloride (2.5 g, 20 mmole) in anhydrous methanol (210 ml) was added a solution of 2,6-diacetylpyridine (3.3 g, 20 mmole) in anhydrous methanol (40 ml). The mixture was warmed while stirring for 30 minutes and 1,5,9-triazanonane (2.4 g, 19 mmole) was added. The mixture was refluxed for 3 h, and the solvent was removed in vacuo. The resulting solid was extracted with hot ethanol (100 ml) and the extracts were combined and filtered. The solvent was removed in vacuo to give the product as a brown solid: FAB mass spectrum (NBA) m/z (relative intensity) 348/350 [$(M-Cl)^+$, 100/35]; Anal. Calcd. for $C_{15}H_{22}Cl_2MnN_4$. 1.5 $H_2O$: C, 43.81; H 5.39; N, 13.33; Cl, 17.26. Found: C, 43.98, H, 5.72; N, 12.41; Cl, 18.15.

EXAMPLE 24

Synthesis of [Manganese(II) (2,7,12-Trimethyl-3,7, 11,17-tetraazabicyclo[11.3.1]heptadeca-1(17),2,11, 13,15-pentaene)]Chloride To a stirred solution of anhydrous manganese(II) chloride (2.5 g, 20 mmole) in anhydrous methanol (250 ml) was added 2,6-diacetylpyridine (3.3 g, 20 mmole). The mixture was warmed while stirring for 30 minutes and 5-methyl-1, 5,9-triazanonane (2.7 g, 19 mmole) was then added. The mixture was refluxed for 3 h, filtered while hot, and the filtrate was taken to dryness in vacuo. The resulting brown solid was extracted with hot ethanol (4×100 ml) and the extracts were filtered. The extracts were combined and the solvent was removed in vacuo. The crude product was dissolved in hot methanol (50 ml). Insoluble impurities were removed by filtration and $CH_3CN$ (50 ml) added. The solution was concentrated in vacuo and cooled in ice. An amorphous solid was removed by filtration. The filtrate was concentrated to 5 ml and $CH_3CN$ (50 ml) was added. The precipitate which formed was filtered and dried in vacuo to give the product as an orange-red crystalline solid: FAB mass spectrum (NBA—HCl) m/z (relative intensity) 362/364 (($M-Cl)^+$, 100/36); Anal. calcd. for $C_{16}H_{24}Cl_2MnN_4$. 1.5 $H_2O$: C, 45.19; H, 6.04; N, 13.17; Cl, 16.71. Found: C, 45.39; H, 6.14; N, 12.97; Cl, 17.58.

EXAMPLE 25

Synthesis of [Manganese(II)(1,4,8,11-Tetramethyl-1, 4,8,11-tetraazacyclotetradecane)] Chloride A solution of 1,4,8,11-tetramethyl-1,4,8,11-tetraazacyclotetradecane (1.00 g, 3.90 mmole) and anhydrous manganese(II) chloride (0.49 g, 3.9 mmole) in anhydrous MeOH (50 ml) was refluxed for 4 h under a dry nitrogen atmosphere. After cooling, the mixture was concentrated in vacuo and ether was added to induce crystallization. The crystals were collected by filtration, washed with ether, and dried to give 1.07 g (72% yield) of a white crystalline solid: FAB mass spectrum (NBA) m/z (relative intensity) 346/348 [$(M-Cl)^+$, 100/31]; Exact mass $(M-Cl)^+$: calcd., 346.1696; Found: 346.1700 ($C_{14}H_{32}ClMnN_4$).

EXAMPLE 26

Synthesis of [Manganese(II)(C2,13-Dimethyl-3,6,9, 12,18-pentaazabicyclo[12.3.1]octadeca-1(18)2,12, 14,16-pentaene)] Chloride This manganese(II) complex was prepared as described by Alexander, M. D., Van Heuvelen, A., and Hamilton, Jr., H. G., (1970) *Inorg. Nucl. Chem. Lett.* 6, 445–448: FAB mass spectrum (NBA) m/z (relative intensity) 363/365 (($M-Cl)^+$, 100/28); Anal. calcd. for $C_{15}H_{23}Cl_2N_5Mn.2H_2O$: C, 41.35; H, 6.20; Cl, 16.29; N, 16.09. Found: C, 40.95; H, 5.78; Cl, 16.00; N, 15.64.

EXAMPLE 27

Synthesis of [Manganese(II)chloro(1,4,7,10,13-Pentaazacyclopentadecane)] Hexafluorophosphate A solution of silver hexafluorophosphate (285 mg, 1.47 mmol) in MeOH (20 ml) was added to a warm solution of [Manganese(II) dichloro(1,4,7,10,13-pentaazacyclopentadecane)] pentaazacyclopentadecane prepared as in Example 1F (500 mg, 1.47 mmol). The white precipitate of silver chloride formed instantly and was filtered off by passing the mixture through a bed of celite. The solution was concentrated in vacuo to a volume of 8 ml to induce crystallization. A white crystalline solid weighing 0.43 g (69% yield) was collected: FAB mass spectrum (NBA) m/z (relative intensity) 305/307 [$(M-PF_6)^+$, 100/36]; Anal. calcd for $C_{10}H_{25}N_5MnClPF_6$ $CH_3OH$: C, 31.05; H, 6.35; N, 16.49. Found: C, 30.76; H, 6.40; N, 17.78.

EXAMPLE 28

A. Synthesis of Ethyl N-(diphenylmethylene)-2-aminoeicosanoate

To a stirred solution of N-(diphenylmethylene)-glycine ethyl ester (67.3 g, 0.250 mol) in a 1:1 mixture of anhydrous THF (500 ml) and DMPU (500 ml) at −78° C. under a dry argon atmosphere was added a solution of lithium bis(trimethylsilyl)amide (250 ml−1.0M in THF, 0.25 mol) over a 10 min period. The resulting orange solution was stirred for 1.5 h at −78° C. While maintaining the temperature at −78° C., a solution of 1-bromooctadecane (83.4 g, 0.250 mol) in a 1:1 mixture of anhydrous THF (250 ml) and DMPU (250 ml) was added over a 10 min period and the resulting mixture was allowed to warm to room temperature. After stirring the mixture for 17 h, $H_2O$ (50 ml) and then ethyl acetate (2 l) were added. The solution was washed with $H_2O$ (4×2 l). The solution was dried over $Na_2CO_3$—$Na_2SO_4$ and the volume was reduced in vacuo to 1 l. The product was crystallized by the addition of hexane to give 104 g (80% yield) of an off-white crystalline solid: mp 62°–5° C.; $^1$H NMR (CDCl$_3$) δ 0.88 (t, J=6.6 Hz, 3H), 1.27 (m, 35H), 1.90 (m, 2H), 4.03 (m, 1H), 4.17 (m, 2H), 7.17 (m, 2H), 7.36 (m, 6H), 7.64 (m, 2H).

B. Synthesis of Ethyl 2-aminoeicosanoate Hydrochloride

To a stirred solution of ethyl-N-(diphenylmethylene)-2-aminoeicosanoate prepared as in Example 28A (104 g, 0.200 mol) in a 1:1 mixture (300 ml) of absolute ethanol and THF was added 0.5N hydrochloric acid (1.0 l) at room temperature over 10 min. The resulting solution was stirred for 30 min. Ethanol and THF were removed in vacuo and the aqueous slurry was extracted with $CH_2Cl_2$ (4×1 l). The extracts were combined and dried (MgSO$_4$). The solvent was removed in vacuo and the crude product was recrystallized from hexane to give 74.3 g (95% yield) of colorless needles: mp 91°–4° C.; $^1$H NMR (CDCl$_3$) δ 0.88 (t, J=6.6 Hz, 3H), 1.26 (m, 33H), 1.43 (m, 1H), 1.56 (m, 1H), 2.03 (quart, J=7.4 Hz, 2H), 4.03 (m, 1H), 4.27 (m, 2H), 8.84 (br s, 3H).

C. Synthesis of 2-Aminoeicosanamide

A slurry of ethyl-2-aminoeicosanoate hydrochloride prepared as in Example 28B (74.2 g, 0.189 mol) in anhydrous methanol (500 ml) was saturated with anhydrous ammonia at 0° C. The resulting mixture was sealed in a pressure bottle and heated to 60° C., resulting in a pressure of 40 psi. After 65 h at 60° C., the crystalline mixture was cooled to −20° C. and the solid was filtered to give 57.6 g (93%) of the product as off-white plates: mp 103°–4° C.; $^1$H NMR (CDCl$_3$) δ 0.88 (t, J=6.5 Hz, 3H), 1.37 (m, 35H), 1.82 (m, 1H), 3.67 (m, 1H), 5.30 (br s, 1H), 7.09 (br s, 1H).

D. Synthesis of 1,2-Diaminoeicosane

To a slurry of 2-aminoeicosanamide prepared as in Example 28C (57.5 g, 0.176 mol) in anhydrous THF (1.0 l) under a dry argon atmosphere was added a solution of lithium aluminum hydride (880 ml −1.0M in THF, 0.880 mol) over a 30 min period. The mixture was refluxed for 17.5 h and then quenched by the dropwise addition of $H_2O$ (100 ml) while cooling in an ice bath. The solid was filtered, washed with hot THF (2×1 l) and then hot methanol (1 l). The solids were then refluxed with THF (1 l) for 15 min and filtered again. The filtrates and washings were combined and the solvent was removed in vacuo. The crude product was dissolved in THF and solid impurities were removed by filtration. The solvent was again removed in vacuo and the procedure was continued using $CH_2Cl_2$. The crude product was recrystallized from $CH_2Cl_2$-hexane to give 37.9 g (69% yield) of the product as: mp 98°–101° C.; $^1$H NMR (CDCl$_3$) δ 0.91 (t, J=6.5 Hz, 3H), 1.33 (m, 34H), 1.96 (br s, 4H), 2.52 (m, 1H), 2.78 (m, 2H).

E. Synthesis of Dimethyl 3,6,9-Tris(p-toluenesulfonyl)-3,6,9-triazaundecanedioate 1,4,7-Tris(p-toluenesulfonyl)-1,4,7-triazaheptane-1,7-disodium salt prepared as in Example 1B (30 g, 49.2 mmol) was dissolved in dry N,N-dimethylformamide (180 ml) under argon. After cooling to 0° C. in an ice bath, methyl chloroacetate (15.40 g, 141.9 mmol) was added dropwise over a 10 min period. The reaction mixture became cloudy at the end of the addition, and was allowed to stir overnight while the ice bath warmed to room temperature. The solvent was evaporated under reduced pressure to give a brown oil which was dissolved in ethyl acetate (450 ml) giving a milky solution. This solution was washed twice with water (500 ml, then 300 ml). The combined water layers were back extracted with ethyl acetate (300 ml). The combined ethyl acetate layers were washed twice with saturated sodium chloride solution (200 ml), filtered, and evaporated to dryness. This residue was dissolved in dichloromethane (200 ml) and evaporated to dryness, and placed on the vacuum line. After recrystallization from chloroform-methanol, and washing with methanol and ether, an off-white solid was obtained weighing 27.46 g. An additional quantity of a slightly darker solid (4.7 g) was recovered from the filtrate after removing the solvent and recrystallizing as before. Total yield was 32.2 g (93% yield): mp 141°–2° C.; $^1$H NMR (CDCl$_3$) δ 2.42 and 2.44 (2 s, 9H), 3.41 (br s, 8H), 3.60 (s, 6H), 4.07 (s, 4H), 7.26–7.35 (m, 6H), 7.63–7.74 (m, 6H).

F. Synthesis of 3,6,9-Tris(p-toluenesulfonyl)-3,6,9-triazaundecanedioic Acid Dimethyl 3,6,9-tris(p-toluenesulfonyl)-3,6,9-triazaundecanedioate prepared as in Example 28E (16 g, 22.5 mmol) was slurried in tetrahydrofuran (100 ml). Sodium hydroxide (2N, 160 ml) was added dropwise over a 1 h period. After 72 h, the solvent was evaporated under reduced pressure, and hydrochloric acid (1N) was added to lower the pH to 4. This aqueous phase was extracted several times with ethyl acetate. The combined ethyl acetate layers were washed twice with brine, dried (MgSO$_4$), filtered, and evaporated to give a white solid, 14.22 g (93% yield): mp 177°–80° C.; $^1$H NMR (DMSO-d$_6$) δ 2.38 and 2.40 (2 s, 9H), 3.10 (m, 4H), 3.29 (m, 4H), 3.73 (s, 4H), 7.37 and 7.41 (2 d, J=7.9, 8.2 Hz, 6H), 7.61 and 7.66 (2 d, J=8.2 , 8.0 Hz, 6H).

G. Synthesis of 3,6,9-Tris(p-toluenesulfonyl)-3,6,9-triazaundecanedioyl Dichloride 3,6,9-Tris(p-toluenesulfonyl)-3,6,9-triazaundecanedioic acid prepared as in Example 28F (40.5 g, 59.4 mmol) was placed in a round bottom flask under argon, and oxalyl chloride (400 g, 3.15 moles) was added. This mixture, initially cloudy, became clear after a few hours, and was stirred overnight at room temperature. At the end of this time it was heated to 40° C. for 30 min. Oxalyl chloride was removed on the rotary evaporator. Dichloromethane (50 to 60 ml) was added to dissolve the resulting solid, and was removed on the rotary evaporator. This process was repeated twice, giving 40.5 g (99% yield) of a white solid: mp 136°–7° C.; $^1$H NMR (CDCl$_3$) δ 2.43 and 2.46 (2 s, 9H), 3.30–3.38 (m, 4H), 3.40–3.48 (m, 4H), 4.56 (s, 4H), 7.30–7.40 (m, 6H), 7.71 (d, J=8.2 Hz, 6H).

H. Synthesis of 5-Octadecyl-1,10,13-tris (p-toluenesulfonyl)-1,4,7,10,13-pentaazacyclopentadecane-3,8-dione To anhydrous CH$_2$Cl$_2$ (1.0 l) containing TEA (4.05 g, 40.0 mmol) under a dry argon atmosphere was added simultaneously at 0° C. a solution of 1,2-diaminoeicosane prepared as in Example 28D (6.25 g, 20.0 mmol) in anhydrous CH$_2$Cl$_2$ (400 ml) and a solution of 3,6,9-tris (p-toluenesulfonyl) -3,6,9-triazaundeca-1,11-dioyl-1,11-dichloride prepared as in Example 28G (14.4 g, 20.0 mmol) in anhydrous CH$_2$Cl$_2$ (400 ml) over a 4 h period. The resulting solution was then allowed to warm to room temperature. After stirring for 18 h, the solvent was removed in vacuo and the crude product was purified by flash chromatography (silica gel, CHCl$_3$-MeOH 98:2 to 95:5 (v/v) gradient) and then C-18 reverse phase resin (CH$_3$CN—CH$_2$Cl$_2$—MeOH 70:20:10 (v/v/v)) to give 7.37 g (38% yield) of the product as an amorphous white solid: $^1$H NMR (CDCl$_3$) δ 0.88 (t, J=6.6 Hz, 3H), 1.27 (m, 32H), 1.47 (m, 2H), 2.45 (s, 9H), 3.21 (m, 4H), 3.45 (m, 8H), 3.88 (m, 2H), 4.12 (m, 1H), 6.39 (d, J=8.9 Hz, 1H), 6.74 (t, J=3.3 Hz, 1H), 7.31 (m, 6H), 7.71 (m, 6H).

I. Synthesis of 2-Octadecyl-1,4,7,10,13,-pentaazacyclopentadecane

To a slurry of 5-octadecyl-1,10,13-tris(p-toluenesulfonyl) -1,4,7,10,13-pentaazacyclopentadecane-3,8-dione prepared as in Example 28H (4.00 g, 4.18 mmol) in anhydrous THF (100 ml) under a dry argon atmosphere was added a solution of lithium aluminum hydride in anhydrous THF (105 ml–1.0M, 105 mmol). The resulting solution was refluxed for 40 h. The mixture was quenched by the dropwise addition at 0° C. of H$_2$O (3.25 ml), then 15% NaOH (3.25 ml) and finally H$_2$O (9.60 ml). The resulting slurry was stirred for 1 h, THF (200 ml) was added and the white solid was filtered. The solid was washed with THF (200 ml) and then hot THF (300 ml). The filtrate and washings were combined and the solvent was removed in vacuo. The crude product was purified by recrystallization from THF—ethyl ether and then hexanes to give 1.21 g (62% yield) of the product as a white crystalline solid: mp 99°–100° C.; $^1$H NMR (CDCl$_3$) δ 0.88 (t, J=6.7 Hz, 3H), 1.25 (m, 33H), 1.52 (m, 1H), 1.66 (br s, 5H), 2.34 (m, 1H), 2.72 (m, 18H); Exact mass (M+H)$^+$: calcd., 468.5005; found, 468.5034 (C$_{28}$H$_{62}$N$_5$).

J. Synthesis of [Manganese(II)dichloro(2-Octadecyl-1,4,7,10,13-pentaazacyclopentadecane)]

To a refluxing solution of anhydrous manganese(II) chloride (0.18 g, 1.4 mmol) in anhydrous methanol (50 ml) was added 2-octadecyl-1,4,7,10,13-pentaazacyclopentadecane prepared as in example 28I (0.65 g, 1.4 mmol). The resulting solution was refluxed under a dry nitrogen atmosphere for 2 h and then stirred at room temperature overnight. The solvent was removed in vacuo, the oily residue redissolved in hot THF (20 ml) and filtered. The solution was concentrated and hot ethyl ether was added with stirring to give 0.62 g (75% yield) of the product as a white solid: FAB mass spectrum (NBA) m/z (relative intensity) 556/558 [(M–Cl)$^+$, 100/34]; Exact mass (M–Cl)$^+$: calcd., 557.3996; found, 557.4058 (C$_{28}$H$_{61}$N$_5$MnCl).

EXAMPLE 29

A- Synthesis of Boc-DL-Ppg

To suspension of DL-Ppg (20.0 g, 177 mmol) in THF (300 ml) and water (180 ml) was added 1N sodium hydroxide (180 ml). The resulting solution was cooled to 0 ° C. and (Boc)$_2$O (51.3 g, 235 mmol) was added at once. The pH was maintained at ~10 over a period of 5 h (with 1.0N sodium hydroxide) and the reaction was stirred for 12 h thereafter at room temperature. The solution was washed with ethyl acetate (100 ml) and acidified to pH ~2 with 1N potassium bisulfate. The aqueous phase was extracted with ethyl acetate (2×100 ml) and the combined extracts were dried (magnesium sulfate). The drying agent was filtered and the solution was concentrated to afford 35.4 g (94% yield) of the pure product as a white solid: $^1$H NMR (CDCl$_3$) δ 1.40 (s, 9H), 2.46–2.64 (m, 2H), 2.85 (t, J=2.5 Hz, 1H), 4.05 (dt, J=8.4, 5.5 Hz, 1H), 7.06 (d, J=8.1 Hz, 1H).

B. Synthesis of Boc-DL-Ppg-Gly-Gly-OEt.

To a solution of Boc-DL-Ppg prepared as in Example 29A (20.0 g, 93.8 mmol) in anhydrous DMF (350 ml) was added HOBT●H$_2$O (15.3 g, 113 mmol), EDC●HCl (21.7 g, 113 mmol), Gly-Gly-OEt (18.4 g, 98.3 mmol) and enough TEA (~35 ml) to adjust the pH to ~8 (measured by spotting the reaction mixture on moistened Hydrion paper). The resulting mixture was allowed to stir at room temperature for 18 h and was then concentrated in vacuo. The residue was dissolved in ethyl acetate (350 ml) and washed with 1N sodium bisulfate (2×75 ml), saturated sodium bicarbonate (2×75 ml) and brine (75 ml). The ethyl acetate solution was dried (magnesium sulfate), filtered and concentrated to afford 28.9 g (87% yield) of pure product as a white powder: $^1$H NMR (CD$_3$OD) δ 1.26(t, J=7.2 Hz,3H), 1.45 (s, 9H) , 2.38 (t, J =2.4 Hz, 1H), 2.64 (dddd, J=22.2, 16.8, 5.6, 2.4, 2H), 3.92 (ABq, Δv=32.0 Hz, J=22.2 Hz, 2H), 3.95 (s, 2 H), 4.17 (q, J=7.2 Hz, 2H), 4.19 (t, J=7.6 Hz,1H).

C. Synthesis of DL-Ppg-Gly-Gly-OEt●TFA

To a solution of Boc-DL-Ppg-Gly-Gly-OEt prepared as in Example 29B (28.0 g, 78.8 mmol) in methylene chloride (370 ml) was added TFA (101 ml) and the reaction mixture was stirred for 35 min at room temperature and concentrated. The residue was treated with ether (300 ml), stirred for 18 h, filtered and dried at high vacuum to afford 28.9 g (99% yield ) of the product as a grey-white solid: $^1$H NMR (DMSO-d$_6$) δ 2.76 (d, J=4.0 Hz, 2H), 3.07 (bs, 1H), 3.82 (m, 4H), 3.92 (t, J=6 Hz, 1H), 4.06 (q, J=7.2 Hz, 2H), 7.06 (bs, 1H), 8.35 (s, 3H), 8.80 (t, J=4.0 Hz, 1H).

D. Synthesis of Boc-Gly-Gly-DL-Ppg-Gly-Gly-OEt

To a solution of Boc-Gly-Gly (18.2 g, 78.4 mmol) in anhydrous DMF (350 ml) was added HOBT●H$_2$O (12.7 g, 94.0 mmol) and EDC●HCl (18.0 g, 94.0 mmol) and the resulting mixture was stirred at RT for 20 min. DL-Ppg-Gly-Gly-OEt trifluoroacetate prepared as in Example 29C (28.9 g, 78.2 mmol) was added and the pH of the solution was adjusted to ~8 by the addition of TEA (~20 ml, measured by spotting the reaction mixture on moistened Hydrion paper). The resulting mixture was allowed to stir at room temperature for 18 h thereafter and was then concentrated in vacuo. The residue was dissolved in ethyl acetate (350 ml) and washed with 1N sodium bisulfate (100 ml), saturated sodium bicarbonate (100 ml) and brine (100 ml). The ethyl acetate solution was dried (magnesium sulfate), filtered and concentrated to afford 12.8 g (35% yield) of the pure product as a white powder: $^1$H NMR (DMSO-d$_6$) δ 1.20 (t, J=7.2 Hz, 3H), 1.39 (s, 9H), 2.57 (dddd, J=22.0, 17.2, 5.4, 2.9 Hz, 2H), 3.59 (d, J=5.8 Hz, 2H), 3.72–3.82 (m, 4H), 4.10 (q, J=7.2 Hz, 2H), 4.47 (q, J=7.7 Hz, 1 H), 7.00 (t, J =5.3 Hz, 1 H), 7.98 (t, J=4.7 Hz, 1H), 8.15 (t, J=5.8 Hz, 1H) , 8.26 (d, J=7.8 Hz, 1H), 8.34 (t, J=5.2 Hz, 1H).

E. Synthesis of Boc-Gly-Gly-DL-Ppg-Gly-Gly

To a solution of Boc-Gly-Gly-DL-Ppg-Gly-Gly-OEt prepared as in Example 29D (12.8 g, 27.3 mmol) in methanol (50 ml) was added 2.5N sodium hydroxide (54.5 ml, 136.3 mmol). The resulting solution was stirred at room temperature for 30 min and the pH was then adjusted to ~3.8 with 1N sodium bisulfate. This mixture was extracted with ethyl acetate (5×50 ml) and the combined extracts were dried (magnesium sulfate), filtered and concentrated to afford 4.72 g (39% yield) of the pure product as a white foam: $^1$HNMR (DMSO-d$_6$) δ 1.35 (s, 9H), 2.52 (dddd, J=22.0, 16.9, 5.1, 2.4 Hz, 2H), 2.80 (t, J=2.4 Hz, 1H), 3.54 (d, J=4.0 Hz, 2 H), 3.65–3.81 (m, 6H), 4.42 (q, J=8.0 Hz, 1H), 6.95 (t, J=4.0 Hz, 1H), 7.93 (t, J=4.0 Hz, 1H), 8.00 (t, J=8.0 Hz, 1H), 8.19 (d, J=8.0 Hz, 1H), 8.27 (t, J=4.0, 1H).

F. Synthesis of cyclo-(Gly-Gly-DL-Ppg-Gly-Gly-)

This compound was synthesized by the method of Veber, D. F. et al., J. Org. Chem., 44, 3101–3105 (1979). To a solution of Boc-Gly-Gly-DL-Ppg-Gly-Gly prepared as in Example 29E (5.20 g, 11.8 mmol) in methylene chloride (40 ml) was added TFA (10 ml) and the mixture was stirred at room temperature for 40 min. The mixture was concentrated in vacuo and the residue was triturated with ether (3×75 ml). The resulting white powder was collected by filtration and dried at high vacuum to afford 4.87 g (91% yield) of Gly-Gly-DL-Ppg-Gly-Gly●TFA. This material was dissolved in anhydrous DMF (1400 ml) and the solution was cooled to —50 ° C. To this mixture was added DPPA (2.90 ml, 13.4 mmol) followed by enough TEA to adjust the pH to ~8 (measured by spotting the reaction mixture on moistened Hydrion paper). The reaction mixture was allowed to stir at −45° to −35° C. for 6 h and then allowed to stand at −25 ° C. for 48 h. During this time the pH was monitored periodically (as described above) and maintained at ~8 by the addition of TEA. After this time the reaction mixture was allowed to stand at 0° C. for 48 h. Again the pH was monitored periodically and maintained at ~8 by the addition of TEA. After this time the reaction mixture was diluted with water (1400 ml) and stirred with Bio-Rad AG 501-X8 (mixed-bed) resin (500 g) for 6 h. The resin was filtered, the solution was concentrated to a final volume of ~50 ml (only DMF remained), and the cyclic peptide was precipitated by the addition of ether (300 ml). The cyclic peptide was collected by filtration and triturated with refluxing THF (75 ml) for 20 h. The white solid was collected by filtration of the hot THF and dried at high vacuum to afford 1.03 g (30% yield) of product: mp 254°–7° C. (dec); $^1$H NMR (DMSO-d$_6$) δ 2.52 (ABq of dd, Δv=59.2 Hz, J=16.7, 7.1, 2.6 Hz, 2H), 2.83 (t, J=2.6 Hz, 1H), 3.48 (dd, J=15.6, 4.0 Hz, 1H), 3.57–3.81 (m, 6H), 3.88 (dd, J=15.2, 6.0 Hz, 1H), 4.04 (dd, J=15.6, 7.7 Hz, 1H), 4.38 (apparent q, J=7.4 Hz, 1H), 7.83 (t, J=5.4 Hz, 1H), 8.05 (t, J=5.5 Hz, 1H), 8.10–8.20 (m, 3H); FAB mass spectrum (NBA) m/z 324.2 (M+H)$^+$.

G. Synthesis of 2-Propargyl-1,4,7,10,13-pentaazacyclopentadecane

An oven-dried flask containing a glass stir-bar was allowed to cool to room temperature under argon flow and was charged with cyclo-(Gly-Gly-Ppg-Gly-Gly-) prepared as in Example 29F (1.03 g, 3.19 mmol) and anhydrous THF (50 ml). To this stirred suspension was added a 1.0M solution of lithium aluminum hydride in THF (38.2 ml, 38.2 mmol) dropwise. The resulting mixture was heated to reflux for 18 h, cooled to 0° C. and quenched (cautiously) by the dropwise addition of saturated sodium sulfate solution (~10 ml). The resulting mixture was concentrated in vacuo to a dry white powder and this powder was triturated with methylene chloride (3×100 ml). The combined methylene chloride solutions were concentrated in vacuo to afford 480 mg of a viscous oil. This material was recrystallized twice from hexanes and once from acetonitrile to afford 212 mg (27% yield) of pure product as a white solid: mp 70°–2° C.; $^1$HNMR (CDCl$_3$) δ 1.85 (br s, 5H), 1.98 (t, J=2.6 Hz, 1H), 2.27 (ddd, J=16.8, 7.0, 2.6 Hz, 1H), 2.37 (ddd, J=16.3, 4.4, 2.7 Hz, 1H), 2.51 (dd, J=10.6, 9.9 Hz, 1H), 2.55–2.95 (m, 18H) ; Exact mass (M+Li)$^+$: calcd., 260.2427; found, 260.2468 (C$_{13}$H$_{27}$N$_5$Li); Anal. calcd. for C$_{13}$H$_{27}$N$_5$: C, 61.62; H, 10.74; N, 27.64. Found: C, 62.86, H, 10.89, N 27.83.

H. Synthesis of [Manganese(II)dichloro(2-Propargyl-1,4,7,10,13-pentaazacyclopentadecane)]

A solution of 2-propargyl-1,4,7,10,13-pentaazacyclopentadecane prepared as in Example 29G (310 mg, 1.22 mmol) and anhydrous manganese(II) chloride (154 mg, 1.22 mol) in methanol (50 ml) were refluxed under a dry nitrogen atmosphere for 2 h and then stirred overnight at room temperature. The solution was taken to dryness, redissolved in absolute ethanol (15 ml) and filtered through celite. Concentration and recrystallization from ethanol-ether afforded 370 mg (80% yield) of white microcrystalline product: FAB mass spectrum (NBA) m/z (relative intensity) 378 (M$^+$, 2), 343/345 ((M–Cl)$^+$, 100/30); Anal. calcd. for C$_{13}$H$_{27}$Cl$_2$MnN$_5$: C, 41.14; H, 7.18; N, 18.47. Found: C, 40.49; H, 6.56; N, 18.14.

EXAMPLE 30

A. Synthesis of 1-Amino-1-cyclohexylacetonitrile Hydrochloride

This compound was prepared following the general procedure of Paventi, M. and Edward, J. T., Can. J. Chem., 65, 282–9 (1987). Cyclohexane carboxaldehyde (11.25 g, 100.3 mmol) was added to a stirred mixture of tetrahydrofuran (30 ml) and ammonium hydroxide (7 ml, 110 mmol). Ten min later ammonium chloride (5.41 g, 101.1 mmol) and potassium cyanide (6.51 g, 100.0 mmol) were added. This mixture was stirred for about 2 h in a flask lightly sealed with a rubber septum. At this time sodium sulfate (30 g, 211 mmol) and ether (80 ml) were added. Stirring became difficult; the flask was occasionally swirled. After about an hour, the mixture was filtered. The solids were washed with ether. The filtrate and ether washings were combined and the ether was removed under reduced pressure to give a viscous liquid. Ether (about 300 ml) was added to this liquid and the resulting solution was treated with gaseous hydrochloric acid, precipitating a large quantity of white solid. This solid was filtered, washed with ether, and dried. Warm acetonitrile (300 ml) was added, and the resulting mixture was filtered. The acetonitrile was removed under reduced pressure and the white solid was recrystallized from hot ethanol (120 ml)-ethyl acetate (200 ml), giving 6.3 g (36% yield) of a white solid: mp 195° C.; $^1$H NMR (DMSO-$_6$) δ 0.96 to 1.30 (several m, 5H), 1.58–2.01 (several m, 6H), 4.50 (d, J=5.6 Hz, 1H), 9.36 (br s, 3H).

B. Synthesis of 1-Cyclohexyl-1,2-ethanediammonium Dichloride

1-Amino-1-cyclohexylacetonitrile hydrochloride prepared as in Example 30A (5.6 g, 32.1 mmol) was dissolved in ethanol (60 ml) and cooled to 0° C. in a Fisher-Porter bottle. A cold solution of concentrated hydrochloric acid (3.3 ml, 39.9 mmol, 37%) in ethanol (60 ml) was added to the other ethanol solution in small portions. Platinum oxide hydrate (330 mg, 1.35 mmol) was added, and the mixture was hydrogenated at 60 psi at room temperature for 6 h. At the end of this time, the hydrogen was released, the solution was filtered, and the solvent was removed under reduced pressure. Recrystallization from hot ethanol-dichloromethane gave 4.37 g (63% yield) of the product as a white crystalline solid: mp 262°–3° C.; $^1$H NMR (DMSO-$d_6$) δ 0.96–1.30 (several m, 5H), 1.56–1.80 (several m, 6H), 3.00–3.20 (m, 2H), 3.28 (br m, 1H), 8.60 (br s, 6H).

C. Synthesis of 1-Cyclohexyl-1,2-diaminoethane

1-Cyclohexyl-1,2-ethanediammonium dichloride prepared as in Example 30B (6.68 g, 31.05 mmol) was dissolved in methanol (330 ml) and stirred with powdered sodium hydroxide (2.7 g, 67.5 mmol) at room temperature for 1 h. At the end of this time it was filtered (twice) and the filtrate was evaporated under reduced pressure to give 3.01 g (68% yield) of a pale yellow liquid: $^1$H NMR (CDCl$_3$) δ 0.94–1.33 (several. m, 10H), 1.61–1.83 (2 m, 5H), 2.39–2.53 (m, 2H), 2.79 (dd, J=11.8, 2.9 Hz, 1H).

D. Synthesis of 5-Cyclohexyl-1,10,13-Tris(p-toluenesulfonyl)-1,4,7,10,13-pentaazacyclopentadecan-3,8-dione In a two liter, four necked round bottom flask equipped with an argon inlet, two dropping funnels, and magnetic stir bar, dichloromethane (600 ml) was added and cooled to 0° C. 3,6,9-Tris(p-toluenesulfonyl)-3,6,9-triazaundecandioyl dichloride prepared as in Example 28G (15.15 g, 21.08 mmol) was dissolved in dichloromethane (350 ml) and added to one of the dropping funnels. 1-Cyclohexyl-1,2-diaminoethane prepared as in Example C (3.0 g, 21.09 mmol) and triethylamine (4.69 g, 46.3 mmol) were dissolved in dichloromethane (350 ml) and added to the other dropping funnel. These two solutions were simultaneously added dropwise to the stirred dichloromethane solution at 0° C. in the reaction flask over a 5 h period. The reaction mixture was then allowed to stir overnight at room temperature. The solvent was removed under reduced pressure giving a yellow solid. This solid was redissolved in dichloromethane (150 ml) and washed twice with water (120 ml). After drying (Na$_2$CO$_3$) the solvent was stripped off and the product was recrystallized from dichloromethane-methanol by cooling to –22° C., giving 4.66 g (28% yield) of the product as a white solid: mp 224° C.; $^1$H NMR (CDCl$_3$) δ 0.96 to 1.30 (several m, 5H), 1.48 (m, 1H), 1.60 to 1.81 (several m, 5H), 2.46 (s, 9H), 3.09 to 3.78 (several m, 12H), 3.89 and 3.91 (2 d, J=16.7 and 16.6 Hz, 2H), 4.03 (m, 1H), 6.61 (d, J=9.5 Hz, 1H), 6.85 (dd, J=7.1 Hz, 4.1 Hz, 1H), 7.31 to 7.42 (several m, 6H) , 7.70 (d, J=7.7 Hz, 4H), 7.76 (d, J=8.3 Hz, 2H) .

E. Synthesis of 2-Cyclohexyl-1,4,7,10,13-pentaazacyclopentadecane

5-Cyclohexyl-1,10,13-tris(p-toluenesulfonyl)-1,4,7,10,13-pentaazacyclopentadecan-3,8-dione prepared as in Example 30D (4.841 g, 6.386 mmol) was placed in a 2-necked flask under argon. Dry 1,2-dimethoxyethane (dme, 100 ml) was added, giving a suspension. After placing the reaction flask in a cold water bath, lithium aluminum hydride in dme (0.5M, 100 ml, 50 mmol) was added over a 10 min period giving an almost clear solution. Additional dme (50 ml) was added and the flask was removed from the water bath and heating with a mantle was started. After a few minutes of heating, more lithium aluminum hydride solution (40 ml, 20 mmol) was added, and heating to reflux was continued. The solution quickly became yellow and opaque. Overnight the refluxed solution became mostly white and heterogeneous. After 39.5 h, the reaction mixture appeared milky with a slight tint of yellow. Heating was stopped and the reaction mixture was cooled to room temperature. It was quenched, after placing the reaction flask in a water bath, by careful addition of water (2.2 ml) over a 10 min period. The reaction was exothermic with gas evolution. Next, 15% aqueous sodium hydroxide solution (2.2 ml) was rapidly added, then water (6.5 ml). After stirring for 1 h, tetrahydrofuran (135 ml) was added with continued stirring. The mixture was thick with a white precipitate. Fifty min later the mixture was filtered under an inverted funnel through which N$_2$ was flowing, and the filtrate was removed on the rotary evaporator to give a viscous liquid. After pumping on the vacuum line, this residue was recrystallized under argon from acetonitrile with cooling to –20° C. Three successive batches of a slightly sticky white solid were obtained which were combined and recrystallized from hexanes under argon with cooling to –20° C. to give 0.796 g (42% yield): mp 67°–69.5° C. (under nitrogen); $^1$H NMR (CDCl$_3$) δ 0.84–1.32 (several m, 5H), 1.40–2.0 (several m, 11H), 2.28–2.46 (m, 2H), 2.50–2.97 (several m, 17H); Exact mass (M+H)$^+$: calcd, 298.2971; Found, 298.2973 (C$_{16}$H$_{36}$N$_5$).

F. Synthesis of [Manganese(II)dichloro(2-Cyclohexyl-1,4,7,10,13-pentaazacyclopentadecane)]

2-Cyclohexyl-1,4,7,10,13-pentaazacyclopentadecane prepared as in Example 30E (0.50 g, 1.7 mmol) was added to a refluxing anhydrous MeOH solution (50 ml) containing anhydrous manganese(II) chloride (0.21 g, 1.7 mmol) under a dry nitrogen atmosphere. After refluxing for 2 h, the solution was stirred overnight at room temperature. The solution was filtered through celite and then taken to dryness. The solid was recrystallized from EtOH to give 0.44 g (62% yield) of a white solid after washing with ethyl ether and drying in vacuo: FAB mass spectrum (NBA +Li) m/z (relative intensity) 429 (M$^+$+Li, 5), 387/389 [(M$^+$–Cl), 100/35]; Anal. calcd for C$_{16}$H$_{35}$N$_5$MnCl$_2$: C, 45.40; H, 8.33; N, 16.54; Cl, 16.75. Found: C, 45.39; H, 8.04; N, 16.33; Cl, 16.37.

EXAMPLE 31

A. Synthesis of 1-Phenyl-1,2-ethanediammonium Dichloride

This compound was synthesized following the procedure of Esser, T., Karu, A. E., Toia, R. F., Casida, J. E., Chem. Res. Toxicol., 4, 162–7 (1991). Absolute ethanol (300 ml) was cooled to 0° C., then 2-phenylglycinonitrile hydrochloride (technical grade, purity unknown, 20 g, 118 mmol if pure) was added. While maintaining the internal temperature below 5° C., a solution of ethanol (150 ml) and concentrated hydrochloric acid (4.6 ml, 55.7 mmol) was added in small portions. The solution was allowed to warm to room temperature, platinum oxide (2.0 g, 8.8 mmol) was added and the mixture was pressurized to 60 psi for 6 h. The pressure was released, the reaction mixture was filtered and the solvent was removed under reduced pressure. Recrystallization from ethanol-dichloromethane gave 6.0 g (yield not determined due to unknown purity of starting material) of the product as a white solid: mp 303°–4° C. $^1$H NMR (DMSO-$d_6$) δ 3.24 (dd, J=13.4, 6.0 Hz, 1H), 3.55 (dd, J=13.4, 7.0 Hz, 1H), 4.65 (t, J=6.5 Hz, 1H), 7.47 (m, 3H), 7.60 (m, 2H), 8.77 (br s, 6H).

B. Synthesis of 1-Phenyl-1,2-diaminoethane

Following the procedure of Esser, T., Karu, A. E., Toia, R. F., Casida, J. E., Chem. Res. Toxicol., 4, 162–167 (1991), 1-phenyl-1,2-ethanediammonium dichloride prepared as in Example 31A (19.46 g, 93.05 mmol) was dissolved in one liter of 2N aqueous potassium hydroxide, and stirred about 10 min. This solution was extracted three times with diethyl ether (1000 ml). After removing the ether under reduced pressure, a small amount of a pale yellow liquid was left. The aqueous layer was then extracted eight times with dichloromethane (250 ml each). These extracts were combined with the residue from the ether extracts, dried (MgSO$_4$), filtered, and stripped down to give 5.0 g (40% yield) of a pale yellow liquid. This material showed small amounts of impurity peaks in the NMR, but was used in the next step without additional purification: $^1$H NMR (CDCl$_3$) δ 1.38 (br s, 4H), 2.69 (m, 1H), 2.79 (m, 1H), 3.78 (m, 1H), 7.10 to 7.30 (2 m, 5H).

C. Synthesis of N, N'-Di(p-toluenesulfonyl)-1,2-diamino-1-phenylethane 1,2-Diamino-1-phenylethane prepared as in Example 31B (5.0 g, 37.5 mmol) was dissolved in water (110 ml), and sodium hydroxide (3.0 g, 75 mmol) was added in small portions. After stirring for 10 min, p-toluenesulfonyl chloride (14.31 g, 75.1 mmol) was added and stirring was continued for 1 h. Ether (225 ml) was added and the reaction mixture was stirred overnight at room temperature. A white solid precipitated out during this time. The solid was filtered, washed with ether, and dried (13 g). Recrystallization from dichloromethane-hexane gave 12.17 g (73% yield) of a white solid: mp 148°–9° C.; $^1$H NMR (CDCl$_3$) δ 2.39 (s, 3H), 2.43 (s, 3H), 3.19 (m, 2H), 4.31 (dd, J=12.2, 6.8 Hz, 1H), 4.77 (t, J=6.6, 1H), 5.32 (d, J=6.7, 1H), 6.98 (m, 2H), 7.19 (m, 5H), 7.27 (d, J=5.9, 2 H), 7.59 (d, J=8.3 Hz, 2H), 7.68 (d, J=8.3 Hz, 2H).

D. Synthesis of 2-Phenyl-1,4,7,10,13-pentakis(p-toluenesulfonyl)-1,4,7,10,13-pentaazacyclopentadecane In a 4-necked 3 liter flask equipped with an argon inlet, dropping funnel, internal thermometer, and magnetic stir bar, N,N'-di(p-toluenesulfonyl)-1-phenylethylenediamine prepared as in Example 31C (39.0 g, 87.726 mmol) was dissolved in dry N,N-dimethylformamide (dmf, 1,350 ml) under an argon atmosphere. 18-Crown-6 (46.417 g, 175.61 mmol) which had been stored over molecular sieves was added. Sodium hydride (95%, 4.49 g, 178 mmol) was weighed out in the dry box, and added directly to the reaction flask. Immediate, vigorous gas evolution took place. Stirring was continued at room temperature for 1 h, then, over the next 55 min a heating mantle was used to bring the internal temperature to 100° C. 3,6,9-tris(p-toluenesulfonyl)-3,6,9-triazaundecane-1,11-di-p-toluenesulfonate prepared as in Example 2C (84.59 g, 87.91 mmol) was dissolved in dry nitrogen saturated dmf (650 ml), and added dropwise to the stirred solution maintained at 100° C. over 4 h 10 min. After stirring the reaction overnight (16 h), it was cooled somewhat, filtered through Celite, and most of the solvent was removed under reduced pressure. The thick brown liquid was dissolved in chloroform (300 ml) and washed with three 300 ml portions of water. The combined aqueous washes were backwashed with 30 ml of chloroform and the combined organic phases were washed with three portions of saturated aqueous saline (150 ml each), water (150 ml), and saturated aqueous saline (150 ml). After drying (MgSO$_4$), and filtration, the solvent was partially stripped off, to a volume of 250 to 300 ml. Recrystallization from chloroform-methanol gave successive crops of product. A flash filtration on silica etuting with 98:2 dichloromethane: methanol was done to remove some impurities in the filtrate. Three successive liters were collected, all containing product which were combined, stripped down, and recrystallized from chloroform-methanol to give 19.07 g (21% yield) of product: mp 209°–210° C. (dec); $^1$H NMR (CDCl$_3$) δ 2.33 (s, 3H), 2.43 and 2.46 (2 s, 6H), 2.83 (m, 1H), 2.96 to 3.72 (several m, 16H), 3.98 (dd, J=15.4, 5.6 Hz, 1H), 5.22 (t, J=1.5 Hz, 1H), 7.15 (d, J=8.1 Hz, 2H), 7.26–7.42 (m, 15.5H, includes solvent), 7.46 (d, J=7.7 Hz, 2H), 7.57 (d, J=7.3 Hz, 2H), 7.66–7.79 (m, 6H).

E. Synthesis of 2-Phenyl-1,4,7,10,13-pentaazacyclopentadecane

Sodium naphthalenide was prepared by adding dry 1,2-dimethoxyethane (dme, 200 ml) to naphthalene (24.174 g, 188.60 mmol) under argon in a Schlenk tube, then adding freshly cut sodium pieces (4.40 g, 191.4 mmol) and stirring with a glass coated stir bar for 1.75 h. A dark green color rapidly developed. Meanwhile, a one liter four necked round bottom flask equipped with overhead stirrer, internal thermometer, dropping funnel and argon inlet was inerted. 2-Phenyl-1,4,7,10,13-pentakis(p-toluenesulfonyl)-1,4,7,10,13-pentaazacyclopentadecane prepared as in Example 31D (9.995 g, 9.41 mmol) was added, then t-butanol (3.60 g, 48.57 mmol), followed by dry dme (350 ml) and stirring was started. After transferring the sodium naphthalenide to the dropping funnel via cannula, the stirred solution was cooled to –75° C. (internal) and the sodium naphthalenide solution was added dropwise over a 90 min period. The dark green color discharged rapidly on contact with the stirred solution. When 2 equivalents of sodium naphthalenide per sulfonamide had been added, the green color persisted somewhat, but faded after a few minutes. After 15 min more at –75°, the reaction mixture was allowed to warm slowly to –40° C. While the temperature was below –60° C., additional sodium naphthalenide was added in small quantities to get a persisting green color. The total volume of sodium naphthalenide solution added was about 110 ml (104 mmol). On warming to 10° C. over the next hour, the solvent was removed on the rotary evaporator leaving a brown solid. After drying on the vacuum line, this solid was extracted with dry pentane (five 100 ml portions) under argon, and filtered using a filter transfer device (a cannula ending in a flared steel barrel onto which a filter paper is fastened with nichrome wire). The combined pentane extracts were stripped giving a brown solid. Some naphthalene sublimed out on the vacuum line. The residue was reextracted with pentane (three 50 ml portions), stripped down to a white and brown solid, and heated to 42° C. under vacuum to give, after sublimation of more naphthalene, a brown residue. Although some product was seen (NMR), there appeared to be a considerable quantity of partially tosylated material present. These residues were combined (3.06 g) and subjected to another reduction with sodium naphthalenide.

Sodium naphthalenide was prepared as above from naphthalene (3.01 g, 23.48 mmol) and sodium (0.549 g, 23.88 mmol) in dry dme (26 ml), over 2 hours 10 minutes. In a 500 ml four necked flask equipped as above, the partially tosylated macrocycle was dissolved in dme (65 ml) under argon and t-butanol (0.48g, 6.48 mmol). A dry ice-isopropanol bath was used to lower the internal temperature to −70° C., and addition of the sodium naphthalenide solution was started. Over a 2 h period, 19 ml of sodium naphthalenide were slowly added until a green color persisted at temperatures below −65° C. Over the next 40 min, the internal temperature was allowed to reach −50° C. where it was held for about 40 min (with one excursion to −40° C.) and remained dark green. Ethanol (1 ml) was added at −50° C. Warming continued, with decolorization taking place at −25° C. When the reaction mixture reached 10° C., the solvent was removed under reduced pressure, and the residue was placed on the vacuum line. After cryopumping (some naphthalene removed), and under vacuum overnight, the residue was extracted with dry pentane (three times with 50 ml). The pentane fraction was evaporated under reduced pressure and placed on the vacuum line. The undissolved residue was treated with water (15 ml). The aqueous solution was extracted with chloroform (three times with 35 ml). After drying ($Na_2CO_3$), and filtration, the chloroform solution was evaporated down to an amber liquid (2.26 g). This was extracted with pentane (four 100 ml portions) giving 580 mg of a white crystalline solid. $^1$H NMR suggested that the first of these was about 5:1 of desired product to ring opened product, while the second was about 2:1 of desired product to ring opened product. An additional pentane extract (50 ml) of the chloroform extract was combined with the pentane extract (50 ml) of the water/chloroform extract of the $NH_4Cl$/NaOH treated fraction from the previous experiment and stripped down. All of the pentane extracts showing more product macrocycle than ring opened product were dissolved in methylene chloride, combined, stripped down, and cryopumped. This residue was dissolved in dry hexane (110 ml) under argon at about 50° C. and filtered using a filter transfer device. On cooling to about 40° C. the solution became cloudy. Overnight, a small amount of a yellowish oil collected in the center of the flask. This material was filtered, and cryopumped. $^1$H NMR showed it to be mostly undesired ring opened product of the desired macrocycle. The filtrate was heated to 45° C., and cooled to 25° C., depositing a small amount of an oily solid which was filtered. The filtrate was again heated to 45° C., and slowly cooled to about 5° C., depositing small white crystals. The flask was wrapped and placed in a beaker in the freezer. White crystals were filtered cold using a filter transfer device and washed with cold (−20° C.) hexane, then dried under vacuum. Yield, 370 mg, as a mixture containing about 10 to 15% of a ring opened material: $^1$H NMR ($CDCl_3$) δ 1.35 (d, J=6.6 Hz, minor product), 1.85 (br s), 2.44–3.00 (several m, major+minor products), 3.69 (dd, J=10.5, 3.0 Hz, major product), 3.74 (q, J=6.7 Hz, minor product), 7.21–7.34 (several m, both products), 7.75 (d, J=8.3 Hz, minor product); FAB mass spectrum m/z 292.2 $(M+H)^+$.

F. Synthesis of [Manganese(II)dichloro(2-Phenyl-1, 4,7,10,13-pentaazacyclopentadecane)]

To a methanolic solution (50 ml) at low reflux containing anhydrous manganese(II) chloride (150 mg, 1.19 mmol) was added a methanolic solution of 2-phenyl-1,4,7,10,13-pentaazacyclopentadecane prepared as in Example 31E (0.35 g, 1.2 mmol). The reaction was refluxed for 3 h under a dry nitrogen atmosphere and was then allowed to stir at room temperature overnight. The yellow solution was then filtered through celite and taken to dryness. The solid glassy oil was washed with hot ethyl ether (30 ml) and then dissolved in hot EtOH. The EtOH solution was filtered and then evaporated. The solid was recrystallized from acetone/$CH_3CN$ to give 255 mg (52% yield) of a white microcrystalline solid: FAB mass spectrum (NBA) m/z (relative intensity); 416 ($M^+$, 2), 381/383 [$(M-Cl)^+$, 100/32] Anal. calcd. for $C_{16}H_{29}N_5MnCl_2$: C, 46.05; H, 7.01; N, 16.78. Found: C, 46.23; H, 7.04; N, 16.62.

EXAMPLE 32

A. Synthesis of Ethyl 1-Naphthylglyoxalate

The title compound was synthesized by the procedure described by Blicke, F. F. and Feldkamp, R. F., *J. Am. Chem. Soc.*, 66, 1087–91 (1944). Naphthalene (76 g, 0.59 mol) dissolved in dry 1,1,2,2-tetrachloroethane (500 mL) and ethyl oxalyl chloride (89.5 g, 0.65 mol) were placed in a three necked flask fitted with a mercury sealed stirrer, a solid addition funnel and a reflux condenser. The mixture was cooled to 0° C. and aluminum chloride (95 g, 0.71 mol) was added in portions over a period of 2 h. The reaction mixture was stirred at room temperature for 12 h and poured over ice. The organic layer that separated out was washed with water (500 ml), dilute $Na_2CO_3$ solution (250 ml) and water (500 ml). The 1,1,2,2-tetrachloroethane was removed in vacuo and the residue was distilled. The pale yellow oil (93 g, bp 164°–8° C. / 3mm) was a mixture of ethyl 1-naphthylglyoxalate and ethyl 2-naphthylglyoxalate. Picric acid (50 g) was added to the mixture of the two isomers (50 g) in absolute ethanol (86 ml). The mixture was heated until a clear solution was obtained. On cooling a crystalline precipitate formed which was filtered off and washed with cold EtOH to yield 90 g of ethyl 1-naphthylglyoxalate picrate. The picrate was suspended in water (1000 ml) and the oily residue was treated with 10% sodium carbonate solution until alkaline to litmus. The ethyl 1-naphthylglyoxalate which separated was extracted with $CCl_4$ (4×40 ml). The combined extracts were washed with water until free from picric acid, dried over $MgSO_4$ and evaporated to yield an oil. Fractional distillation of the oil gave 41 g (49% yield) of ethyl 1-naphthylglyoxalate as a pale yellow oil: bp 167° C. / 3 mm; $^1$H NMR ($CDCl_3$) δ 1.13 (t, J=7.1 Hz, 3H), 4.14 (q, J=7.1 Hz, 2H), 7.53–7.71 (m, 3 H), 7.91 (d, J=8.1 Hz, 1H), 7.98 (d, J=7.3 Hz, 1H), 8.11 (d, J=8.3 Hz, 1H), 9.04 (d, J=8.8 Hz, 1H).

B. Synthesis of 1-NaphthylGly-OEt

A solution of ethyl 1-naphthylglyoxalate prepared as in Example 32A (11.4 g, 50 mmol) in EtOH (300 ml) containing sodium acetate (NaOAc) (5.3 g, 65 mmol) and hydroxylamine hydrochloride (6.9 g, 100 mmol) was refluxed for 3 h. The reaction mixture was cooled and the solvent was evaporated in vacuo to yield the oxime. To an ice cooled (5° C.) solution of the oxime in MeOH/HCOOH/$H_2O$ (120 ml/75 ml/60 ml), Zn dust (7.6 g) was added portionwise over 40 min. Following complete addition the mixture was stirred at 0° C. for 12 h. After warming the mixture to 25° C. the mixture was filtered. The filtrate was concentrated in vacuo to yield an oil. The oil was dissolved in 1N HCl (100 ml) and the solution was washed with EtOAc (50 ml). The aqueous layer was made alkaline to pH 8 with 1N NaOH, extracted with EtOAc (3×50 ml), dried over $MgSO_4$ and concentrated in vacuo to give 4.65 g (40% yield) of 1-naphthylglycine ethyl ester as a pale yellow oil: $^1$H NMR ($CDCl_3$) δ 1.12 (t, J=7.0 Hz, 3H), 4.13 (q, J=7.0 Hz, 2H), 6.36 (s, 1H), 7.5–7.8 (m, 7H).

C. Synthesis of Boc-Gly-Gly-1-naphthylGly-OEt

Isobutyl chloroformate (2.63 ml, 20.3 mmol) was added to a solution of Boc-Gly-Gly-OH (4.7 g, 20.3 mmol) and N-methyl morpholine (2.2 ml, 20.3 mmol) in dry DMF (60 ml) at 0° C. and left to stir for 30 min. A solution of 1-naphthylGly-OEt prepared as in Example 32B (4.65 g, 20.3 mmol) in $CH_2Cl_2$ (60 ml) was added to the above mixture and was stirred for 15 min at 0° C. and at room temperature for 2 h. The mixture was diluted with EtOAc (200 ml) and washed sequentially with 1N $NaHSO_4$ (1×100 ml), water (1×100 ml), saturated $NaHCO_3$ (1×100 ml), and brine (1×100 ml). The organic layer was dried over $MgSO_4$ and concentrated in vacuo to yield 7.86 g (87% yield) of Boc-Gly-Gly-1-naphthylGly-OEt as a white solid: mp 76° C.; $^1H$ NMR ($CDCl_3$) δ 1.13 (t, J=7.2 Hz, 3H), 1.38 (s, 9H); 3.68 (m, 2H), 3.95 (m, 2H), 4.13 (q, J=7.2 Hz, 2H), 5.35 (br t, 1H), 6.26 (d, J=7.4 Hz, 1H), 6.98 (br t, 1H); 7.37–7.55 (m, 4H); 7.79–7.85 (m, 3H); 8.12 (d, J=8.1 Hz, 1H).

D. Synthesis of Boc-Gly-Gly-1-naphthylGly

Boc-Gly-Gly-1-naphthylGly-OEt prepared as in Example 32C (7.86 g, 17.6 mmol) was dissolved in MeOH (150 ml) and 1N NaOH (250 ml) solution was added to the stirred mixture at room temperature. The mixture was stirred for 12 h and the MeOH was removed in vacuo. The pH of the aqueous layer was adjusted to 4.5 with 1N HCl solution, extracted with EtOAc (2×100 ml), washed with brine, dried over $MgSO_4$ and concentrated in vacuo to yield 5.78 g (78% yield) of Boc-Gly-Gly-1-naphthylGly as a white solid: mp 115°–6° C.; $^1H$ NMR (DMSO-$d_6$) δ 1.35 (s, 9 H), 3.53 (d, J=5.9 Hz, 2H), 3.79 (d, J=5.5 Hz, 2 H), 6.11 (d, J=7.3 Hz, 1H), 6.96 (t, J=5.7 Hz, 1H), 7.48–7.98 (m, 8H), 8.06 (d, J=8.1 Hz, 1H), 8.75 (d, J=7.8 Hz, 1H).

E. Synthesis of Boc-Gly-Gly-1-naphthylGly-Gly-Gly-OEt

Isobutyl chloroformate (1.8 ml, 13.8 mmol) was added to a solution of Boc-Gly-Gly-1-naphthylGly prepared as in Example 32D (5.73 g, 13.8 mmol) and N-methyl morpholine (1.52 ml, 13.8 mmol) in $CH_2Cl_2$ (50 mL) at 0° C. and left to stir for 30 min. A solution of HCl.Gly-Gly-OEt (2.7 g, 13.8 mmol) and N-methyl morpholine (1.52 ml, 13.8 mmol) in DMF (50 ml) was added to the above mixture, stirred for 15 min at 0° C. and at room temperature for 2 h. The mixture was diluted with EtOAc (100 ml), washed with 1N $NaHSO_4$ (1×50 ml), water (1×50 ml), saturated $NaHCO_3$ (1×50 ml), and brine (1×50 ml). The organic layer was dried over $MgSO_4$ and concentrated in vacuo to yield the crude product. Boc-Gly-Gly-1-naphthylGly-Gly-Gly-OEt was recrystallized from hot $CH_2Cl_2$ and hexane to give 5.0 g (65% yield) of a white solid: mp 190° C.; $^1H$ NMR (DMSO-$d_6$) δ 1.22 (t, J=7.0 Hz, 3H), 1.35 (s, 9H), 3.54 (d, J=5.9 Hz, 2H), 3.71–3.88 (m, 6H), 4. 07 (q, J=7.0 Hz, 2H), 6.18 (d, J=8.1 Hz, 1H), 6.96 (br t, 1H), 7.44–7.95 (m, 7H), 8.07 (d, J=7.4 Hz, 1H), 8.26 (t, J=5.7 Hz, 1H), 8.53 (t, J=5.76 Hz, 1H), 8.64 (d, J=7.7 Hz, 1H).

F. Synthesis of Gly-Gly-1-naphthylGly-Gly-Gly

Boc-Gly-Gly-1-naphthylGly-Gly-Gly-OEt prepared as in Example 32E (5.0 g, 8.98 mmol) was dissolved in acetic acid:HCl (4:1, v/v) solution (200 ml) and the mixture was stirred at room temperature for 12 h. The mixture was concentrated in vacuo and the resulting residue was washed with $Et_2O$ to yield 3.4 g (88%) of Gly-Gly-1-naphthylGly-Gly-Gly as a white solid: mp 252°–3° C. (dec); $^1H$ NMR (DMSO-$d_6$) δ 3.56 (d, J=5.9 Hz, 2H) , 3.71–3.91 (m, 6H), 6.21 (d, J=7.8 Hz, 1H), 7.47 (t, J =7.7 Hz, 1H), 7.49–7.64 (m, 4H), 7.87 (d, J=8.2 Hz, 1H), 7.93 (d, J=7.4 Hz, 1H), 8.06 (d, J=8.0 Hz, 1H), 8.22–8.28 (m, 3H), 8.59 (br t, 1H), 8.68 (t, J=5.5 Hz, 1H), 8.84 (d, J=7.8 Hz, 1H).

G. Synthesis of Cyclo-(Gly-Gly-1-naphthylGly-Gly-Gly-)

The compound was synthesized by the method of Veber, D. F. et al, *J. Org. Chem.* 44, 3101–5 (1979). The pentapeptide Gly-Gly-1-naphthylGly-Gly-Gly prepared as in Example 32F (3.14 g, 7.3 mmol) was dissolved in degassed DMF (800 ml) and the pH of the solution was adjusted to 7.2 with triethylamine. Diphenylphosphoryl azide (1.88 ml, 8.77 mmol) was added at −20° C. The mixture was stirred for 2 days at −20° C. and for 2 days at 2° C. maintaining the pH when necessary between 7–7.5 by the addition of triethylamine. Water (800 ml) and Biorad AG 501-X8(D) resin (200 g) was added to the reaction mixture and the mixture was stirred for 6 h. The resin was separated by filtration and the filtrate was concentrated in vacuo to give 1.6 g (53% yield) of cyclo-(Gly-Gly-1-naphthylGly-Gly-Gly-) as a white solid: mp 256°–8° C.; $^1H$ NMR (DMSO-$d_6$) δ 3.62–4.06 (m, 9H), 6.33 (d, J=7.8 Hz, 1H), 7.25 (d, J=7.4 Hz, 1H), 7.40 (t, J=7.7 Hz, 1H), 7.46–8.25 (m, 7H), 8.29 br t, 1H), 8.59 (d, J=7.8 Hz, 1H), 8.74 (t, J=5.5 Hz, 1H); FAB mass spectrum (NBA) m/z 412, ($M^+$+H).

H. Synthesis of 2-(1-Naphthyl)-1,4,7,10,13-pentaazacyclopentadecane

Cyclo-(Gly-Gly-1-naphthylGly-Gly-Gly-) prepared as in Example 32G (3.4 g, 8.26 mmol) was suspended in a 0.5M solution of $LiAlH_4$ in dimethoxyethane (100 ml) and was refluxed under a dry nitrogen atmosphere for 4 days. The mixture was cooled and quenched with water (10 ml) and 1N NaOH solution (10 ml). The reaction mixture was filtered and concentrated in vacuo to dryness. The resulting solid was triturated with $Et_2O$ (5×50 ml). The combined $Et_2O$ extracts were concentrated in vacuo to give 0.55 g (20% yield) of 2-(1-naphthyl)-1,4,7,10,13-pentaazacyclopentadecane which was crystallized from hot acetonitrile as a white solid: mp 87°–8° C.; $^1H$ NMR ($CDCl_3$) δ 2.00 (br m, 5H); 2.49–3.05 (m, 19H), 4.59 (dd, J=10.0, 2.0 Hz, 1H), 7.44–7.52 (m, 4H), 7.67 (d, J=7.0 Hz, 1H), 7.86 (d, J=7.0 Hz, 1H), 8.18 (d, J=7.7 Hz, 1H). FAB mass spectrum (NBA+$Li^+$) m/z 348 ($M^+$+Li). Exact mass (M+Li)$^+$: calcd, 348.2740; found, 348.2756 ($C_{20}H_{31}N_5Li$).

I. Synthesis of 2-(1-Naphthyl)-1,4,7,10,13-pentaazacyclopentadecane (Alternate method)

Cyclo-(Gly-Gly-1-naphthylGly-Gly-Gly (0.162 g, 0.40 mmol) was suspended in a 1M solution of $BH_3$.pyridine (6 ml) and refluxed under a dry nitrogen atmosphere for three days. The mixture was cooled and quenched with 6N HCl (10 ml) and neutralized with 1N NaOH solution. The reaction mixture was concentrated to dryness in vacuo and the resulting solid was triturated with $Et_2O$ (5×20 ml). The $Et_2O$ extracts were concentrated in vacuo to give 66 mg (48% yield) of 2-(1-naphthyl)-1,4,7,10,13-pentaazacyclopentadecane which was crystallized from hot acetonitrile to give a white solid: mp 87°–8° C,; $^1$NMR ($CDCl_3$) δ 2.00 (br m, 5H); 2.49–3.05 (m, 19H), 4.59 (dd, J=10.0, 2.0 Hz, 1H), 7.44–7.52 (m, 4H), 7.67 (d, J=7.0 Hz, 1H), 7.86 (d, J=7.0 Hz, 1H), 8.18 (d, J=7.7 Hz, 1H); FAB mass spectrum (NBA+Li) m/z 348 (M+Li)$^+$; Exact mass (M+Li)$^+$: calcd, 348.2740; found, 348.2756 ($C_{20}H_{31}N_5Li$).

J. Synthesis of {Manganese(II)dichloro[2-(1-Naphthyl)-1,4,7,10,13-pentaazacyclopentadecane]}

2-(1-Naphthyl)-1,4,7,10,13-pentaazacyclopentadecane prepared as in Example 32H (0.23 g, 0.67 mmol) was added to a refluxing anhydrous MeOH solution (50 ml) containing anhydrous manganese(II) chloride (84.4 mg, 0.671 mmol) under a dry nitrogen atmosphere. The solution was refluxed overnight and then filtered through celite. The solution was taken to dryness and the residue was redissolved in hot EtOH (10 ml). The resultant yellowish solution was filtered through celite and ethyl ether (30 ml) was added. A flocculent yellowish precipitate formed which was filtered and discarded. The filtrate was diluted to 50 ml with ethyl ether and allowed to sit undisturbed for 4 days. A white microcrystalline precipitate was collected by filtration to give 0.144 g (46% yield) of product after drying in vacuo: FAB mass spectrum (NBA) m/z (relative intensity) 466 (M$^+$, 3), 431/433 [(M$^+$–Cl), 100/32]; Anal. calcd for $C_{20}H_{31}N_5MnCl_2$: C, 51.40; H, 6.69; N, 14.99. Found: C, 52.10; H, 6.73; N, 14.71.

EXAMPLE 33

A. Synthesis of DAla-Gly-Gly-OBzl.HCl

A suspension of DAla-Gly (5.0 g, 24.6 mmol) in benzyl alcohol (75 ml) was cooled to 0° C. and anhydrous HCl gas was bubbled through the mixture for 30 min. The resulting solution was stored at ~–30 ° C. overnight. The mixture was concentrated in vacuo and the resulting oil crystallized upon the addition of methanol (~25 ml). The solid was isolated by filtration, coevaporated with water (2×250 ml) to remove residual methanol and finally coevaporated with toluene (2×250 ml). This treatment afforded 7.10 g (88% yield) of the benzyl ester as a white powder: $^1$H NMR (DMSO-$d_6$) δ 1.38 (d, J=6.8 Hz, 3H), 3.81–3.95 (m, 5H), 5.14 (s, 2H), 7.38 (s, 5H), 8.33 (br s, 3H), 8.57 (t, J=5.6 Hz, 1H), 8.84 (t, J=5.5 Hz, 1H).

B. Synthesis of Boc-Gly-Ala

To a solution of Gly-Ala (25.0 g, 171 mmol) in THF (350 ml) and 0.5N sodium hydroxide (350 ml) at 0 ° C. was added (Boc)$_2$O (41.3 g, 189 mmol). The pH was maintained at ~10 over a 5 h period (with 1.0N sodium hydroxide) and the reaction was stirred for 12 h thereafter at room temperature. The pH was again adjusted to ~10 with 1.0N sodium hydroxide, the THF layer was separated, and the aqueous solution was washed with ethyl acetate (2×250 ml). The pH was adjusted to 3.0 with 1.0N sodium bisulfate and this solution was extracted with ethyl acetate (2×250 ml). The combined extracts. were dried (magnesium sulfate), filtered and concentrated in vacuo to afford 38.2 g (91% yield) of the product as a white powder: $^1$H NMR (DMSO-$d_6$) δ 1.26 (d, J=7.3 Hz, 3H), 1.38 (s, 9H), 3.45–3.62 (m, 2 H), 4.18–4.25 (m, 1H), 6.88 (t, J=5.6 Hz, 1H), 7.99 (d, J=7.2 Hz, 1H).

C. Synthesis of Boc-Gly-Ala-DAla-Gly-Gly-OBzl

To a solution of Boc-Gly-Ala prepared as in Example 33B (10.2 g, 41.5 mmol) in anhydrous DMF (300 ml), was added HOBT●H$_2$O (6.21 g, 46.0 mmol), EDC●HCl (8.81 g, 46.0 mmol) and DAla-Gly-Gly-OBzl●HCl (13.7 g, 41.5 mmol). The pH of the resulting solution was adjusted to ~8 (measured by spotting the reaction mixture on moistened Hydrion paper) and the reaction mixture was allowed to stir at room temperature for 12 h thereafter. The solution was concentrated in vacuo and the residue was dissolved in water (40 ml). The resulting solution Was extracted with ethyl acetate (3×150 ml). The combined ethyl acetate layers were washed with 1N sodium bisulfate (100 ml), saturated sodium bicarbonate (100 ml) and brine (100ml). The ethyl acetate solution was dried (magnesium sulfate), filtered and concentrated to half volume. The product crystallized out upon standing at RT for 30 min. Collection of the crystals by filtration and drying at high vacuum afforded 17.4 g (80% yield) of the pure product: $^1$H NMR (DMSO-$d_6$) δ 1.21 (d, J=7.4 Hz, 3H), 1.23 (d, J=7.3 Hz, 3H), 1.38 (s, 9H), 3.56 (d, J=6.3 Hz, 2H), 3.75 (d, J=5.7 Hz, 2H), 3.93 (d, J=6.0 Hz, 2H), 4.24–4.34 (m, 2H), 5.14 (s, 2H), 6.98 (t, J=5.7 Hz, 1H), 7.34–7.40 (m, 5H), 7.93 (d, J=7.2 Hz, 1H), 8.17–8.24 (m, 3H).

D. Synthesis of Gly-Ala-DAla-Gly-Gly●HCl

To Boc-Gly-Ala-DAla-Gly-Gly-OBzl prepared as in Example 33C (17.2 g, 33.0 mmol) in glacial acetic acid (480 ml) was added 6N HCl (120 ml) and the reaction mixture was stirred at room temperature for 24 h. Concentration in vacuo followed by coevaporation with water (2×250 ml) and toluene (2×250 ml) afforded 12.9 g (100% yield) of the product as a white powder: 1H NMR (D$_2$O) δ 1.36 (d, J=6.9 Hz, 3H), 1.38 (d, J=7.2 Hz, 3H), 3.84 (s, 2H), 3.96 (s, 2H), 3.99 (s, 2H), 4.30–4.36 (m, 2H).

E. Synthesis of cyclo-(Gly-Ala-DAla-Gly-Gly-)

This compound was synthesized by the method of Veber, D. F. et al, J. Org. Chem., 44, 3101–5 (1979). To a solution of Gly-Ala-DAla-Gly-Gly●HCl prepared as in Example 33D (12.9 g, 35.0 mmol) in anhydrous DMF (4400 ml) was added enough TEA to adjust the pH to ~8 (measured by spotting the reaction mixture on moistened Hydrion paper) and the resulting mixture was cooled to –25° C. To this mixture was added DPPA (9.20 ml, 43.0 mmol) dropwise over 5 min. The reaction was stored at –25° C. (internal temperature) for 48 h thereafter. During this time the pH was monitored periodically (as described above) and maintained at ~8 by the addition of TEA. After this time the reaction mixture was allowed to stand at 0° C. for 48 h. Again the pH was monitored periodically and maintained at ~8 by the addition of TEA. After this time the reaction mixture was diluted with water (4400 ml) and stirred with Bio-Rad AG 501-X8 (mixed-bed) resin (200 g) for 6 h. The resin was separated by filtration and the solution was concentrated to dryness. Trituration of the residue with refluxing THF (250 ml) for 3 h, filtration of the hot THF and drying at high vacuum afforded 6.61 g (60% yield) of the product as a white powder: $^1$H NMR (DMSO-$d_6$) δ 1.15–1.32 (m, 6H), 3.45–4.00 (m, 6H), 4.10–4.38 (m, 2H), 7.81 (d, J=7.8 Hz, 1H), 7.97 (t, J=6.6 Hz, 1H), 8.10 (m, 2H), 8.18 (d, J=7.5 Hz, 1H).

F. Synthesis of (2S, 5R)-Dimethyl-1,4,7,10,13-pentaazacyclopentadecane

An oven-dried 500 ml flask containing a glass stir-bar was allowed to cool to room temperature under argon flow and charged with cyclo-(Gly-Ala-DAla-Gly-Gly-) (5.10 g, 16.3 mmol) and THF (74.0 ml). To this stirred suspension was added 1.0M LiAlH$_4$ in THF (196 ml, 196 mmol) dropwise over 10 min. The suspension was stirred for 1 h at RT and became homogeneous during this time. The mixture was then refluxed for 48 h. The mixture was cooled to —20° C. and quenched (cautiously) with saturated sodium sulfate (50 ml). The resulting mixture was concentrated in vacuo to a dry white powder, and this mixture was triturated with methylene chloride (3×100 ml). The combined triturates were concentrated in vacuo and the resulting residue was recrystallized from acetonitrile and then from hexanes to afford 2.23 g (56% yield) of the pure product as a white solid: mp 114°–6° C.; $[\alpha]_d^{20}$=–4.76° (c=0.008, methanol); $^1$H NMR (CDCl$_3$) δ 0.99 (d, J=6.0 Hz, 3H), 1.00 (d, J=6.3 Hz, 3H), 1.82 (bs, 5H), 2.08 (apparent t, J=10.7 Hz, 1H), 3.20 (dd, J=11.3, 10.0 Hz, 1H), 2.45–2.95 (m, 16H); Exact mass (M+H)$^+$: calcd., 244.2501; found, 244.2516 (C$_{12}$H$_{30}$N$_5$). Anal. calcd. for C$_{12}$H$_{29}$N$_5$: C, 59.22; H, 12.01; N, 28.77. Found: C, 58.76; H, 11.96; N, 28.46.

G. Synthesis of {Manganese(II)dichloro[(2S, 5R)-Dimethyl-1,4,7,10,13-pentaazacyclopentadecane]}

A solution of (2S,5R)-dimethylpentaazacyclopentadecane prepared as in Example 33F (367 mg, 1.51 mmol) and anhydrous manganese(II) chloride (189 mg, 1.51 mmol) in anhydrous methanol (50 ml) were refluxed for 2 h and stirred at room temperature overnight. The solution was filtered through celite and taken to dryness in vacuo. The residue was recrystallized from ethanol-ether to afford 340 mg (61% yield) of the product as a white solid: $[\alpha]_d^{20}$=–9.75° (c=0.006, methanol); FAB mass spectrum (relative intensity); 368 [(M–H)$^+$, 1], 333/335 [(M–Cl)$^+$, 100/35]. Anal. calcd. for C$_{12}$H$_{29}$N$_5$Cl$_2$Mn: C, 39.03; H, 7.92; N, 18.97. Found: C, 39.26; H, 7.96N, 19.00.

EXAMPLE 34

A. Synthesis of DAla-Gly-OBzl●HCl

A suspension of DAla-Gly (10.0 g, 68.42 mmol) in benzyl alcohol (150 ml) was cooled to 0° C. and anhydrous HCl gas was bubbled through the mixture for 30 min. The resulting solution was stoppered and stored in a freezer (0° C.) overnight. The mixture was concentrated in vacuo. The resulting oil was dissolved in a minimal amount of methanol (~50 ml) and precipitated with the addition of ether (700 ml). Filtration and drying at high vacuum afforded 15.2 g (82% yield) of the benzyl ester hydrochloride as a white solid: $^1$H NMR (DMSO-d$_6$) δ 1.40 (d, J=7.0 Hz, 3H), 3.91–4.02 (m, 3H), 5.15 (s, 2H), 7.34 (s, 5H), 8.44 (bs, 3H), 9.15 (t, J=5.6 Hz, 1H).

B. Synthesis of BoC-Gly-Ala-Gly

To a solution of Gly-Ala-Gly (10.0 g, 49.2 mmol) in THF (100 ml) and 0.5N sodium hydroxide (100 ml) at 0° C. was added (Boc)$_2$O (11.9 g, 54.5 mmol). The pH was maintained at ~10 over a 5 h period (with 1.0N sodium hydroxide) and the reaction was stirred for 12 h thereafter at room temperature. The pH was adjusted to ~10 and washed with ethyl acetate (100 ml). The pH was then adjusted to ~2 with 1N potassium bisulfate and extracted with ethyl acetate (2×100 ml). The combined extracts were dried (magnesium sulfate), filtered and concentrated to afford 11.0 g (74% yield) of the product as a white powder: $^1$H NMR (DMSO-d$_6$) δ 1.22 (d, J=7.0 Hz, 3H), 1.34 (s, 9H), 3.57 (d, J=5.9 Hz, 2H), 3.75 (d, J=6.0 Hz, 2H), 4.33 (apparent quint., J=7.0 Hz, 1H), 6.96 (t, J=6.1 Hz, 1H), 7.93 (d, J=7.0 Hz, 1H), 8.22 (t, J=5.7 Hz, 1H).

C. Synthesis of Boc-Gly-Ala-Gly-DAla-Gly-OBzl

To a solution of Boc-Gly-Ala-Gly prepared as in Example 34B (11.0 g, 36.5 mmol) in anhydrous DMF (270 ml), was added HOBT●H$_2$O (5.46 g, 40.4 mmol), EDC●HCl (7.74 g, 40.4 mmol), and DAla-Gly-OBzl ●HCl prepared as in Example 34A (9.95 g, 36.5 mmol). The pH of the resulting solution was adjusted to ~8 (measured by spotting the reaction mixture on moistened Hydrion paper) and the reaction mixture was allowed to stir at room temperature for 12 h thereafter. The solution was concentrated in vacuo and the residue was dissolved in water (50 ml). This solution was extracted with ethyl acetate (3×100 ml). The combined ethyl acetate layers were washed with 1N sodium bisulfate (50 ml), saturated sodium bicarbonate (50 ml) and brine (50 ml). The ethyl acetate solution was dried (magnesium sulfate), filtered and allowed to sit for 12 h undisturbed. Collection of the crystals by filtration and drying at high vacuum afforded 13.4 g (70% yield) of pure product: $^1$H NMR (DMSO-d$_6$) δ 1.22 (d, J=7.2 Hz, 3H), 1.23 (d, J=7.2 Hz, 3H), 1.38 (s, 9H), 3.58 (d, J=6.0 Hz, 2H), 3.73 (d, J=4.8 Hz, 2H), 3.91 (dd, J =6.0, 3.0 Hz, 2H), 4.32 (m, 2H), 5.14 (s, 2H), 6.91 (t, J=4.8 Hz, 1H), 7.38 (s, 5H), 7.97 (d, J=8.1 Hz, 1H), 8.02 (d, J=6.9 Hz, 1H), 8.19 (t, J=5.4 Hz, 1H), 8.33 (t, J=5.4 Hz, 1H).

D. Synthesis of Gly-Ala-Gly-DAla-Gly●HCl

To Gly-Ala-Gly-DAla-Gly-OBzl prepared as in Example 34C (13.4 g, 25.7 mol) in glacial acetic acid (400 ml) was added concentrated HCl (100 ml) and the reaction mixture was stirred at room temperature for 24 h. The solution was concentrated in vacuo, dissolved in water (100 ml) and the resulting aqueous solution was washed with ether (2×50 ml) and concentrated again in vacuo. Drying at high vacuum afforded 9.70 g (100% yield) of the product as a white powder: $^1$H NMR (D$_2$O) δ 1.38 (d, J=7.2 Hz, 3H), 1.39 (d, J=7.2 Hz, 3H), 3.84 (s, 2H), 3.92 (s, 2H), 3.96 (s, 2H), 4.34 (m, 2 H).

E. Synthesis of Cyclo-(Gly-Ala-Gly-DAla-Gly-)

This compound was synthesized by the method of Veber, D. F. et al, J. Org. Chem. 44, 3101–5 (1979). To a solution of Gly-Ala-Gly-DAla-Gly●HCl prepared as in Example 34D (9.70 g, 26.4 mmol) in anhydrous DMF (3200 ml) was added enough TEA to adjust the pH to ~8 (measured by spotting the reaction mixture on moistened Hydrion paper) and the resulting mixture was cooled to –40° C. To this mixture was added DPPA (8.86 g, 32.2 mmol) dropwise over 5 min. The temperature was maintained at ~–35 ° C. for a period of 5 h and then the reaction mixture was stored at –25° C. (internal temperature) for 48 h thereafter. During this time the pH was monitored periodically (as described above) and maintained at ~8 by the addition of TEA. After this time the reaction mixture was allowed to stand at 0° C. for 48 h. Again the pH was monitored periodically and maintained at ~8 by the addition of TEA. After this time the reaction was diluted with water (3200ml) and stirred with Bio-Rad AG 501-X8 (mixed-bed) resin (1500 g) for 6 h. The resin was separated by filtration and the solution was concentrated to dryness. Trituration of the residue with refluxing THF for 12 h, filtration of the hot THF and drying at high vacuum afforded 5.50 g (67 % yield) of the product as a white powder: mp >300° C. (dec); $^1$H NMR (DMSO-d$_6$) δ 1.16–1.25 (m, 6H), 3.38–4.23 (m, 8H), 7.55 (t, J=5.6 Hz, 1H), 7.60 (t, J=5.4 Hz, 1H), 8.20–8.25 (m, 1H), 8.40 (d, J=7.6 Hz, 1H); FAB mass spectrum (NBA+Li$^+$) m/z 320 (M+Li)$^+$.

F. Synthesis of (2S,8R)-Dimethyl-1,4,7,10,13-pentaazacyclopentadecane

An oven-dried flask containing a glass stir-bar was allowed to cool to room temperature under argon flow and charged with cyclo-(Gly-Ala-Gly-DAla-Gly-) (4.0 g, 12.8 mmol) and THF (30 ml). To this stirred suspension was added a 1.0M solution of lithium aluminum hydride in THF (153 ml, 153 mmol) dropwise. The reaction mixture was stirred at room temperature for 1 h and heated to reflux for 48 h thereafter. The mixture was then cooled to –20° C. and quenched (cautiously) with saturated sodium sulfate solution (50 ml). The resulting mixture was concentrated in vacuo to a dry white powder, and this mixture was triturated with methylene chloride (3×100 ml). The combined methylene chloride layers were concentrated in vacuo and the residue was recrystallized from acetonitrile to afford 1.22 g (39% yield) of the pure product as a white solid: mp 130°–2° C.;$[\alpha]_d^{20}$=+2.73° (c=0.011,methanol); $^1$H NMR (CDCl$_3$) δ 0.95 (d, J=6.2 Hz, 6H), 1.79 (br s, 5H), 2.31 (apparent q, J=12.0 Hz, 2H), 2.50–2.84 (m, 16H); FAB mass spectrum (NBA+Li$^+$) m/z 250 (M+Li)$^+$. Anal. calcd. for $C_{12}H_{29}N_5$: C, 59.22; H, 12.01; N, 28.77. Found: C, 58.71; H, 11.95; N, 28.50.

G. Synthesis of {Manganese(II)dichloro[(2S,8R)-Dimethyl-1,4,7,10,13-penta-azacyclopentadecane]}

A solution of (2S,8R)-dimethyl-1,4,7,10,13-pentaazacyclopentadecane prepared as in Example 34F (610 mg, 2.51 mmol) and anhydrous manganese(II) chloride (315 mg, 2.51 mmol) were refluxed in anhydrous methanol (50 ml) for 2 h and stirred at room temperature overnight. The solution was filtered through celite, concentrated and crystallized from methanol-ether to afford 160 mg (17% yield) of the product: $[\alpha]_d^{20}$=–9.73° (c=0.005, methanol)FAB mass spectrum (relative intensity); 333/335 [(M–Cl)$^+$, 100/ 30]. Exact mass (M–Cl)$^+$;calcd., 333.1492; found, 333.1446 ($C_{12}H_{25}N_5$MnCl).

EXAMPLE 35

A. Synthesis of trans-5,6-Cyclohexano-1,10,13-tris (p-toluenesulfonyl)-1,4,7,10,13-pentaazacyclopentadecan-3,8-dione Dry dichloromethane (150 ml) was placed in a one liter four necked round bottom flask under argon equipped with two dropping funnels. 3,6,9-Tris(p-toluenesulfonyl)-3,6,9-triazaundecanedioyl dichloride prepared as in Example 28G (5.07 g, 7.05 mmol) was dissolved in dry dichloromethane (150 ml) and added to one of the dropping funnels. trans-1,2-Diaminocyclohexane (0.805 g, 7.05 mmol) and triethylamine (1.96 ml, 14.1 mmol) were dissolved in dry dichloromethane (150 ml) and added to the other dropping funnel. After cooling the dichloromethane containing flask in an ice bath to an internal temperature of 0° to 5° C., the contents of the dropping funnels were added simultaneously to the stirred solution over 2.25 h. A white precipitate was evident before the addition was finished. At the end of this time, the ice bath was removed and the reaction mixture was stirred overnight at room temperature. The reaction mixture was filtered and the white precipitate was identified as pure product. The filtrate was washed twice with water (100 ml), once with saturated sodium chloride solution (100 ml), dried (MgSO$_4$), filtered, and the solvent was removed under reduced pressure. Recrystallization from dichloromethane-hexane provided additional product, along with the initial precipitate for a total of 2.85 g (53% yield); mp 254°–5° C.; $^1$H NMR (DMSO-d$_6$) δ 1.15 (br s, 4H), 1.52–1.75 (m, 4H), 2.42 and 2.43 (2 s, 9H), 3.04 (m, 8H), 3.51 (d+m, J=16.5 Hz, 4H), 4.01 (d, J=16.5 Hz, 2H), 7.35–7.53 (m, 8H) , 7.71 (d, J=8.3 Hz, 4H), 7.80 (br d, J=10.5 Hz, 2H).

B. Synthesis of trans-1,2-Bis(chloroacetamido) cyclohexane

A 12 liter three-neck flask equipped with a magnetic stirbar and two 1 liter dropping funnels was charged with 1,2-diaminocyclohexane (35.0 g, 0.310 mol) dissolved in chloroform (375 ml) and water (185 ml). The two dropping funnels were charged individually with chloroacetyl chloride (75 ml, 0.94 mol) in chloroform (440 ml) and potassium carbonate (120.5 g, 0.87 mol) in water (4 l), added in four portions during the addition. The flask was cooled in an ice salt bath and addition of the reagents was carried out over 2 h. The ice salt bath was removed, water (600 ml) was added, and the reaction mixture was stirred for 2.5 h. The mixture was separated and the water layer was extracted with chloroform several times. The combined chloroform layers were washed with water and then brine. The organic layer was dried (sodium sulfate) and concentrated in vacuo to yield an off-white solid. The solid was washed with ether to yield 55.32 g (67% yield) of a white solid after drying in vacuo: mp 202°–3° C.; $^1$H NMR (CDCl$_3$) δ 1.27–1.50 (m, 4H), 1.75–1.95 (m, 2H) , 2.03–2.20 (m, 2H), 3.72–3.87 (m, 2H), 4.05 (s, 4H), 6.81 (br s, 2H).

C. Synthesis of trans-5,6-Cyclohexano-1,10,13-tris (p-toluenesulfonyl)-1,4,7,10,13-pentaazacyclopentadecan-3,8-dione (alternate method)

A 5 liter three-neck flask equipped with a magnetic stir bar and 1 liter dropping funnel was dried and placed under a dry argon atmosphere. A solution of trans-1,2-bis (chloroacetamido)cyclohexane prepared as in Example 35B (6.68 g, 250 mmol) in anhydrous DMF (1.25 l) was added to a solution of 1,4,7-tris(p-toluenesulfonyl)-1,4,7-triazaheptane-1,7-disodium salt prepared as in Example 1B (15.2 g, 250 mmol) in anhydrous DMF (1.25 l) at room temperature over a period of 12 h. After stirring an additional 2 h, the solvent was removed in vacuo. The solid residue was triturated with chloroform (1 l) and filtered to yield a white solid. The solid was recrystallized from acetonitrile to give 7.22 g (38% yield) of fluffy white crystals: mp 254°–5° C.; $^1$H NMR (DMSO-d$_6$) δ 1.15 (br s, 4H), 1.52–1.75 (m, 4H), 2.42 and 2.43 (2 s, 9H), 3.04 (m, 8H), 3.51 (d+m, J=16.5 Hz, 4H) , 4.01 (d, J=16.5 Hz, 2H), 7.35–7.53 (m, 8H), 7.71 (d, J=8.3 Hz, 4H), 7.80 (br d, J=10.5 Hz, 2H).

D. Synthesis of trans-2,3-Cyclohexano-1,4,7,10,13-pentaazacyclopentadecane trans-5,6-Cyclohexano-1,10,13-tris(p-toluenesulfonyl)-1, 4,7,10,13-pentaazacyclopentadecan-3,8-dione prepared as in Example 35A (1.765 g, 2.32 mmol) was suspended in 1,2-dimethoxyethane (dme, 40 ml) under argon, and the flask was placed in a water bath. Lithium aluminum hydride (0.5M in dme, 55 ml, 27.5 mmol) was added over a 5 min period. Five min later heating with a mantle was started, and reflux began 15 min later. The reaction became almost colorless after a few min of reflux, later turning yellow with white precipitate. Reflux was continued for 43.5 h, and then the reaction mixture was allowed to cool to room temperature. The reaction was quenched by the careful addition of water (0.86 ml) using a water bath for cooling. Five min later, 15% aqueous sodium hydroxide solution (0.86 ml) was added followed by water (2.6 ml). The slight yellowish color largely discharged during this process. One h later, tetrahydrofuran (55 ml) was added and stirring was continued for 2 h. The quenched reaction mixture was filtered. The filtrate was evaporated under reduced pressure and placed on the vacuum line, giving a yellowish-white solid. This solid was dissolved in dichloromethane and filtered, then concentrated to a solid and placed on the vacuum line. It was recrystallized from hot acetonitrile under argon, producing 0.316 g (50% yield) of white needles: mp 112°–3° C. (under nitrogen); $^1$H NMR (CDCl$_3$) δ 0.97 (m, 2H), 1.22 (m, 2H), 1.39–1.96 (3 m, 7H), 2.11 (m, 4H), 2.49 (m, 2H), 2.54–2.88 (several m, 12H), 2.94 (m, 2 H); Exact mass (M+H)$^+$: calcd, 270.2658; found, 270.2658 (C$_{14}$H$_{32}$N$_5$).

E. Synthesis of [Manganese(II)dichloro(trans-2,3-Cyclohexano-1,4,7,10,13-pentaazacyclopentadecane)].

trans-2,3-Cyclohexano-1,4,7,10,13-pentaazacyclopentadecane prepared as in Example 35D (301 mg, 1.12 mmol) was added to a hot anhydrous MeOH solution (50 ml) containing anhydrous manganese(II) chloride (140 mg, 1.12 mmol) under a dry nitrogen atmosphere. After refluxing for 2 h, the solution was stirred overnight at room temperature and was then taken to dryness. The white solid was dissolved in warm acetone-(15 ml) and the solution was filtered. The solution was stripped to dryness and the white solid was washed with ethyl ether. The solid was dried in vacuo to give 0.36 g (82% yield) of product: FAB mass spectrum (NBA) m/z (relative intensity) 394 (M$^+$, 1), 359/361 [(M–Cl)$^+$, 100/29]; Anal. calcd. for C$_{14}$H$_{31}$N$_5$MnCl$_2$: C, 42.54; H, 7.91; N, 17.72. Found: C, 42.56; H, 8.17; N, 17.42.

EXAMPLE 36

A. Synthesis of cis-5,6-Cyclohexano-1,10,13-tris(p-toluenesulfonyl)-1,4,7,10,13-pentaazacyclopentadecan-3,8-dione Dry dichloromethane (250 ml) was placed in a two liter four necked round bottom flask under argon equipped with two dropping funnels, argon inlet, and magnetic stir bar. 3,6,9-Tris(p-toluenesulfonyl)-3,6,9-triazaundecanedioyl dichloride prepared as in Example 28G (9.0 g, 12.5 mmol) was dissolved in dry dichloromethane (250 ml) and added to one of the dropping funnels. cis-1,2-Diaminocyclohexane (1.43 g, 12.5 mmol) and triethylamine (3.5 ml, 22.25 mmol) were dissolved in dry dichloromethane (250 ml) and added to the other dropping funnel. The flask was placed in an ice bath and simultaneous dropwise addition of the contents of the two addition funnels was carried out over a 3 h period. The reaction was then allowed to warm to room temperature and stir overnight. The homogeneous solution was partially evaporated on the rotary evaporator, to a volume of about 300 ml. Water (250 ml) was added with vigorous stirring, causing a white solid to come out. After filtration and drying in a vacuum oven at 50° C. overnight, 6.21 g were recovered. Additional recovery of 0.06 g from the dichloromethane layer, after recrystallization from dichloromethanehexane, gave a total of 6.27 g (66% yield): mp 251°–2° C.; $^1$H NMR (CDCl$_3$) δ 1.41–1.64 (br m, 6H), 1.76 (m, 2 H), 2.45 (s, 9H), 3.18 (m, 2H), 3.29–3.58 (several m, 8H), 3.82 (d, J=16.9 Hz, 2H), 4.16 (br s, 2H), 6.86 (d, J=7.3 Hz, 2H), 7.31–7.40 (m, 6H), 7.70 and 7.73 (2 d, J=8.3 and 8.3 Hz, 6H).

B- Synthesis of cis-5,6-Cyclohexano-1,4,7,10,13-pentaazacyclopentadecane

The cis-5,6-cyclohexano-1,10,13-tris(p-toluenesulfonyl)-1,4,7,10,13-pentaazacyclopentadecan-3,8-dione prepared as in Example 36A (4.0 g, 5.26 mmol) was suspended in 1,2-dimethoxyethane (dme, 90 ml) and stirred under argon in a 3 necked round bottom flask while the lithium aluminum hydride (0.5M in dme, 125 ml, 62.5 mmol) was added over a 5 minute period using a water bath for cooling. The reaction mixture became almost colorless before the end of the addition. After 5 more min in the water bath, heating in a mantle was started, and reflux was attained 15 min later. The reaction became yellow after a few minutes of reflux and soon showed a white precipitate. After 43 h, reflux was stopped and the reaction mixture was cooled to room temperature. Water (1.95 ml) was carefully added dropwise, using a water bath for cooling. Five min later, 15% aqueous sodium hydroxide solution (1.95 ml) was added, followed by more water (5.75 ml). The slight yellowish color largely discharged during this process. Stirring was continued for 1.25 h and nitrogen saturated tetrahydrofuran (120 ml) was added and stirring was continued. The quenched reaction mixture was filtered and the filtrate was concentrated. About halfway through the concentration, the filtrate was filtered again to remove some solid which had been present after the previous filtration. On completion of solvent removal and drying on the vacuum line, a white solid was obtained (1.31 g). NMR showed that 20 to 30% of the trans isomer was present in addition to the desired compound. After several recrystallizations from acetonitrile, the amount of the trans isomer present had decreased. A final recrystallization of several combined fractions from hot hexane gave 400 mg (28% yield) of nearly pure cis isomer containing less than 4% of the trans isomer: mp 114°–5° C. (under nitrogen); $^1$H NMR (CDCl$_3$) δ 1.23–1.88 (several m, 13H), 2.53–2.92 (several m, 18 H); Exact mass (M+H)$^+$: calcd, 270.2658; found, 270.2701 (C$_{14}$H$_{32}$N$_5$).

C. Synthesis of [Manganese(II)dichloro(cis-5,6-Cyclohexano-1,4,7,10,13-pentaazacyclopentadecane)]

cis-5,6-Cyclohexano-1,4,7,10,13-pentaazacyclopentadecane prepared as in Example 36B (0.35 g, 1.3 mmol) was added to a hot anhydrous MeOH solution (50 ml) containing anhydrous manganese(II) chloride (0.163 g, 1.30 mmol) under a dry nitrogen atmosphere. After refluxing for 2 h, the solution was stirred overnight at room temperature and was then taken to dryness. The solid was extracted with a 4:1 acetone/MeOH solution (25 ml). The extract was filtered and ethyl ether was added to the filtrate. After sitting at 0° C., a white solid precipitated which was collected by filtration. After washing with ethyl ether and drying in vacuo, 0.353 g (69% yield) of product as a white solid was obtained: FAB mass spectrum (NBA) m/z (relative intensity) 394 (M$^+$, 2), 359/361 [(M–Cl)$^+$, 100/31]; Anal. calcd for C$_{14}$H$_{31}$N$_5$MnCl$_2$: C, 42.54; H, 7.91; N, 17.72. Found: C, 42.60; H, 8.17; N, 17.18.

Example 37

A. Synthesis of 5,6-Benzo-1,10,13-tris(p-toluenesulfonyl)-1,4,7,10,13-pentaazacyclopentadecan-3,8-dione Dry dichloromethane (250 ml) was placed in a two liter four necked round bottom flask under argon equipped with two dropping funnels, argon inlet, and magnetic stir bar. 3,6,9-Tris(p-toluenesulfonyl)-3,6,9-triazaundecanedioyl dichloride prepared as in Example 28G (11.0 g, 15.31 mmol) was dissolved in dry dichloromethane (250 ml) and added to one of the dropping funnels. o-Phenylenediamine (1.66 g, 15.31 mmol) was dissolved in CH$_2$Cl$_2$ (250 ml) and added to the other dropping funnel. After cooling the reaction flask in an ice bath, simultaneous dropwise addition of the solutions in the two dropping funnels was carried out over 2.5 h. The ice bath was then removed and the reaction was stirred overnight. At the end of this time, the solvent was partially removed on the rotary evaporator to a volume of about 350 ml, and water (250 ml) was added. With vigorous stirring a white solid precipitated, was filtered and dried in a vacuum oven at 50° C. overnight. The dichloromethane phase was separated, the solvent was removed, and the residue was recrystallized from dichloromethane-hexane, giving, with the precipitate, a total of 4.77 g (42% yield): mp 301° C. (dec); $^1$H NMR (DMSO-$d_6$) δ 2.41 and 2.42 (2 s, 9H), 3.05 (m, 4H), 3.29 (m, 4H), 4.08 (s, 4H), 7.18 (dd, J=5.9, 3.6 Hz, 2H), 7.30 (dd, J=5.9, 3.7 Hz, 2H), 7.44 (m, 6H), 7.55 (d, J=8.3 Hz, 2H), 7.73 (d, J=8.3 Hz, 4H), 9.38 (s, 2H).

B. Synthesis of 2,3-Benzo-1,4,7,10,13-pentaazacyclopentadecane 5,6-Benzo-1,10,13-tris(p-toluenesulfonyl)-1,4,7,10,13-pentaazacyclopentadecan-3,8-dione prepared as in Example 37A (3.001 g, 3.98 mmol) was placed in a flask containing 1,2-dimethoxyethane (dme, 60 ml) under argon and was stirred in a cold water bath while a dme solution of lithium aluminum hydride (0.5M, 80 ml, 40.0 mmol) was added over a 5 min period. The reaction mixture became translucent. Five min later heating was started, with reflux starting 15 min later. During the heating period a white solid began to appear. The reaction was refluxed for 36.25 h, then allowed to cool to room temperature. After placing the reaction flask in a cold water bath, water (1.5 ml) was cautiously added dropwise, followed by 15% aqueous sodium hydroxide (1.5 ml), then water (4.5 ml). This mixture was stirred for 45 min. Tetrahydrofuran (90 ml) was added, and stirring was continued for an hour longer. The mixture was filtered through a Buchner funnel under an inverted funnel delivering nitrogen. The filtrate was evaporated under reduced pressure, leaving a white solid. This solid was recrystallized from hot acetonitrile under argon giving 0.848 g (81% yield) of white crystals: mp 152.5°–153° C. (under nitrogen); $^1$H NMR (CDCl$_3$) δ 0.63–1.97 (2 br s, 3H), 2.67 (m, 4H), 2.89 (m, 4H), 3.00 (m, 4H), 3.15 (br m, 4H), 4.33 (s, 2H), 6.61 (m, 2H), 6.75 (m, 2H); Exact mass (M+H)$^+$: calcd, 264.2188; found, 264.2220 ($C_{14}H_{26}N_5$).

C. Synthesis of [Manganese(II)dichloro(2,3-Benzo-1,4,7,10,13-pentaazacyclopentadecane)]

2,3-Benzo-1,4,7,10,13-pentaazacyclopentadecane prepared as in Example 37B (0.35 g, 1.33 mmol) was added to a hot anhydrous MeOH solution (50 ml) containing anhydrous manganese(II) chloride (0.167 g, 1.33 mmol) under a dry nitrogen atmosphere. After refluxing for 2 h, the solution was stirred overnight at room temperature. The solution was taken to dryness and cold EtOH (7 ml) was added to the reddish powder. All of the red color dissolved in the EtOH leaving a white solid which was collected by filtration. The solid was recrystallized from EtOH/ethyl ether to give 0.19 g (37% yield) of a white solid after drying in vacuo: FAB mass spectrum (NBA) m/z (relative intensity) 388 (M$^+$, 2), 353/355 [(M–Cl)$^+$, 100/28], 317 (38); Anal. calcd for $C_{14}H_{25}N_5MnCl_2$: C, 43.20; H, 6.47; N, 17.99. Found: C, 42.74; H, 6.79; N, 17.06.

EXAMPLE 38

A. Synthesis of 3,6,9,12,18-Pentaazabicyclo[12.3.1] octadeca-1(18),14,16-trien-2,13-dione Triethylenetetramine (14.71 g, 97.6 mmol) was added to a 2 liter round bottom flask, nitrogen saturated methanol (1.25 liters) was added under a stream of argon in the flask and the 2,6-dimethyl pyridinedicarboxylate (19.56 g, 99.2 mmol) was added. The reaction mixture was heated to reflux for 24 h, then cooled to room temperature. The colorless solution was evaporated under reduced pressure to give a white solid. This was dissolved in methanol-chloroform (30:70), and flash filtered through silica gel in a large sintered glass funnel (15 cm diameter, 8.5 cm depth of silica) eluting with the same solvent system. Eight 500 to 700 ml fractions were collected. Thin layer chromatography (methanol-chloroform (35:65), R$_f$ somewhat variable just beyond origin, 0.10 to 0.18) indicated that fractions 3 through 6 contained product. These fractions were combined and the solvent was removed under reduced pressure giving 11.12 g (41% yield) of product: mp 224°–7° C.; $^1$H NMR (CDCl$_3$) δ 1.28 (br s, 2H), 2.86 (s, 4H), 2.97 (t, J=5.6 Hz, 4H), 3.52 (m, 4H), 7.99 (t, J=7.8 Hz, 1H), 8.24 (d, J=7.6 Hz, 2H), 9.12 (br s, 2H).

B. Synthesis of 3,6,9,12,18-Pentaazabicyclo[12.3.1] octadecan-2,13-dione 3,6,9,12,18-Pentaazabicyclo[12.3.1]octadeca-1(18),14,16-trien-2,13-dione prepared as in Example 38A (1.0 g, 3.6 mmol) was dissolved in methanol (75 ml) and concentrated hydrochloric acid (2.14 g, 21.7 mmol) was added, then the catalyst platinum dioxide hydrate (0.5 g, 2 mmol). The mixture was heated to 60° C. and hydrogenated at 60 psi for 24 h. A white crystalline solid formed during the hydrogenation. The reaction mixture was filtered, and the precipitate was washed with water to dissolve it. The filtrate was concentrated to remove the alcohol and sodium hydroxide (1.0N) was added to raise the pH to 11. This solution was extracted five times with dichloromethane (75 ml each), the solvent was removed under reduced pressure, and the resulting white solid was dried on the vacuum line to give 0.74 g (73% yield) of product: mp 193°–195.5° C. (dec); $^1$H NMR (CD$_2$Cl$_2$) δ 0.79–1.48 (several m, 5H), 1.88 (m, 2H), 2.01 (m, 2 H), 2.63–2.88 (several m, 8 H), 3.10 (m, 2H), 3.24 (m, 2H), 3.36 (m, 2H), 7.71 (s, 2H).

C. Synthesis of 3,6,9,12,18-Pentaazabicyclo[12.3.1] octadecane

Lithium aluminum hydride in tetrahydrofuran (thf, 1.0M, 25 ml, 25.0 mmol) was added to anhydrous thf (25 ml) in a 250 ml flask under argon containing a stir bar. A slurry of 3,6,9,12,18-pentaazabicyclo[12.3.1]octadecan-2,13-dione prepared as in Example 38B (1.196 g, 4.326 mmol) in thf (50 ml) was added to the stirred lithium aluminum hydride solution (over about 10 min), and about 35 ml more thf was added to this to aid the addition. Gas evolved as the slurry went in; the color was beige and the reaction mixture was heterogeneous. After about 10 min of stirring, a reflux condenser was connected to the flask, and the reaction mixture was heated to reflux. The reaction mixture became yellow. Heating was stopped after 16 h, and the reaction mixture was cooled to room temperature. Water (0.95 ml) was added slowly with water bath cooling. Gas evolution occurred, and the reaction was exothermic. Next, 15% aqueous sodium hydroxide (0.95 ml) was added, and then 2.85 ml more water. After stirring for about an hour, thf (60 ml) was added and the stirring was continued. The mixture was filtered 1 h later under a strong flow of nitrogen from an inverted funnel, and the filtrate was stripped and placed on the vacuum line. The solid was recrystallized from hot acetonitrile under argon to give 631 mg (58% yield) of long white needles: mp 90°–90.5° C. (under nitrogen); $^1$H NMR (CDCl$_3$) δ 1.05 (m, 2H), 1.26 and 1.36 (br s and quart. t, J=13.0, 4.0 Hz, 3H), 1.50 (m, 2H), 1.80 (br m, 3H), 2.40–3.05 (several m, 19H): Exact mass (M+H)$^+$: calcd, 256.2501; found, 256.2513 (C$_{13}$H$_{30}$N$_5$).

D. Synthesis of [Manganese(II)dichloro(3,6,9,12, 18-Pentaazabicyclo[12.3.1]octadecane)]

3,6,9,12,18-Pentaazabicyclo[12.3.1]octadecane prepared as in Example 38C (0.405 g, 1.59 mmol) was added to a refluxing solution of anhydrous MeOH (50 ml) containing anhydrous manganese(II) chloride (0.200 g, 1.59 mmo) under a dry nitrogen atmosphere. After refluxing for 2 h, the solution was stirred overnight at room temperature. The solution was taken to dryness. The solid was dissolved in EtOH (10 ml) and the solution was filtered through celite. Ethyl ether was added to the filtrate which induced crystallization of a white solid. The solid was collected by filtration, washed with ethyl ether and dried in vacuo to give 0.43 g (72% yield) of a white solid as product: FAB mass spectrum (NBA) m/z (relative intensity) 380 (M$^+$, 3), 345/ 347 [(M−Cl)$^+$, 100/2]; Anal. calcd for C$_{14}$H$_{31}$N$_5$MnCl$_2$: C, 40.96; H, 7.67; N, 18.37. Found: C,40.85; H, 7.72; N, 18.32.

EXAMPLE 39

Synthesis of [Manganese(II)dichloro(2,13-Dimethyl-3,6,9,12,18-pentaazabicyclo[12.3.1] octadeca-1(18),14,16-triene)]

A mixture of [manganese(II)dichloro(2,13-dimethyl-3,6, 9,12,18pentaazabicyclo[12.3.1] octadeca-1(18),2,12,14,16-pentaaene)] prepared as in Example 26 (2.0 g, 5.0 mmol) and 5% Rh/C (0.75 g) in anhydrous methanol (175 ml) was hydrogenated under 1000 psi H$_2$ at 100° C. for 24 h. The mixture was removed from the hydrogenation apparatus and activated carbon was added. The mixture was filtered through celite and the solution was stripped to dryness. Ethanol (7 ml) was added and the solution was filtered. A white precipitate formed in the filtrate and the crystals were collected by filtration. After washing with ethyl ether and drying in vacuo, 0.71 g (40% yield) of the product was obtained as a white solid: FAB mass spectrum (NBA) m/z (relative intensity) 402 (M$^+$, 1), 367/369 [(M−Cl)$^+$, 100/30]; Exact Mass (M−Cl)$^+$: calcd, 367.1336; found, 367.1375 (C$_{15}$H$_{23}$N$_5$MnCl).

EXAMPLE 40

A. Synthesis of Boc-Tyr(OBzl)-Gly-Gly-OEt

A solution of BocTyr(OBzl) (20.0 g, 53.9 mmol) and TEA (7.50 ml, 54.2 mmol) in anhydrous DMF (200 ml) was cooled to −10 ° C. in an ice-salt bath and treated with ethyl chloroformate (5.20 ml, 54.2 mmol) dropwise over 2 min. The resulting mixture was allowed to stir at −10 ° C. for 20 min and treated with a slurry of Gly-Gly-OEt●HCl (10.6 g, 53.9 mmol) and TEA (7.50 ml, 54.2 mmol) in anhydrous DMF (100 ml) all at once. The ice bath was removed and the mixture was allowed to warm to room temperature over 1 h and then heated to 50 ° C. for 30 min. The mixture was diluted with ethyl acetate (300 ml) and washed with 1N sodium bisulfate (100 ml), water (100 ml), saturated sodium bicarbonate (100 ml) and brine (100 ml). The ethyl acetate layer was dried (magnesium sulfate), filtered and concentrated to afford 24.6 g (89% yield) of the pure tripeptide as a white powder: $^1$H NMR (CDCl$_3$) δ 1.27 (t, J=7.0 Hz, 3H), 1.40 (s, 9H), 3.02 (d of ABq, Δv=39.2 Hz, J=13.9, 6.9 Hz, 2H), 3.88–4.07 (m, 4H), 4.18 (q, J=7.0 Hz, 2H), 4.37 (q, J=6.7 Hz, 1H), 5.03 (s, 2H), 5.40 (d, J=6.9 Hz, 1H) , 6.91 (d, J=8.7, 2H), 7.14 (d, J=8.7 Hz, 2H), 7.20 (t, J=5.4 Hz, 1H), 7.25 (t, J=5.4 Hz, 1H), 7.30–7.45 (m, 5H).

B. Synthesis of Tyr(OBzl)-Gly-Gly-OEt●TFA salt

To a solution of Boc-Tyr(OBzl)-Gly-Gly-OEt prepared as in Example 40A (127.0 g, 247.3 mmol) in methylene chloride (1058 ml) was added TFA (265.0 ml, 3.44 mol) and the resulting mixture was allowed to stir at room temperature for 30 min. The solution was concentrated and the residue was triturated with ether (200 ml) to afford 126.0 g (100% yield) of the trifluoroacetate salt as a paste: $^1$H NMR (DMSO-d$_6$) δ 1.19 (t, J=7.2 Hz, 3H), 3.05 (d of ABq, Δv=45, J=9.0, 5.4 Hz, 2H), 3.77–3.93 (m, 4H), 4.09 (q, J=7.2 Hz, 2H), 5.08 (s, 2H), 6.97 (d, J=8.6 Hz, 2H), 7.19 (d, J=8.6 Hz, 2H), 7.31–7.45 (m, 5H), 8.19 (br s, 3H), 8.38 (t, J=5.9H, 1H), 8.82 (t, J=5.5 Hz, 1H) .

C. Synthesis of Boc-Gly-Gly-Tyr(OBzl)-Gly-Gly-OEt

To a solution of Boc-Gly-Gly (22.9 g, 98.1 mmol) in anhydrous DMF (600 ml) was added EDC●HCl (20.8 g, 108.5 mmol), HOBT●H$_2$O and Tyr(O-Bzl)-Gly-Gly-OEt●TFA (50.0g, 98.1 mmol) prepared as in Example 40B (50.0 g, 98.1 mmol). The pH of the mixture was adjusted to ~8 by the addition of TEA (measured by spotting the reaction mixture on moistened Hydrion paper) and stirred at room temperature for 19 h thereafter. At this time the DMF was evaporated and the residue was taken up into ethyl acetate (600 ml), washed with 1N sodium bisulfate (150 ml), water (150 ml), saturated sodium bicarbonate (150 ml) and brine (150 ml). The ethyl acetate layer was then dried (magnesium sulfate), the drying agent filtered and the ethyl acetate allowed to stand at room temperature overnight for crystallization. The solid was filtered, washed with a minimal amount of ethyl acetate and dried thoroughly at high vacuum to afford 30.0 g (49% yield) of pure pentapeptide as a white powder: $^1$H NMR (DMSO-d$_6$) δ 1.19 (t, J=7.2 Hz, 3H), 1.38 (s, 9H), 2.75 (dd, J=14.0, 10.0 Hz, 1H), 3.00 (dd, J=14.0, 4.4 Hz, 1H), 3.55–3.85 (m, 8H), 4.09 (q, J=7.2 Hz, 2H), 4.48 (m, 1H), 5.05 (s, 2H), 6.90 (d, J=8.4 Hz, 2H), 6.97 (t, J=5.6 Hz, 1H), 7.15 (d, J=8.4 Hz, 2H) , 7.30–7.45 (m, 5H), 7.91 (t, J=4.8 Hz, 1H), 8.10 (d, J=8.0 Hz, 1H), 8.14 (t, J=5.6 Hz, 1H), 8.31 (t, J=6.0 Hz, 1H).

D. Synthesis of Gly-Gly-Tyr(OBzl)-Gly-Gly●TFA

To a solution of Boc-Gly-Gly-Tyr(OBzl)-Gly-Gly-OEt prepared as in Example 40C (22.5 g, 35.8 mmol) in methanol (148 ml) was added 2.5N sodium hydroxide (63.4 ml, 158.0 mmol) all at once and the resulting mixture was stirred for 30 min thereafter. After this time the methanol was evaporated and the pH of the solution was adjusted to 7.5 with 3N HCl and then to 3.4 with 1N sodium bisulfate. The acidified mixture was then extracted with ethyl acetate (3×100 ml) and the combined extracts were dried (magnesium sulfate). The drying agent was filtered and the ethyl acetate solution was concentrated to afford 21.6 g (100% yield) of the free acid as a white foam. To a solution of Boc-Gly-Gly-Tyr(OBzl)-Gly-Gly (21.6 g, 36.0 mmol) in methylene chloride (180 ml) at room temperature was added TFA (45.0 ml, 584.0 mmol) and the resulting solution was stirred at room temperature for 30 min. After this time the solution was concentrated and the residue was stirred with ether (250 ml) for 30 min. The white solid was filtered and dried at high vacuum to afford 22.5 g (100% yield) of the pure pentapeptide TFA salt: $^1$H NMR (DMSO-d$_6$) δ 2.73

(dd, J=14.0, 9.7 Hz, 1H), 3.00 (dd, J=14.0, 4.4 Hz, 1H), 3.59 (bs, 2H), 3.67–3.91 (m, 6H), 4.51 (dt, J=8.3, 4.7 Hz, 1H), 5.04 (s, 2H), 6.90 (d, J=8.7 Hz, 2H), 7.17 (d, J=8.7 Hz, 2H), 7.29–7.46 (m, 5H), 8.09 (m, 4H), 8.29 (d, J=8.2 Hz, 1H), 8.34 (t, J=5.5 Hz, 1H), 8.54 (t, J=5.5 Hz, 1H).

E. Synthesis of Cyclo-(Gly-Gly-Tyr(OBzl)-Gly-Gly-)

This compound was synthesized by the method of Veber, D. F et al., J. Org. Chem. 44, 3101–5 (1979). To a solution of Gly-Gly-Tyr(OBzl)-Gly-Gly●TFA prepared as in Example 40D (11.1 g, 18.1 mmol) in anhydrous DMF (2400 ml) at −30 °C. was added DPPA (4.89 ml, 22.7 mmol) and the pH of the resulting mixture was adjusted to ~8 with TEA (measured by spotting the reaction mixture on moistened Hydrion paper). This mixture was then allowed to stand at −25 °C. (internal temperature) for 48 h. The pH was monitored periodically and maintained at ~8 by further addition of TEA. The mixture was then allowed to stand at 0° C. (internal temperature) for 48 h. The pH was again monitored periodically and maintained at ~8 by further addition of TEA. After this time the reaction mixture was diluted with water (2400 ml) and stirred with Bio-Rad AG 501-X8 (mixed-bed) resin (845 g) for 6 h. The resin was separated by filtration and the solvent was concentrated to a volume of ~100 ml (only DMF remains). The cyclic peptide was precipitated by the addition of ~200 ml of ether. The material was triturated with refluxing THF for 18 h, filtered hot and cryopumped for another 18 h to afford 5.40 g (62% yield) of the pure cyclic peptide as a white powder: mp 280°–2° C. (dec); $^1$H NMR (DMSO-$d_6$) δ 2.71 (dd, J=12.0, 8.0 Hz, 1H), 2.97 (dd, J=13.6, 6.4 Hz, 1H), 3.44–3.83 (m, 7H), 3.92 (dd, J=16.0, 7.6 Hz, 1H), 4.38 (q, J=7.2 Hz, 1H), 5.04 (s, 2H), 6.85 (d, J=8.4 Hz, 2H), 7.10 (d, J=8.4, 2H), 7.28–7.42 (m, 5H), 7.74 (t, J=4.8 Hz, 1H), 8.01 (br s, 1H), 8.13 (t, J=4.8 Hz, 1H), 8.18 (br s, 1 H), 8.20 (br s, 1H); Exact mass (M+Li)$^+$: calcd., 488.2122; found, 488.2167 ($C_{24}H_{27}N_5O_6Li$).

F. Synthesis of 2-(S)-(4-Benzyloxybenzyl)-1,4,7,10,13-pentaazacyclopentadecane.

An oven-dried 500 ml flask containing a glass stir bar was allowed to cool under argon flow and charged with cyclo-(Gly-Gly-Tyr (OBzl) -Gly-Gly-) prepared as in Example 40E (10.0 g, 20.8 mmol) and anhydrous THF (100 ml). Stirring was initiated, the flask was immersed in an ice-water bath and 1M lithium aluminum hydride in THF was added (240 ml, 240 mmol) dropwise via syringe over 10 min. The ice-water bath was removed, the reaction was allowed to stir at room temperature for 30 min and refluxed for 45 h thereafter. The reaction mixture was cooled to 0° C. and quenched (cautiously) by the dropwise addition of saturated sodium sulfate (~50 ml). The resulting mixture was concentrated to a dry white powder in vacuo and triturated with refluxing methylene chloride (500 ml) for 45 min. The solid residue was filtered and the hot trituration was repeated. The combined methylene chloride solutions were concentrated in vacuo to afford 7.70 g of a yellow solid. Recrystallization from hexanes and then from acetonitrile afforded 4.85 g (57% yield) of the product as a white solid: mp=74°–80° C.; $[\alpha]_d^{20}$=+27.6° (c=0.011, methanol); $^1$H NMR (CDCl$_3$) δ1.75 (br s, 5H), 2.31 (dd, J=11.2, 8.4 Hz, 1H), 2.46 (dd, J=12.4, 6.8 Hz, 1H), 2.60–3.00 (m, 19H), 5.04 (s, 2H), 6.93 (d, J=8.6 Hz, 2H), 7.11 (d, J=8.6 Hz, 2H), 7.32–7.52 (m, 5H); Exact mass (M+H)+: calcd., 412.3076; found, 412.3055 ($C_{24}H_{38}N_5O$); Anal. calcd. for $C_{24}H_{38}N_5O$: C, 70.04; H, 9.06; N, 17.02. Found: C, 69.89; H, 9.07; N, 16.93.

G. Synthesis of {Manganese(II)dichloro[2-(S)-(4-Benzyloxybenzyl)-1,4,7,10,13-pentaazacyclopentadecane]}

A solution of 2-(4-benzyloxybenzyl)-1,4,7,10,13-pentaazacyclopentadecane prepared as in Example 40F (1.60 g, 3.89 mmol) and anhydrous manganese(II) chloride (489.0 mg, 3.89 mmol) were refluxed in anhydrous methanol (50 ml) under a dry nitrogen atmosphere for 2 h and then allowed to stir at room temperature overnight. The solution was evaporated to dryness, redissolved in acetone and filtered through celite. This solution was evaporated to dryness and taken up into hot ethanol (15 ml). Ether (50 ml) was added to precipitate a yellow-red oil. The supernatant was decanted and stripped to dryness to afford a colorless oil. The colorless oil was stirred with THF (20 ml) to afford 840 mg (39% yield) of the product as a white solid: $[\alpha]_d^{20}$=+16.1° (c=0.006, methanol); FAB mass spectrum (NBA) m/z (relative intensity); 536 [(M–H)$^+$, 1], 501/503 [(M–Cl)$^+$, 100/30]. Anal. Calcd. for $C_{24}H_{37}N_5OMnCl_2$: C, 53.60; H, 6.94; N, 13.03. Found: C, 53.66; H, 6.98; N, 12.88.

EXAMPLE 41

Synthesis of {Manganese(II)dichloro[2-(S)-(4-Hydroxybenzyl)-1,4,7,10,13-pentaazacyclopentadecane]}

To a solution of {manganese(II)dichloro[2-(S)-(4-benzyloxybenzyl)-1,4,7,10,13-pentaazacyclopentadecane]} prepared as in Example 40G (206 mg, 0.38 mmol) in ethanol (20 ml) was added Pd(C) (105 mg) and the mixture was stirred under an atmosphere of $H_2$ (63 psi) for 18 h at room temperature. The mixture was filtered through celite (1 g) with the aid of ethanol (20 ml) and the filtrate was concentrated. Recrystallization from ether-ethanol afforded 114 mg (67% yield) of the product a white solid: $[\alpha]_d^{20}$=+19.7° (c=0,005, methanol); FAB mass spectrum (NBA) m/z 447 (M$^+$, 1), 411/413 [(M–Cl)$^+$ 100/35]. Anal. Calcd. for $C_{17}H_{31}N_5OMnCl_2$: C, 45.65; H, 6.99; N, 15.66; Cl, 15.85. Found: C, 44.52; H, 6.82; N, 15.00; Cl, 15.67.

EXAMPLE 42

Stopped-Flow Kinetic Analysis

Stopped-flow kinetic analysis has been utilized to determine whether a compound can catalyze the dismutation of superoxide (Riley, D. P., Rivers, W. J. and Weiss, R. H., "Stopped-Flow Kinetic Analysis for Monitoring Superoxide Decay in Aqueous Systems," Anal. Biochem, 196, 344–349 [1991]). For the attainment of consistent and accurate measurements all reagents were biologically clean and metal-free. To achieve this, all buffers (Calbiochem) were biological grade, metal-free buffers and were handled with utensils which had been washed first with 0.1N HCl, followed by purified water, followed by a rinse in a 10$^{-4}$ M EDTA bath at pH 8, followed by a rinse with purified water and dried at 65° C. for several hours. Dry DMSO solutions of potassium superoxide (Aldrich) were prepared under a dry, inert atmosphere of argon in a Vacuum Atmospheres dry glovebox using dried glassware. The DMSO solutions were prepared immediately before every stopped-flow experiment. A mortar and pestle were used to grind the yellow solid potassium superoxide (~100 mg). The powder was then ground with a few drops of DMSO and the slurry transferred to a flask containing an additional 25 ml of DMSO. The resultant slurry was stirred for ½ h and then filtered. This procedure gave reproducibly ~2 mM concentrations of superoxide in DMSO. These solutions were transferred to a glovebag under nitrogen in sealed vials prior to loading the syringe under nitrogen. It should be noted that the DMSO/superoxide solutions are extremely sensitive to water, heat, air, and extraneous metals. A fresh, pure solution has a very slight yellowish tint.

Water for buffer solutions was delivered from an in-house deionized water system to a Barnstead Nanopure Ultrapure Series 550 water system and then double distilled, first from alkaline potassium permanganate and then from a dilute EDTA solution. For example, a solution containing 1.0 g of potassium permanganate, 2 liters of water and additional sodium hydroxide necessary to bring the pH to 9.0 were added to a 2-liter flask fitted with a solvent distillation head. This distillation will oxidize any trace of organic compounds in the water. The final distillation was carried out under nitrogen in a 2.5-liter flask containing 1500 ml of water from the first still and $1.0 \times 10^{-6}$M EDTA. This step will remove remaining trace metals from the ultrapure water. To prevent EDTA mist from volatilizing over the reflux arm to the still head, the 40-cm vertical arm was packed with glass beads and wrapped with insulation. This system produces deoxygenated water that can be measured to have a conductivity of less than 2.0 nanomhos/cm$^2$.

The stopped-flow spectrometer system was designed and manufactured by Kinetic Instruments Inc. (Ann Arbor, Mich.) and was interfaced to a MAC IICX personal computer. The software for the stopped-flow analysis was provided by Kinetics Instrument Inc. and was written in Quick-Basic with MacAdios drivers. Typical injector volumes (0.10 ml of buffer and 0.006 ml of DMSO) were calibrated so that a large excess of water over the DMSO solution were mixed together. The actual ratio was approximately 19/1 so that the initial concentration of superoxide in the aqueous solution was in the range 60–120 µM. Since the published extinction coefficient of superoxide in H$_2$O at 245 nm is ~2250 M$^{-1}$ cm$^{-1}$ (1), an initial absorbance value of approximately 0.3–0.5 would be expected for a 2-cm path length cell, and this was observed experimentally. Aqueous solutions to be mixed with the DMSO solution of superoxide were prepared using 80 mM concentrations of the Hepes buffer, pH 8.1 (free acid+Na form). One of the reservoir syringes was filled with 5 ml of the DMSO solution while the other was filled with 5 ml of the aqueous buffer solution. The entire injection block, mixer, and spectrometer cell were immersed in a thermostatted circulating water bath with a temperature of 21.0°±0.5° C.

Prior to initiating data collection for a superoxide decay, a baseline average was obtained by injecting several shots of the buffer and DMSO solutions into the mixing chamber. These shots were averaged and stored as the baseline. The first shots to be collected during a series of runs were with aqueous solutions that did not contain catalyst. This assures that each series of trials were free of contamination capable of generating first-order superoxide decay profiles. If the decays observed for several shots of the buffer solution were second-order, solutions of manganese(II) complexes could be utilized. In general, the potential SOD catalyst was screened over a wide range of concentrations. Since the initial concentration of superoxide upon mixing the DMSO with the aqueous buffer was ~$1.2 \times 10^{-4}$M, we wanted to use a manganese (II) complex concentration that was at least 20 times less than the substrate superoxide. Consequently, we generally screened compounds for SOD activity using concentrations ranging from $5 \times 10^{-7}$ to $8 \times 10^{-6}$M. Data acquired from the experiment was imported into a suitable math program (e.g., Cricket Graph) so that standard kinetic data analyses could be performed. Catalytic rate constants (Table 1) for dismutation of superoxide by manganese(II) complexes (Examples 1–9, and 27–41) were determined from linear plots of observed rate constants ($k_{obs}$) versus the concentration of the manganese(II) complexes. $k_{obs}$ values were obtained from linear plots of in absorbance at 245 nm versus time for the dismutation of superoxide by the manganese(II) complexes. Inactive manganese(II) complexes (Examples 10–26 and MnCl$_2$) failed to perturb the second order spontaneous decay of superoxide.

TABLE 1

CATALYTIC RATE CONSTANTS FOR DISMUTATION OF SUPEROXIDE BY MANGANESE(II) COMPLEXES AT pH 8.1 AND 21° C.

| Example | $k_{CAT}$ (M$^{-1}$sec$^{-1}$) |
|---|---|
| 1 | $1.98 \times 10^{+7}$ |
| 2 | $2.67 \times 10^{+7}$ |
| 3 | $2.39 \times 10^{+7}$ |
| 4 | $2.29 \times 10^{+7}$ |
| 5 | $1.91 \times 10^{+7}$ |
| 6 | $1.72 \times 10^{+7}$ |
| 7 | $2.07 \times 10^{+7}$ |
| 8 | $1.85 \times 10^{+7}$ |
| 9 | $2.30 \times 10^{+7}$ |
| 10 (comparative) | ND |
| 11 (comparative) | ND |
| 12 (comparative) | ND |
| 13 (comparative) | ND |
| 14 (comparative) | ND |
| 15 (comparative) | ND |
| 16 (comparative) | ND |
| 17 (comparative) | ND |
| 18 (comparative) | ND |
| 19 (comparative) | ND |
| 20 (comparative) | ND |
| 21 (comparative) | ND |
| 22 (comparative) | ND |
| 23 (comparative) | ND |
| 24 (comparative) | ND |
| 25 (comparative) | ND |
| 26 (comparative) | ND |
| MnCl$_2$ (comparative) | ND |
| 27 | $2.40 \times 10^{+7}$ |
| 28 | $1.91 \times 10^{+7}$ |
| 29 | $1.75 \times 10^{+7}$ |
| 30 | $1.42 \times 10^{+7}$ |
| 31 | $1.76 \times 10^{+7}$ |
| 32 | $6.98 \times 10^{+6}$ |
| 33 | $2.90 \times 10^{+7}$ |
| 34 | $7.08 \times 10^{+6}$ |
| 35 | $3.44 \times 10^{+7}$ |
| 36 | $1.20 \times 10^{+7}$ |
| 37 | $4.60 \times 10^{+6}$ |
| 38 | $5.28 \times 10^{+6}$ |
| 39 | $1.00 \times 10^{+7}$ |
| 40 | $1.70 \times 10^{+7}$ |
| 41 | $1.82 \times 10^{+7}$ |

ND = Manganese(II) complex has no detectable superoxide dismutase activity. ($k_{cat} < 10^6$ M$^{-1}$sec$^{-1}$)

Manganese(II) complexes of nitrogen-containing macrocyclic ligands (Examples 1–9 and 27–41) are effective as catalysts for the dismutation of superoxide (Table 1). Examples 1–9 and 27–41 have catalytic rate constants ($k_{cat}$) between $4.60 \times 10^{+6}$ –$3.44 \times 10^{+7}$M$^{-1}$ sec$^{-1}$. However, as can be seen from Table 1, SOD activity of manganese(II) complexes is highly dependent on the size, number of nitrogens, degree of unsaturation, and substituents of the macrocyclic ligand. For example, Examples 1–9 and 27–41 which are manganese(II) complexes of 15-membered ligands containing five nitrogens are effective catalysts for the dismutation of superoxide. N-methylated manganese(II) complexes of 16-membered macrocyclic ligands containing five nitrogens (Example 16) and 17-membered macrocyclic ligands containing five nitrogens (Examples 11 and 12) are ineffective at catalyzing the dismutation of superoxide. Manganese(II) complexes of 15-membered macrocyclic ligands containing only four nitrogens (Examples 17, 18 and 21) do not have SOD activity. Other manganese(II) complexes with less than or greater than 15-membered macrocyclic ligands with less than five or greater than five nitrogens (Examples 10, 13, 14, 20 and 25) are not catalysts for the dismutation of superoxide. Manganese(II) complexes with macrocyclic ligands containing unsaturation (Examples 22–24 and 26) do not catalyze the dismutation of superoxide. $MnCl_2$ alone (no macrocyclic ligand) has no SOD activity. N-methylated manganese(II) complexes of 15-membered macrocyclic ligands containing five nitrogens (Examples 15 and 19) are ineffective at dismutating superoxide. However, C-substitution of manganese(II) complexes of 15-membered macrocyclic ligands with five nitrogens (Examples 2–7 and 28–41) are effective SOD catalysts.

EXAMPLE 43

In Vivo Evaluation

Mouse colitis model. Manganese(II) complexes (Examples 1–3, 5–8) which had been demonstrated to have SOD activity by stopped flow kinetic analysis (Table 1) were tested in the mouse acetic acid-induced colitis model (Krawisz, J. E., Sharon, P., and Stenson, W. F., (1984) *Gastroenterology* 87, 1344–1350). Mice were lightly anesthetized. A solution of 3% (v/v) aqueous acetic acid was instilled intracolonically via a flexible polyethylene tube. After 24 hours, the animals were killed and colonic tissue samples were obtained. Tissue samples were assessed biochemically for the neutrophil marker enzyme, myeloperoxidase (MPO). The colonic tissue samples were minced, homogenized in detergent, and sonicated. After centrifugation, enzyme activities were assayed spectrophotometrically by determining the decomposition of peroxide using o-dianisidine as the hydrogen donor. Data was obtained as the absorbance (460 nm) at 20 minutes. Test agents were given intracolonically at a dose of 30 mg/kg body weight 30 minutes before acetic acid instillation as a sonicated suspension in 0.5% aqueous methyl cellulose. Vehicle was given to appropriate acetic acid control animals. Normal tissue was obtained from control animals which received only vehicle. Colonic myeloperoxidase activities were determined as units/g wet weight of tissue. Reduction of colonic myeloperoxidase activity by test agents in acetic acid-treated mice is expressed as % inhibition (Table 2). Colonic myeloperoxidase activity correlated with the degree of tissue inflammation as assessed by visual and histological analysis.

As can be seen from Table 2, manganese(II) complexes (Examples 1–3, 5–8) which catalyze the dismutation of superoxide as demonstrated by stopped-flow kinetic analysis are anti-inflammatory in the mouse acetic acid colitis model as evidenced by a reduction in colonic myeloperoxidase activity.

TABLE 2

INHIBITION OF COLONIC MYELOPEROXIDASE ACTIVITY BY MANGANESE(II) COMPLEXES IN THE MOUSE ACETIC ACID COLITIS MODEL

| Example | % Inhibition of Colonic Myeloperoxidase Activity 30 mg/kg dose, (intracolonic) |
|---|---|
| 1 | 69 |
| 2 | 47 |
| 3 | 42 |
| 5 | 70 |
| 6 | 48 |
| 7 | 77 |
| 8 | 32 |

EXAMPLE 44

In Vitro Evaluation

Neutrophil-Mediated Cytotoxicity Assay

Human peripheral blood neutrophils were isolated from fresh venous blood of healthy volunteers. EDTA anticoagulated blood was separated using a single step density centrifugation (Polymorphprep; Nycomed Pharma, Oslo, Norway) followed by several washes in Hank's balanced salt solution supplemented with 0.5% BSA (Bovine Serum Albumin) (HBSSB) and the hypertonic lysis of erythrocytes. Neutrophils were counted via Coulter electronic particle counter and resuspended in HBSSB supplemented with 25% Endothelial Basal Medium (EBM), (Clonetics Corporation, San Diego, Calif.) at a concentration of $5 \times 10^6$ polymorphonuclear leukocytes (PMN)/ml.

The cytotoxic effects of stimulated neutrophils on endothelial cells were determined using a $^{51}$Cr-release assay as previously described (Moldow, C. F., and Jacob, H. S. (1984) *Methods Enzymol.* 105, 378–385). Confluent monolayers of human aortic endothelial cells (HAE cells; Clonetics) grown in 96-well culture plates were prelabeled with 1 µCi/well $^{51}$Cr ($Na_2{}^{51}Cr_2O_4$, New England Nuclear, Boston, Mass.). The cells were incubated for 18 h at 37° C., then cytokine-activated with 10 Units/well human recombinant tumor necrosis factor-α (hrTNF-α; Monsanto Company, St. Louis, Mo.) for 4 h at 37° C. The cells were washed twice to remove unincorporated radioactivity with Hank's balanced salt solution supplemented with 0.5% BSA. To assess inhibition of PMN-mediated cytotoxicity, manganese(II) complexes at various doses (0–300 µM) were added to five replicate wells/dose of HAE cells immediately prior to the addition of PMN. Suspensions of PMN in HBSSB supplemented with 25% Endothelial Basal Medium were added to the wells at a neutrophil to endothelial cell ratio of 50:1. The PMN were allowed to adhere for 15 minutes at 37° C., primed with 125 Units/well hrTNF-α (Berkow, R. L., Wang, D., Larrick, J. W., Dodson, R. W., and Howard, T. H. (1987) *J. Immunol.* 139, 3783–3791; Varani, J.; Bendelow, M. J. Sealey, D. E.; Kunkel, S. L.; Gannon, D. E.; Ryan, U. S.; and Ward, P. A. (1987) Lab. Invest., 59, 292–295) for 10 minutes, and stimulated with human recombinant complement component C5a (Sigma Chemical, St. Louis, Mo.). (Sacks, T., Moldow, C. F., Craddock, P. R., Bowers, T. K., and Jacob, H. S. (1978) *J. Clin. Invest.*, 61, 1161–1167). Stimulation of the human neutrophils by this method results in enhanced superoxide production. After an additional incubation of 4 hours at 37° C., 200 µl of the 250 µl reaction volume (soluble fraction) was removed to a tube for counting. The cells were washed twice with 200 µl HBSSB (nonadherent fraction) and the washes pooled with the soluble fraction. The adherent fraction was collected by lysing the HAE cells with 200 μl 1N NaOH for 30 minutes and removing to separate tubes. Both fractions were analyzed by gamma scintillation spectrometry. The percentage cytotoxicity was calculated by the following formula:

$$\% \text{ Cytotoxicity} = \frac{\text{cpm (soluble + nonadherent fractions)}}{\text{cpm (soluble + nonadherent + adherent fractions)}} \times 100$$

Specific cytotoxicity reflects the difference between $^{51}$Cr-release induced by stimulated PMN and unstimulated PMN. The $IC_{50}$ values for the manganese(II) complexes for protection against neutrophil-mediated cytotoxicity were determined from a computer-driven logistic regression equation from a plot of % specific cytotoxicity versus the concentration of the manganese(II) complex.

As can be seen from Table 3, manganese(II) complexes (Examples 1–8 and 27) which catalyze the dismutation of superoxide as demonstrated by stopped-flow kinetic analysis are protective against human neutrophil-mediated cytotoxicity. Examples 1–8 and 27 have $IC_{50}$ valves in the 22–119 μM concentration range.

TABLE 3

PROTECTION AGAINST HUMAN NEUTROPHIL-MEDIATED KILLING OF HUMAN AORTIC ENDOTHELIAL CELLS BY THE MANGANESE(II) COMPLEXES OF THIS INVENTION

| Example | $IC_{50}$ (μM) |
|---------|----------------|
| 1 | 25 |
| 2 | 53 |
| 3 | 37 |
| 4 | 57 |
| 5 | 65 |
| 6 | 76 |
| 7 | 22 |
| 8 | 119 |
| 27 | 26 |

$IC_{50}$ is the concentration of test agent which gives 50% inhibition of specific cytotoxicity.

EXAMPLE 45

In Vitro Evaluation

Nitric Oxide: Rat Lung Fibroblast cGMP Reporter Assay

Manganese(II) complex (Example 1) which had been demonstrated to have SOD activity by stopped flow kinetic analysis (Table 1) was tested in a rat lung fibroblast cell assay for detecting the level of guanosine 3',5'-cyclic monophosphate (cGMP) to determine the effect of the manganese (II) complexes on the level of cGMP. The assay is described in Ishii, I., Sheng, H., Warner, T. D., Förstermann, V. and Murad, F., *Am. J. Physiol.*, 261 (Heart Circ. Physiol. 30); H598–H603, 1991 modified in that the nitric oxide synthase (NOS) is added directly to the cells. Rat lung fibroblast cells were grown to confluence on a 48-well tissue culture plate containing Earle's salts medium. The medium is removed and the cells washed twice with minimal essential medium buffered with Earle's salts. A nitric oxide (NO) generating system consisting of enzyme (NOS), nicotinamide adenine dinucleotide phosphate (NADPH), arginine and required cofactors, such as tetrahydrobiopterin and flavin adenine dinucleotide (FAD) is subsequently added to each well. In cases where the complex of Example 1 was added, addition occurred with the NO generating system. After five minutes of incubation, each reaction is terminated, cellular cGMP extracted and measured by radioimmunoassay.

The capacity of the rat lung fibroblast cells to respond to NO was confirmed by adding sodium nitroprusside (SNP), a compound which spontaneously degrades to NO and results in increased cGMP levels. Next, crude NOS (prepared from endotoxin-treated RAW 264.7 cells) was added to the rat lung fibroblast cells to determine their response to enzymatically generated NO. A dose-dependent increase in cGMP with increasing amounts of enzyme was obtained. Superoxide dismutase (SOD) addition augmented cellular cGMP levels.

Since the complex of Example 1 is a SOD mimic, then it should give a similar enhancement of NO stimulated cGMP levels. Concentrations of the complex of Example 1 from 1 micromolar to 1 millimolar resulted in a dose-dependent increase in cGMP levels (see Table 4). Also, basal levels of cGMP are not increased by the addition of complex of Example 1 alone (1 millimolar). Moreover, the complex of Example 1 does not increase NOS activity as measured by citrulline production. Thus, the complex of Example i potentiates the effect of NO on cGMP levels inside cells expressing a soluble guanylate cyclase.

Nitric oxide is produced by endothelial cells, diffuses into smooth muscle cells where it activates the soluble guanylate cyclase resulting in vasorelaxation. Superoxide anion can react with NO to form peroxynitrite, thereby reducing the concentration of NO available for guanylate cyclase activation. The effectiveness of the complex of Example 1 in increasing cGMP levels indicates its ability to lower superoxide levels. Furthermore, the ability of the complexes of the invention to increase cGMP levels indicates the complexes of the invention have application in treating diseases where potentiation of NO levels would be beneficial, such as hypertension.

EXAMPLE 46

In Vitro Evaluation

Rat Aortic Ring Assay

Manganese(II) complex (Example 1) which had been demonstrated to have SOD activity by stopped flow kinetic analysis (Table 1) was tested in a rat aortic ring assay.

The maintenance of blood pressure in vivo is a balance between contraction and relaxation factors. A major contributor to the relaxation of blood vessels is the NO released from vascular endothelial cells. Increasing the concentration or extending the effective half-life of NO results in decreased blood pressure due to elevated cGMP content in smooth muscle cells. An investigation was undertaken to demonstrate the activity of the complex of Example 1 to protect NO and thereby facilitate the relaxation of rat aortic rings. The aortic rings were prepared using a Furchgott procedure (described in Furchgott, R. F., "Role of Endothelium in Response of Vascular Smooth Muscle", Circ. Res. 53: 557–573, 1983) with changes in tension recorded. In all preparations, initial tension (1.5 grams) was produced with 30 mM KCl. Relaxation to the complex of Example 1 was endothelium and dose-dependent from 0.05 to 300 micromolar with a maximum relaxation of 45% (see Table 5). This data is consistent with the belief that the complex of Example 1 will protect endogenously produced NO. Treatment of rat aortic rings with the complex of Example 1 (at 5 micromolar for 1 min.) augmented cellular cGMP levels 2.5 fold. Moreover, the complex of Example 1 (0.5 and 5.0 micromolar) had an additive effect on the relaxation response to either acetylcholine (0.1 and 1.0 micromolar) (see Table 6) or sodium nitroprusside (0.001 to 10 micromolar) (see Table 7).

The results indicate that the rat aortic ring system agrees quite well with the cGMP reporter assay and further demonstrates the applicability of the complexes of the invention for treating hypertension.

EXAMPLE 47

In vivo Evaluation

Rat Hemodynamic Model

Manganese(II) complex (Example 1) which had been demonstrated to have SOD activity by stopped-flow kinetic analysis (Table 1) was tested in conscious rats to determine its effect on mean blood pressure.

Catheters were inserted into the femoral vein, femoral artery and bladder of male Sprague-Dawley rats (250–325 grams total body weight) anesthetized with ether. The rats were then placed in individual restraining cages and allowed to regain consciousness. Blood pressure was measured by a standard pressure transducer and physiograph. Increasing doses of the manganese(II) complex of Example 1 (prepared in an aqueous solution) were given as single bolus injections. The results of the tests can be found in FIG. 1. The blood pressure values represent the mean arterial blood pressure from the mean values of 3 rats. It is unknown whether the transient (3–5 minute) nature of the blood pressure drop can be attributed to the pharmacokinetic behavior of the complex of Example 1 or to reflex control by the sympathetic nervous system since the rats were not ganglion blocked. Thus, the potentiation by the complex of Example 1 of the vasorelaxant effects of NO is consistent with the proposed mechanism of action as an SOD mimic.

The results indicate that the complexes of the invention are effective in reducing the blood pressure of rats and further demonstrates the applicability of the complexes of the invention for treating hypertension.

TABLE 4

Effect of Manganese(II) Complex of Example 1 on the Potentiation of the Effect of Nitric Oxide on Cyclic GMP in Rat Lung Fibroblast Cells

| Condition | Mean cGMP (fmol/well/10) | Standard Deviation |
|---|---|---|
| Basal | 11.0 | 4.0 |
| NOS | 22.0 | 2.6 |
| Complex[a] (1 mM) | 11.7 | 3.1 |
| NOS/Complex[a] (0.0001 mM) | 19.3 | 2.5 |
| NOS/Complex[a] (0.001 mM) | 21.7 | 2.3 |
| NOS/Complex[a] (0.01 mM) | 43.7 | 15.2 |
| NOS/Complex[a] (0.10 mM) | 54.7 | 15.0 |
| NOS/Complex[a] (1.0 mM) | 60.3 | 10.7 |

[a]Manganese(II) Complex of Example 1

TABLE 5

Relaxation of Rat Aortic Rings by the Manganese(II) Complex of Example 1

| Concentration of Complex,[a], [b] µM | % Relaxation | SEM |
|---|---|---|
| 0.05 | 6.2 | 1.0 |
| 0.1 | 9.8 | 1.8 |
| 0.5 | 18.0 | 2.1 |
| 1.0 | 25 | 3.7 |
| 5.0 | 35 | 4.2 |
| 50 | 35 | 4.7 |
| 100 | 36 | 5.2 |
| 300 | 44 | 4.3 |

[a]contraction with 30 mM KCl.
[b]complex is the Manganese(II) complex of Example 1.

TABLE 6

Potentiation of Acetycholine (ACh) Relaxation in Rat Aortic Rings Contracted with 30 mM KCl

| Treatment | % Relaxation[b] | SEM |
|---|---|---|
| ACh, $10^{-7}$ M | 28 (n = 2) | — |
| Complex[a], 0.5 µM | 3.4 (n = 4) | 1.3 |
| Complex[a], 0.5 µM + ACh, $10^{-7}$ M[c] | 35 (n = 3) | 9.5 |
| Complex[a], 5.0 µM | 32 (n = 4) | 3.6 |
| Complex[a], 5.0 µM + ACh, $10^{-7}$ M[c] | 56 (n = 3) | 5.7 |

[a]Complex is the Manganese(II) complex of Example 1.
[b]n is the number of measurements.
[c]Complex and ACh were mixed simultaneously.

TABLE 7

Potentiation of Sodium Nitroprusside (NP) Relaxation in Rat Aortic Rings Contracted with 30 mM KCl

| Treatment | % Relaxation[b] | SEM |
|---|---|---|
| NP, 0.001 µM | 2.6 | 1.2 |
| NP, 0.01 µM | 13 | 4.1 |
| NP, 0.1 µM | 50 | 5.5 |
| NP, 1.0 µM | 87 | 1.8 |
| NP, 10 µM | 87 | 1.3 |
| NP, 100 µM | 87 | 1.4 |
| Complex[a], 0.5 µM | 3.4 | 1.3 |
| Complex[a], 0.5 µM + NP, 0.001 µM | 5.2 | 2.5 |
| Complex[a], 0.5 µM + NP, 0.01 µM | 30 | 7.6 |
| Complex[a], 0.5 µM + NP, 0.1 µM | 79 | 7.0 |
| Complex[a], 0.5 µM + NP, 1.0 µM | 96 | 1.2 |
| Complex[a], 5 µM | 32 | 3.6 |
| Complex[a], 5 µM + NP, 0.001 µM | 30 | 4.2 |
| Complex[a], 5 µM + NP, 0.01 µM | 50 | 7.6 |
| Complex[a], 5 µM + NP, 0.1 µM | 90 | 3.1 |
| Complex[a], 5 µM + NP, 0:1 µM | 97 | 1.2 |

[a]Complex is the Manganese(II) complex of Example 1.

What is claimed is:

1. Pharmaceutical composition in unit dosage form useful for dismutating superoxide comprising (a) a therapeutically or prophylactically effective amount of a complex represented by the formula:

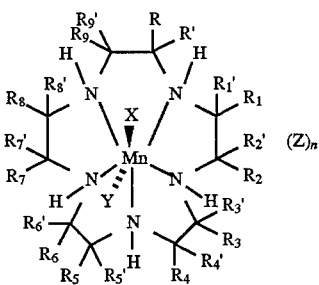

wherein at least one of R and R', $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$ together with the carbon atom to which they are attached independently form a saturated, partially saturated or unsaturated ring structure having 3 to 20 carbon atoms; or at least one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$, together with a different one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ which is attached to a different carbon atom in the macrocyclic ligand may be bound to form a strap represented by the formula

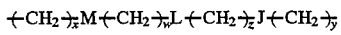

wherein w, x, y and z independently are integers from 0 to 10, and M, L and J are independently selected from the group consisting of alkyl, alkenyl, alkynyl, aryl, cycloalkyl, heteroaryl, alkaryl, alkheteroaryl, aza, amide, ammonium, thia, sulfonyl, sulfinyl, sulfonamide, phosphonyl, phosphinyl, phosphino, phosphonium, keto, ester, carbamate, urea, thiocarbonyl, borates, boranes, boraza, silyl, siloxy, silaza and combinations thereof; or combinations thereof; and the remaining "R" groups are hydrogen or, optionally, R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently are selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent; and combinations thereof; wherein X, Y and Z are ligands independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphortic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, or X, Y and Z are independently attached to one or more of the "R" groups and n is an integer from 0 to 3; and (b) a nontoxic, pharmaceutically acceptable carrier, adjuvant or vehicle.

2. A compound which is a complex represented by the formula:

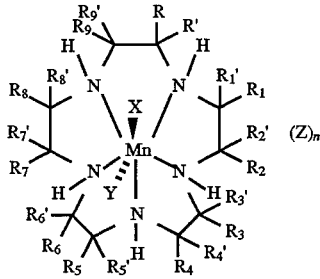

wherein at least one of R and R', $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atoms to which they are attached independently form a saturated, partially saturated or unsaturated ring structure having 3 to 20 carbon atoms; or at least one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ together with a different one of R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ which is attached to a different carbon atom in the macrocyclic ligand may be bound to form a strap represented by the formula

wherein w, x, y and z independently are integers from 0 to 10, and M, L and J are independently selected from the group consisting of alkyl, alkenyl, alkynyl, aryl, cycloalkyl, heteroaryl, alkaryl, alkheteroaryl, aza, amide, ammonium, thia, sulfonyl, sulfinyl, sulfonarnide, phosphonyl, phosphinyl, phosphino, phosphonium, keto, ester, carbamate, urea, thiocarbonyl, borates, boranes, boraza, silyl, siloxy, silaza and combinations thereof; or combinations thereof; and the remaining "R" groups are hydrogen or, optionally, R, R', $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, and $R'_9$ independently are selected from the group consisting of alkyl, alkenyl, alkynyl, cycloalkyl, cycloalkenyl, cycloalkylalkyl, cycloalkylcycloalkyl, cycloalkenylalkyl, alkylcycloalkyl, alkenylcycloalkyl, alkylcycloalkenyl, alkenylcycloalkenyl, heterocyclic, aryl and aralkyl radicals and radicals attached to the α-carbon of α-amino acids; or $R_1$ or $R'_1$ and $R_2$ or $R'_2$, $R_3$ or $R'_3$ and $R_4$ or $R'_4$, $R_5$ or $R'_5$ and $R_6$ or $R'_6$ $R_7$ or $R'_7$, and $R_8$ or $R'_8$, and $R_9$ or $R'_9$ and R or R' together with the carbon atoms to which they are attached independently form a saturated, partially saturated or unsaturated cyclic having 3 to 20 carbon atoms; or R or R' and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, and $R_8$ or $R'_8$ and $R_9$ or $R'_9$ together with the carbon atoms to which they are attached independently form a nitrogen containing heterocycle having 2 to 20 carbon atoms provided that when the nitrogen containing heterocycle is an aromatic heterocycle which does not contain a hydrogen attached to the nitrogen, the hydrogen attached to the nitrogen in said formula, which nitrogen is also in the macrocycle and the R groups attached to the same carbon atoms of the macrocycle are absent; and combinations thereof; wherein X, Y and Z are ligands independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic add, thiotosylate, and anions of ion exchange resins, or the corresponding anions thereof, or X, Y and Z are independently attached to one or more of the "R" groups and n is an integer from 0 to 3.

3. Method of preventing or treating a disease or disorder which is mediated, at least in part, by superoxide comprising administering to a subject in need of such prevention or treatment, a therapeutically, prophylactically, pathologically, or resuscitatively effective amount of a complex of claim 2.

* * * * *